United States Patent
Blain

(10) Patent No.: US 10,702,570 B2
(45) Date of Patent: Jul. 7, 2020

(54) COMPOSITIONS TARGETING THE INTERACTION DOMAIN BETWEEN P27KIP1 AND BRK AND METHODS OF USE THEREOF TO INHIBIT P27 Y PHOSPHORYLATION AND CDK4 ACTIVITY

(71) Applicant: The Research Foundation for the State University of New York, Albany, NY (US)

(72) Inventor: Stacy W. Blain, Brooklyn, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/351,904

(22) Filed: Nov. 15, 2016

(65) Prior Publication Data

US 2017/0065662 A1    Mar. 9, 2017

Related U.S. Application Data

(63) Continuation-in-part of application No. PCT/US2015/031128, filed on May 15, 2015.

(60) Provisional application No. 61/994,087, filed on May 15, 2014, provisional application No. 62/113,166, filed on Feb. 6, 2015.

(51) Int. Cl.
| | |
|---|---|
| *A61K 38/00* | (2006.01) |
| *C07K 14/47* | (2006.01) |
| *C07K 14/00* | (2006.01) |
| *C12Q 1/48* | (2006.01) |
| *A61K 31/519* | (2006.01) |
| *A61K 38/08* | (2019.01) |
| *A61K 38/10* | (2006.01) |
| *A61K 38/45* | (2006.01) |
| *C07K 14/78* | (2006.01) |

(52) U.S. Cl.
CPC .......... *A61K 38/005* (2013.01); *A61K 31/519* (2013.01); *A61K 38/08* (2013.01); *A61K 38/10* (2013.01); *A61K 38/45* (2013.01); *C07K 14/00* (2013.01); *C07K 14/4702* (2013.01); *C07K 14/4738* (2013.01); *C12Q 1/48* (2013.01); *C12Y 207/10* (2013.01); *A61K 38/00* (2013.01); *C07K 14/78* (2013.01); *G01N 2333/912* (2013.01)

(58) Field of Classification Search
CPC ..... C12Y 207/10; C07K 14/4738; A61K 8/14
See application file for complete search history.

(56) References Cited

U.S. PATENT DOCUMENTS

| 2003/0008813 A1* | 1/2003 | Felgner ................. A61K 9/1272 514/44 R |
| 2003/0105000 A1* | 6/2003 | Pero ....................... A61K 38/06 514/19.3 |
| 2015/0118288 A1* | 4/2015 | Lee ........................ A61K 9/127 424/450 |

FOREIGN PATENT DOCUMENTS

WO    WO-2004018641 A2 *  3/2004  ........... C12N 9/1205

OTHER PUBLICATIONS

Malam et al. (Trends in Pharmacological 2009 30(11): 592-599) (Year: 2009).*
Brauer et al. (PLoS ONE Mar. 2011 6 (3): e14789) (Year: 2011).*
Schutz et al. (Critical Reviews in Oncology/Hematology 91 (Feb. 15, 2014) 248-256) (Year: 2014).*
Coleman et al. (Research in Immunology, 1994; 145(1): 33-36) (Year: 1994).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Tros de Ilarduya et al. (Euro. J. Pharmaceutical Sci. 2010: 40:59-170) (Year: 2010).*
Wu et al. (Molecular Therapy—Nucleic Acids (Apr. 16, 2013) 2, e84; doi:10.1038/mtna.2013.14) (Year: 2013).*
Siyanova et al., "Tyrosine kinase gene expression in the mouse small intestine," Oncogene, vol. 9, pp. 2053-2057, Mar. 14, 1994.
Mitchell et al., "Cloning and characterisation of cDNAs encoding a novel non-receptor tyrosine kinase, brk, expressed in human breast tumours," Oncogene, vol. 9, pp. 2383-2390, Apr. 7, 1994.
Russo et al., "Crystal structure of the p27Kip1 cyclin-dependent-kinase inhibitor bound to the cyclin A-Cdk2 complex," Nature, vol. 382, pp. 325-331, Jul. 25, 1996.
Neet et al., "Vertebrate non-receptor protein-tyrosine kinase families," Genes to Cells, vol. 1, pp. 147-169, 1996.
Barker et al., "BRK tyrosine kinase expression in a high proportion of human breast carcinomas," Oncogene, vol. 15, pp. 799-805, May 1, 1997.
Mitchell et al., "Characterisation and chromosome mapping of the human non receptor tyrosine kinase gene, brk," Oncogene, vol. 15, pp. 1497-1502, May 20, 1997.
Vasioukhin et al., "A role for the epithelial-cell-specific tyrosine kinase Sik during keratinocyte differentiation," Proc. Natl. Acad. Sci., vol. 94, pp. 14477-14482, Dec. 1997.
Sherr et al., "CDK inhibitors: positive and negative regulators of G1-phase progression," Genes Dev., vol. 13, pp. 1501-1512, 1999.
Derry et al., "Sik (BRK) Phosphorylates Sam68 in the Nucleus and Negatively Regulates Its RNA Binding Ability," Molecular and Cellular Biology, vol. 20(16), pp. 6114-6126, Aug. 2000.
Yu et al., "Specific protection against breast cancers by cyclin D1 ablation," Nature, vol. 411, pp. 1017-1021, Jun. 28, 2001.

(Continued)

*Primary Examiner* — Peter J Reddig
(74) *Attorney, Agent, or Firm* — Heslin Rothenberg Farley & Mesiti P.C.

(57) ABSTRACT

Compositions and methods for the treatment of malignancy are disclosed.

11 Claims, 22 Drawing Sheets

(22 of 22 Drawing Sheet(s) Filed in Color)

Specification includes a Sequence Listing.

(56) References Cited

OTHER PUBLICATIONS

Hulit et al., "ErbB-2-induced mammary tumor growth: the role of cyclin D1 and p27Kip1," Biochemical Pharmacology, vol. 64, pp. 827-836, 2002.
Muraoka et al., "ErbB2/Neu-Induced, Cyclin D1-Dependent Transformation Is Accelerated in p27-Haploinsufficient Mammary Epithelial Cells but Impaired in p27-Null Cells," Molecular and Cellular Biology, vol. 22(7), pp. 2204-2219, Apr. 2002.
Cesareni et al., "Can we infer peptide recognition specificity mediated by SH3 domains?," Febs Letters, vol. 513, pp. 38-44, Jan. 4, 2002.
Ortega et al., "Cyclin D-dependent kinases, INK4 inhibitors and cancer," Biochim. Biophys. Acta, vol. 1602, pp. 73-87, Jan. 17, 2002.
Koo et al., "Purification and Spectroscopic Characterization of the Human Protein Tyrosine Kinase-6 SH3 Domain," J. Biochem. Mol. Biol., vol. 35, No. 3, pp. 343-347, May 2002.
Serfas et al., "Brk, Srm, Frk, and Src42A Form a Distinct Family of Intracellular Src-Like Tyrosine Kinases," Oncology Research, vol. 13, pp. 409-419, Sep. 20, 2002.
Schmidt et al., "Cell Cycle Inhibition by FoxO Forkhead Transcription Factors Involves Downregulation of Cyclin D," Molecular and Cellular Biology, vol. 22(22), pp. 7842-7852, Nov. 2002.
Manning et al., "The Protein Kinase Complement of the Human Genome," Science, vol. 298, pp. 1912-1934, Dec. 6, 2002.
Derry et al., "Altered localization and activity of the intracellular tyrosine kinase BRK/Sik in prostate tumor cells," Oncogene, vol. 22, pp. 4212-4220, 2003.
Blain et al., "p27 as a target for cancer therapeutics," Cancer Cell, vol. 3, pp. 111-115, Feb. 2003.
Harrison et al., "Variation on an Src-like theme," Cell, vol. 112, pp. 737-740, Mar. 21, 2003.
Miller et al., "DNA Vaccination against Mutant Huntingtin Ameliorates the HDR6/2 Diabetic Phenotype," Molecular Therapy, vol. 7(5), pp. 572-579, May 2003.
Qiu et al., "Role of the Brk SH3 domain in substrate recognition," Oncogene, vol. 23, pp. 2216-2223, Sep. 29, 2003.
Malumbres et al., "Mammalian Cells Cycle without the D-type Cyclin-Dependent Kinases Cdk4 and Cdk6," Cell, vol. 118, pp. 493-504, Aug. 20, 2004.
Fry et al., "Specific inhibition of cyclin-dependent kinase 4/6 by PD 0332991 and associated antitumor activity in human tumor xenografts," Molecular Cancer Therapeutics, vol. 3(11), pp. 1427-1438, Nov. 2004.
Qiu et al., "Interaction between Brk kinase and insulin receptor substrate-4," Oncogene, vol. 24, pp. 5656-5664, May 2, 2005.
Kardinal et al., "Tyrosine phosphorylation modulates binding preference to cyclin-dependent kinases and subcellular localization of p27Kip1 in the acute promyelocytic leukemia cell line NB4," Blood, vol. 107(3), pp. 1133-1140, Feb. 1, 2006.
Malumbres et al., "Is Cyclin D1-CDK4 kinase a bona fide cancer target?" Cancer Cell, vol. 9, pp. 2-4, Jan. 2006.
Yu et al., "Requirement for CDK4 kinase function in breast cancer," Cancer Cell, vol. 9, pp. 23-32, Jan. 2006.
Bockstaele et al., "Regulation of CDK4," Cell Division, vol. 1:25, Nov. 8, 2006.
Grimmler et al., "Cdk-Inhibitory Activity and Stability of p27Kip1 Are Directly Regulated by Oncogenic Tyrosine Kinases," Cell, vol. 128, pp. 269-280, Jan. 26, 2007.
Chu et al., "p27 Phosphorylation by Src Regulates Inhibition of Cyclin E-Cdk2," Cell, vol. 128, pp. 281-294, Jan. 26, 2007.
Ostrander et al., "Breast Tumor Kinase (Protein Tyrosine Kinase 6) Regulates Heregulin-Induced Activation of ERK5 and p38 MAP Kinases in Breast Cancer Cells," Cancer Research, vol. 67(9), pp. 4199-4209, May 1, 2007.
James et al., "Differential Modification of p27Kip1 Controls Its Cyclin D-cdk4 Inhibitory Activity," Molecular and Cellular Biology, vol. 28(1), pp. 498-510, Jan. 2008.
Galea et al., "Role of Intrinsic Flexibility in Signal Transduction Mediated by the Cell Cycle Regulator, p27Kip1," J. Mol. Biol., vol. 376(3), pp. 827-838, Feb. 22, 2008.
Blain et al., "Switching cyclin D-Cdk4 kinase activity on and off," Cell Cycle, vol. 7(7), pp. 892-898, Apr. 1, 2008.
Baughn et al., "CDK2 Phosphorylation of Smad2 Disrupts TGF-β Transcriptional Regulation in Resistant Primary Bone Marrow Myeloma Cells," The Journal of Immunology, vol. 182, pp. 1810-1817, 2009.
Ray et al., "p27Kip1 Inhibits Cyclin D-Cyclin-Dependent Kinase 4 by Two Independent Modes," Molecular and Cellular Biology, vol. 29(4), pp. 986-999, Feb. 2009.
Finn et al., "PD 0332991, a selective cyclin D kinase 4/6 inhibitor, preferentially inhibits proliferation of luminal estrogen receptor-positive human breast cancer cell lines in vitro," Breast Cancer Research, vol. 11:R77, Oct. 29, 2009.
Chan et al., "Deregulation of the cell cycle by breast tumor kinase (Brk)," International Journal of Cancer, vol. 127, pp. 2723-2731, 2010.
Palka-Hamblin et al., "Identification of β-catenin as a target of the intracellular tyrosine kinase PTK6," Journal of Cell Science, vol. 123(2), pp. 236-245, Jan. 15, 2010.
Brauer et al., "Building a better understanding of the intracellular tyrosine kinase PTK6—BRK by BRK," Biochim Biophys Acta., vol. 1806(1), pp. 66-73, Aug. 2010.
Nguyen et al., "Inflammatory Mediators of Esophagitis Alter p27Kip1 Expression in Esophageal Epithelial Cells," J. Pediatr. Gastroeneterol. Nutr, vol. 51(5), pp. 556-562, Nov. 2010.
Wander et al., "p27: A Barometer of Signaling Deregulation and Potential Predictor of Response to Targeted Therapies," Clinical Cancer Research, vol. 17(1), pp. 12-18, Jan. 1, 2011.
Borriello et al., "Targeting p27Kip1 protein: its relevance in the therapy of human cancer," Expert Opinion on Therapeutic Targets, vol. 15(6), pp. 677-693, Feb. 28, 2011.
Jäkel et al., "Phosphorylation of p27Kip1 by JAK2 directly links cytokine receptor signaling to cell cycle control," Oncogene, vol. 30(32), pp. 3502-3512, Aug. 11, 2011.
Zheng et al., "Protein-tyrosine Kinase 6 Promotes Peripheral Adhesion Complex Formation and Cell Migration by Phosphorylating p130 CRK-associated Substrate," The Journal of Biological Chemistry, vol. 287(1), pp. 148-158, Jan. 2, 2012.
Jäkel et al., "Regulation of p27Kip1 by mitogen-induced tyrosine phosphorylation," Cell Cycle, vol. 11(10), pp. 1910-1917, May 15, 2012.
Asbach et al., "Comprehensive Analysis of Interactions between the Src-Associated Protein in Mitosis of 68 kDa and be Human Src-Homology 3 Proteome," PLOS ONE, vol. 7(6), Jun. 20, 2012.
Gierut et al., "Targeting Protein Tyrosine Kinase 6 Enhances Apoptosis of Colon Cancer Cells Following DNA Damage," Mol Cancer Ther, vol. 11(11), pp. 2311-2320, Nov. 2012.
Hukkelhoven et al., "Tyrosine Phosphorylation of the p21 Cyclin-dependent Kinase Inhibitor Facilitates the Development of Proneural Glioma," J. Biol. Chem., vol. 287(46), pp. 38523-38530, Nov. 9, 2012.
Blain et al., "Abstract LB-123: PTK6/BRK modulates tyrosine phosphorylation of p27Kip1 and the activity of the oncogene cyclin D-cdk4," Cancer Res., AACR 104th Meeting, Apr. 6-10, 2013.
Zheng et al., "Protein Tyrosine Kinase 6 Protects Cells from Anoikis by Directly Phosphorylating Focal Adhesion Kinase and Activating AKT," Oncogene, vol. 32(36), pp. 4304-4312, Sep. 5, 2013.
Al et al., "HER2 regulates Brk/PTK6 stability via upregulating calpastatin, an inhibitor of calpain," Cell Signal, vol. 25(9), pp. 1754-1761, Sep. 2013.
Cadoo et al., "Palbociclib: an evidence-based review of its potential in the treatment of breast cancer," Breast Cancer: Targets and Therapy, vol. 6, pp. 123-133, 2014.
Dickson et al., "Molecular Pathways: CDK4 Inhibitors for Cancer Therapy," Clinical Cancer Research, vol. 20(13), pp. 3379-3383, May 2, 2014.
Peng et al., "PTK6/BRK is expressed in the normal mammary gland and activated at the plasma membrane in breast tumors," Oncotarget, vol. 5(15), pp. 6038-6048, Jun. 30, 2014.

(56) References Cited

OTHER PUBLICATIONS

Heilmann et al., "CDK4/6 and IGF1 receptor inhibitors synergize to suppress the growth of p16INK4A-deficient pancreatic cancers," Cancer Research, vol. 74(14), pp. 3947-3958, Jul. 1, 2014.

Patel et al., "Abstract P5-08-01: Tyrosine phosphorylation of p27Kip1 regulates the activity of cyclin D-cdk4 complexes in breast cancer," Cancer Res., Thirty-seventh Annual CTRC-AACR San Antonio Breast Cancer Symposium, Dec. 9-13, 2014.

Patel et al., "BRK/protein Tyrosine Kinase 6 Phosphorylates p27Kip1, Regulating the Activity of Cyclin D—Cyclin-Dependent Kinase 4," Mol. Cell. Biol., vol. 35(9), pp. 1506-1522, May 2015.

\* cited by examiner

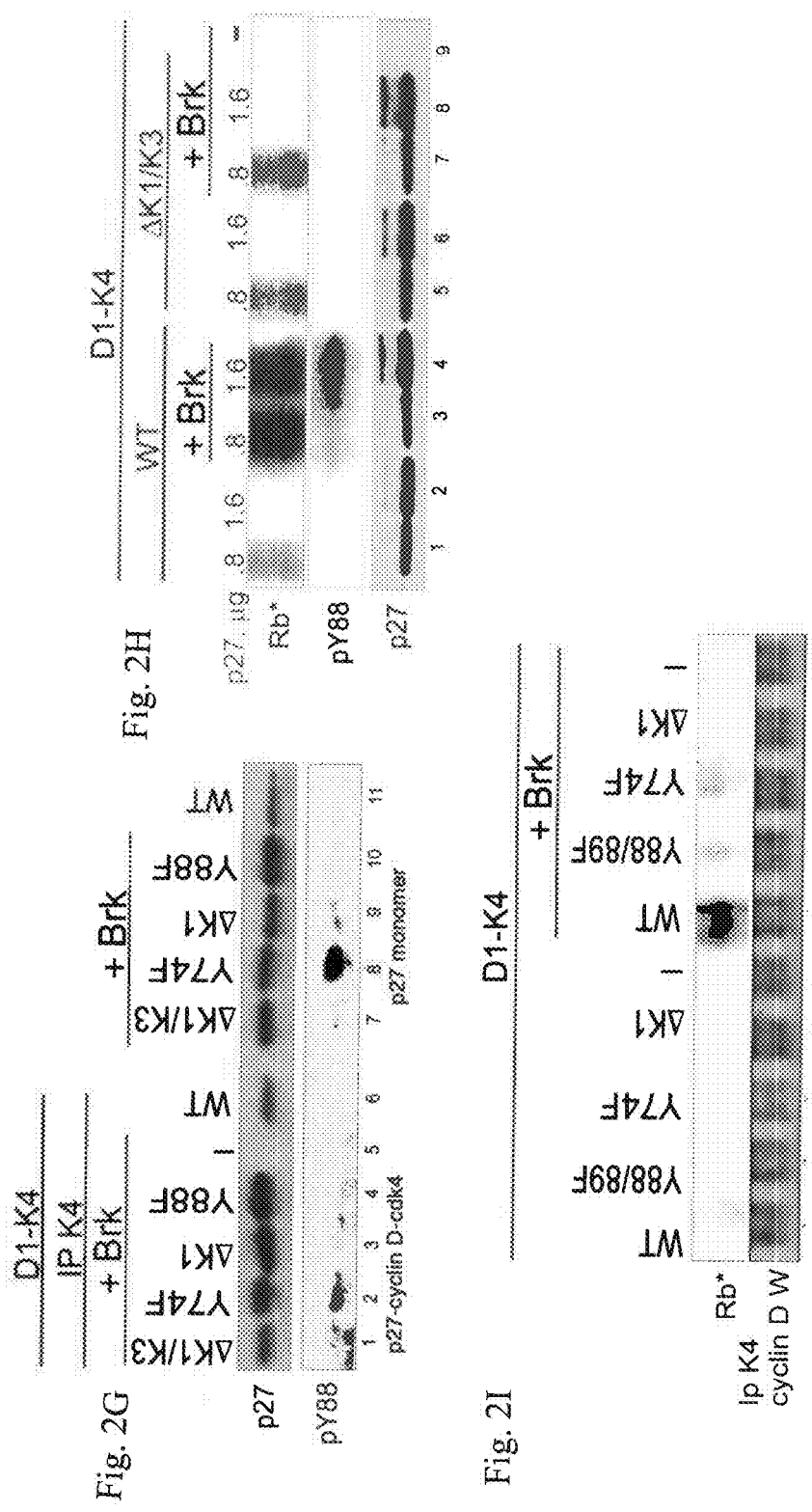

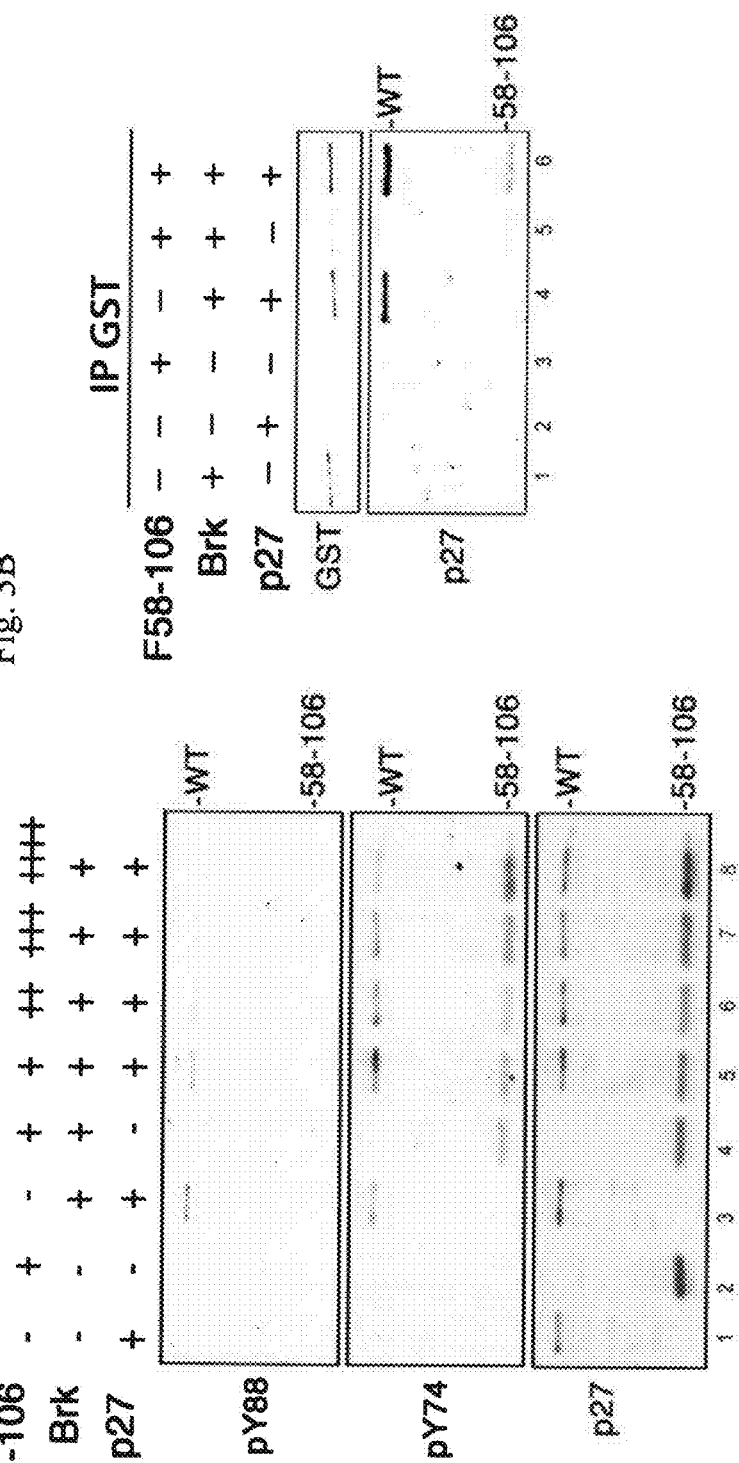

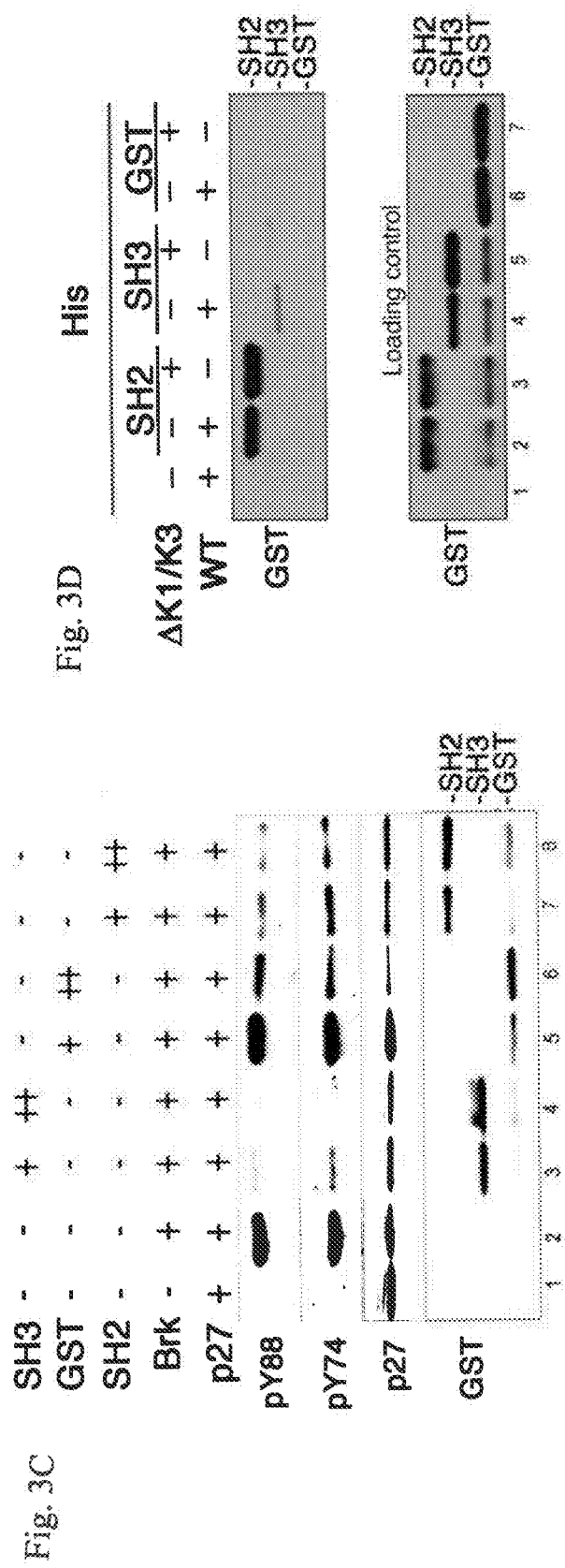

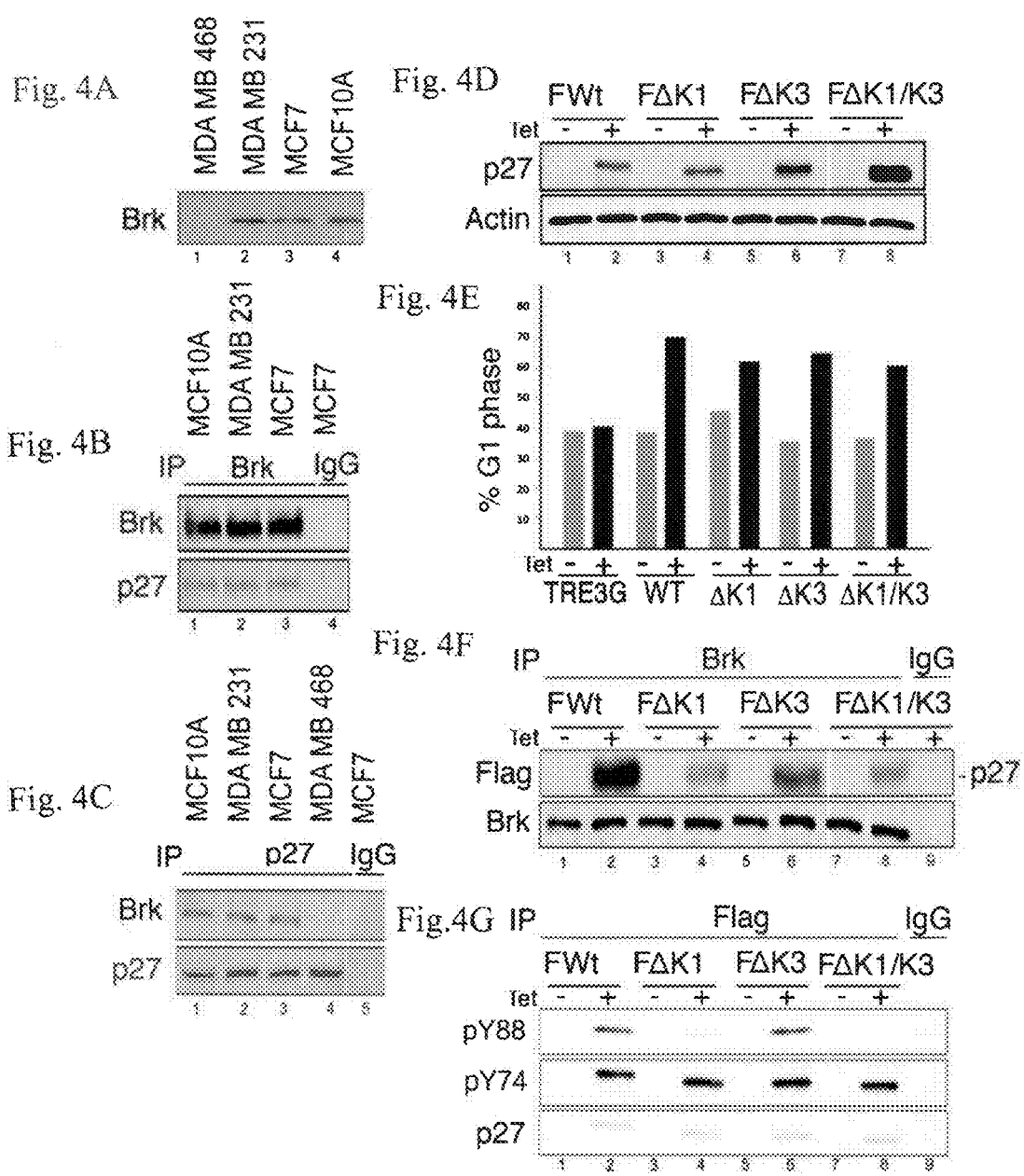

Fig. 5A
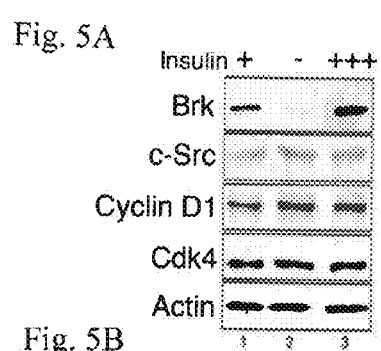
Fig. 5C
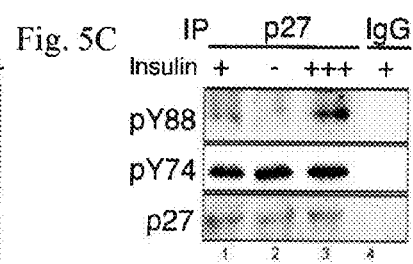
Fig. 5B
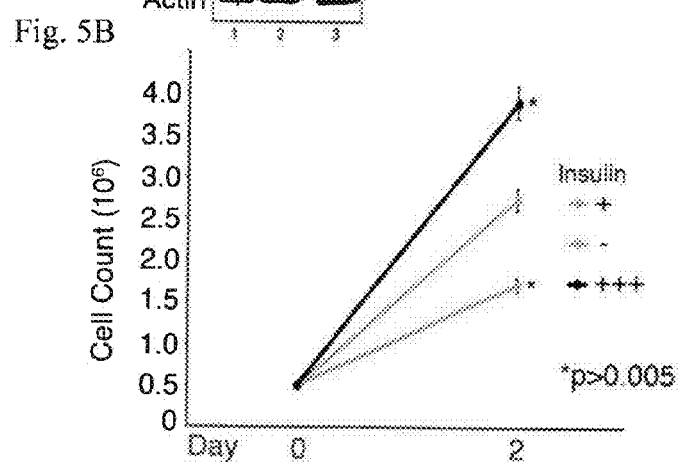
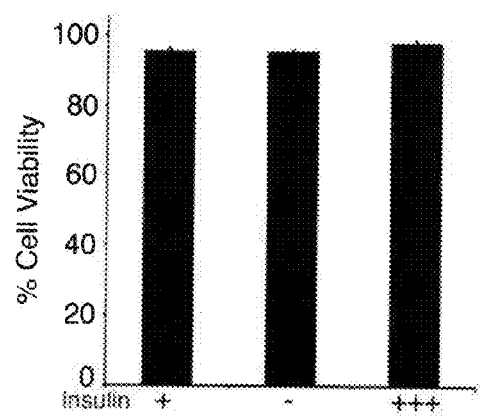

Fig. 12B

| Entry & position(s) | Q13882-2 |
|---|---|
| Description | Isoform 2 of Protein-tyrosine kinase 6, Homo sapiens<br>http://www.uniprot.org/uniprot/Q13882-2<br>https://www.ncbi.nlm.nih.gov/protein/NP_001243287 |
| Feature key | Isoform 2 (identifier: Q13882-2) [UniParc]FASTAAdd to basketAdded to basket<br>*Also known as:* ALT-PTK6, deltam5<br>*The sequence of this isoform differs from the canonical sequence as follows:*<br>   78-134: WFFGCISRSE...RHYKIWRRAG → AGHAGCAALQ...AGRALPEARA<br>   135-451: Missing. |
| Feature identifier | |

SH3
Alt

```
         10         20         30         40         50
MVSRDQAHLG PKYVGLWDFK SRTDEELSFR AGDVFHVARK EEQWWWATLL
         60         70         80         90        100
DEAGGAVAQG YVPHNYLAER ETVESEPAGH AGCAALQDLA ACRGPAAPER
        110        120        130
GGVLPQPARA CELPQGPEPV PRPAAGRALP EARA
```

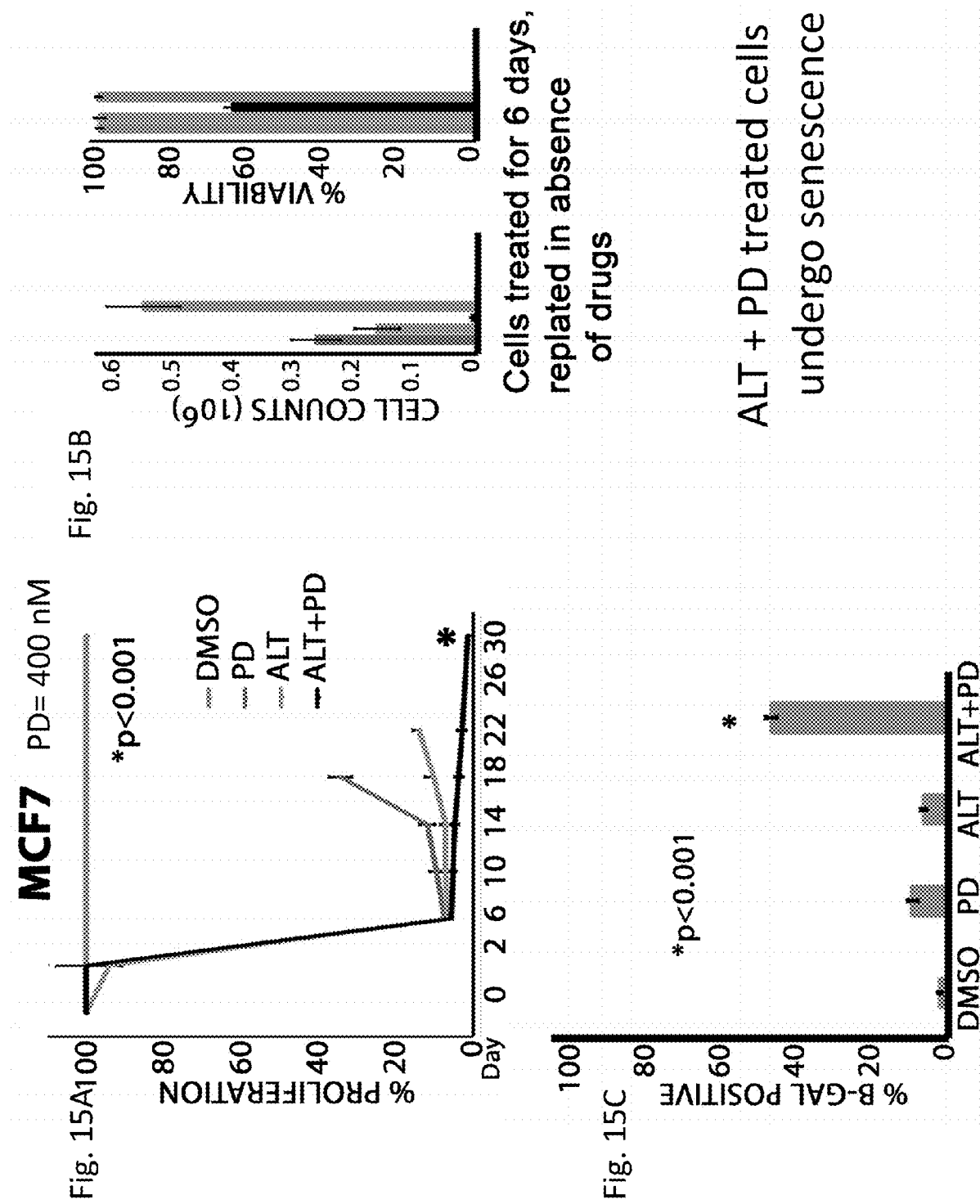

SEQUENCE LISTING

```
<160> NUMBER OF SEQ ID NOS: 17

<210> SEQ ID NO 1
<211> LENGTH: 198
<212> TYPE: PRT
<213> ORGANISM: Homo sapiens

<400> SEQUENCE: 1

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 2
<211> LENGTH: 59
<212> TYPE: PRT
<213> ORGANISM: Artificial Sequence
<220> FEATURE:
<223> OTHER INFORMATION: SH3 domain of Brk

<400> SEQUENCE: 2

Lys Tyr Val Gly Leu Trp Asp Phe Lys Ser Arg Thr Asp Glu Glu Leu
1               5                   10                  15

Ser Phe Arg Ala Gly Asp Val Phe His Val Ala Arg Lys Glu Glu Gln
            20                  25                  30

Trp Trp Trp Ala Thr Leu Leu Asp Glu Ala Gly Gly Ala Val Ala Gln
        35                  40                  45
```

Gly Tyr Val Pro His Asn Tyr Leu Ala Glu Arg
        50                  55

<210> SEQ ID NO 3
<211> LENGTH: 56
<212> TYPE: PRT
<213> ORGANISM: Artificial Sequence
<220> FEATURE:
<223> OTHER INFORMATION: SH3 domain of Src

<400> SEQUENCE: 3

Thr Phe Val Ala Leu Tyr Asp Tyr Glu Ser Arg Thr Glu Thr Asp Leu
1               5                   10                  15

Ser Phe Lys Lys Gly Glu Arg Leu Gln Ile Val Asn Asn Thr Glu Gly
            20                  25                  30

Asp Trp Trp Leu Ala His Ser Leu Thr Thr Gly Gln Thr Gly Tyr Ile
        35                  40                  45

Pro Ser Asn Tyr Val Ala Pro Ser
    50                  55

<210> SEQ ID NO 4
<211> LENGTH: 4
<212> TYPE: PRT
<213> ORGANISM: Artificial Sequence
<220> FEATURE:
<223> OTHER INFORMATION: Proline-rich sequence
<220> FEATURE:
<221> NAME/KEY: VARIANT
<222> LOCATION: (2)...(3)
<223> OTHER INFORMATION: Xaa = any amino acid

<400> SEQUENCE: 4

Pro Xaa Xaa Pro
1

<210> SEQ ID NO 5
<211> LENGTH: 11
<212> TYPE: PRT
<213> ORGANISM: Artificial Sequence
<220> FEATURE:
<223> OTHER INFORMATION: K1 site of P27

<400> SEQUENCE: 5

Arg Pro Pro Arg Pro Pro Lys Gly Ala Cys Lys
1               5                   10

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ggcctcgagc tagctctcct gcgccg                                    26

<210> SEQ ID NO 7
<211> LENGTH: 65
<212> TYPE: DNA
<213> ORGANISM: Artificial Sequence
<220> FEATURE:
<223> OTHER INFORMATION: Primer

<400> SEQUENCE: 7
ggggtctaga gccaccatgg actacaagga cgacgatgac aagcgcaagt ggaatttcga    60
ttttc                                                              65

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
aaaatctggc accacacctt ctac                                         24

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tagcacagcc tggatagcaa cg                                           22

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ccaagtatgt gggcctctgg                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
aaagaaccac ggttccgact                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gacggtggag tcggaacctg                                              20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tagttcacaa gctcgggcag                                              20

<210> SEQ ID NO 14
<211> LENGTH: 18
<212> TYPE: PRT

```
<213> ORGANISM: Artificial Sequence
<220> FEATURE:
<223> OTHER INFORMATION: K1

<400> SEQUENCE: 14

Pro Glu Phe Tyr Tyr Arg Pro Pro Arg Pro Pro Lys Gly Ala Cys Lys
1               5                   10                  15

Val Pro

<210> SEQ ID NO 15
<211> LENGTH: 16
<212> TYPE: PRT
<213> ORGANISM: Artificial Sequence
<220> FEATURE:
<223> OTHER INFORMATION: K2

<400> SEQUENCE: 15

Asp Val Ser Gly Ser Arg Pro Ala Ala Pro Leu Ile Gly Ala Pro Ala
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: K3

<400> SEQUENCE: 16

Gly Ser Val Glu Gln Thr Pro Lys Lys Pro Gly Leu Arg Arg Arg Gln
1               5                   10                  15

<210> SEQ ID NO 17
<211> LENGTH: 134
<212> TYPE: PRT
<213> ORGANISM: Homo sapiens

<400> SEQUENCE: 17

Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
                20                  25                  30

Asp Val Phe His Val Ala Arg Lys Glu Glu Gln Trp Trp Trp Ala Thr
            35                  40                  45

Leu Leu Asp Glu Ala Gly Gly Ala Val Ala Gln Gly Tyr Val Pro His
        50                  55                  60

Asn Tyr Leu Ala Glu Arg Glu Thr Val Glu Ser Glu Pro Ala Gly His
65                  70                  75                  80

Ala Gly Cys Ala Ala Leu Gln Asp Leu Ala Ala Cys Arg Gly Pro Ala
                85                  90                  95

Ala Pro Glu Arg Gly Gly Val Leu Pro Gln Pro Ala Arg Ala Cys Glu
            100                 105                 110

Leu Pro Gln Gly Pro Glu Pro Val Pro Arg Pro Ala Ala Gly Arg Ala
        115                 120                 125

Leu Pro Glu Ala Arg Ala
    130
```

US 10,702,570 B2

COMPOSITIONS TARGETING THE INTERACTION DOMAIN BETWEEN P27KIP1 AND BRK AND METHODS OF USE THEREOF TO INHIBIT P27 Y PHOSPHORYLATION AND CDK4 ACTIVITY

This application is a continuation in part application of PCT/US2015/031128 filed May 15, 2015 which claims priority to U.S. Provisional Application Nos. 61/994,087 and 62/113,166 filed May 15, 2014 and Feb. 6, 2015 respectively, each of these applications being incorporated herein by reference as though set forth in full.

The application contains an ASCII text file of 7 kilobytes, named Seqlist2 created on Oct. 16, 2018, which is hereby incorporated by reference into the present application.

FIELD OF THE INVENTION

This invention relates to the fields of cell biology and the control of cell cycle progression. More specifically the invention provides small molecules effective to modulate cell signaling associated with aberrant cellular proliferation and malignancy.

BACKGROUND OF THE INVENTION

Several publications and patent documents are cited throughout the specification in order to describe the state of the art to which this invention pertains. Each of these citations is incorporated herein by reference as though set forth in full.

Cyclin D1-cdk4 complexes promote the G0/G1 phase transition, and as such their activity is tightly regulated by a variety of mechanisms, including the transcription and translation of the mitogen sensor cyclin D1 and positive and negative regulatory phosphorylation of cdk4 (1,2). The most well-characterized substrate of cyclin D-cdk4 is the G1 gatekeeper, Retinoblastoma (Rb), and deregulation of cdk4 potentially accelerates Rb phosphorylation and cell cycle transitioning, promoting cancer development (3). Cyclin D1 and cdk4 are overexpressed in a variety of human cancers, and in mouse models, loss of either cdk4 or cyclin D1 prevents the development of certain oncogene-driven tumors, further evidence of their involvement (4-6). However, the levels of cyclin D or cdk4 in a tumor may not be reliable measures of activity, due to the fact that a third protein, an assembly factor such as p27Kip1 or p21Cip1, is required both for the stabilization and then the subsequent activation of this complex (1, 7).

Independent of its ability to assemble cyclin D-cdk4 complexes, p27 acts as a bona fide "switch" turning cyclin D-cdk4 complexes on or off, which in turn modulates cell cycle entry or exit (8, 9). Tyrosine (Y) phosphorylation of p27 on residues Y74, Y88 and Y89 opens the cyclin D-cdk4-p27 ternary complex, rendering it able to phosphorylate substrates such as Rb (9-14). Cyclin D-cdk4-p27 complexes isolated from cells in G0 lack Y phosphorylation on p27 and are catalytically inactive, while complexes isolated from proliferating cells are Y phosphorylated and active. Y88 and Y89 are part of the 3-10 helix, which has been shown to insert into the ATP binding cleft in cdks (15). When not phosphorylated, residues Y88/Y89 sequester within this binding pocket and block cdk4 activity (p27 switched OFF). NMR and other studies suggest phosphorylation of Y88/Y89 induces a conformational change in p27, ejecting the Y88/Y89 loop, opening the cyclin D-cdk4 complex, permitting both ATP access and the required phosphorylation on cdk4 residue T172 by the Cyclin Activating Kinase (CAK), the latter causing activation of cdk4 (p27 switched ON) (11, 12, 14, 16). Thus, p27's control of cyclin D-cdk4 makes it a key player in the regulation and integration of a cell's response to extracellular signals.

Members of the Src Family of Kinases (SFKs), including Src, Yes, and Lyn have been shown to phosphorylate p27 in vitro (9). Moreover, distantly related kinases, such as the Abelson kinase Abl and the Janus kinase, Jak2, also appear competent to phosphorylate p27 (11, 12, 17). The Src kinase family consists of 8 members: Src, Yes, Fyn, Fgr, Lyn, Hck, Lck, and Blk (18). Frk, Srm, Src42A and PTK6/Brk comprise a distantly related, but distinct family (19, 20). Brk is an intracellular tyrosine kinase expressed in normal epithelial cells and overexpressed in 60% of breast cancers. Brk has been shown to phosphorylate p27 in vitro and in vivo, and studies have shown that Brk is a higher affinity binder than members of the SRK family. Knockdown of Brk in breast cancer cells also prevents p27 phosphorylation, even in the presence of Src and other SFKs, suggesting that it is the physiological kinase for p27 Y phosphorylation (14). All of these kinases share a common domain organization comprising the tyrosine kinase domain (also termed SH1), as well as one each of the protein-protein interaction modules SH2 and SH3, which bind to phosphotyrosine and proline-rich sequences (PxxP), respectively. The SH2 and SH3 domains recognize specific amino acid sequences within the SFK itself, thus adopting an autoinhibited state. Upon release from this inhibition by upstream signalling molecules, the SH2 and SH3 domains are free to bind downstream SFK target proteins (21).

The principal task of the cell cycle is to ensure that a cell's DNA is faithfully duplicated and evenly distributed to daughter cells. Loss of control over this process is a hallmark of cancer. Indeed, as mentioned above, direct perturbation of most genes involved in cell cycle control has been observed in human cancers. Cell cycle transitions are tightly controlled by the actions of the cyclin-cdks. New therapeutic compounds, which modulate these actions should prove effective in the treatment of hyperproliferative disorders, including malignant disease.

SUMMARY OF THE INVENTION

In accordance with the present invention, a strategy targeting cdk4 activity in cancer cells in an indirect fashion has been implemented in order to reduce the off target effects associated with conventional agents targeting cdk4 directly.

In one embodiment of the present invention, agents that target the interaction domain between p27Kip1 and Brk, thereby modulating cell cycle progression, are disclosed.

Accordingly, the invention comprises an isolated peptide mimetic of a p27 K1 domain that inhibits phosphorylation of p27Kip1, at tyrosine 88, in a pharmaceutically acceptable carrier. Such mimetics include, without limitation, peptides of SEQ ID NO: 5 or SEQ ID NO: 14, wherein the carrier enhances cellular uptake. In another embodiment, the peptide mimetics can be packaged in a lipoplexed nanoparticle for in vivo delivery. In a preferred embodiment, the p27 K1 domain mimetic exhibits higher binding affinity for the Brk SH3 domain than the domain present in an endogenously expressed, native p27.

Mimetics of the K3 domain of p27 based on SEQ ID NO: 16 and methods of use thereof for the treatment of cancer are also provided herein.

The invention also provides a composition comprising an isolated Alt-Brk peptide of SEQ ID NO: 17 or an SH3 domain containing fragment thereof contained within a carrier which enhances cellular uptake. In one embodiment, the peptides are peptide mimetics that are optionally packaged in a lipoplexed nanoparticle for in vivo delivery. In a particularly preferred embodiment, the mimetic exhibits a higher binding affinity for a PxxP sequence than the native Brk SH3 domain. Mimetics comprising a modified alternatively spliced region of Alt-Brk are also provided.

Also encompassed within the scope of the invention are methods of treating cancer in a patient in need thereof comprising the administration a composition comprising a peptide or peptide mimetic as described above and a carrier which enhances cellular uptake in an amount effective to inhibit tumor growth in said patient. The peptides or peptide mimetics may be administered alone or in combination with an anti-cancer agent conventionally used in the treatment of cancer.

Anticancer preparations according to the present invention can include, without limitation, at least one anti cancer agent in a plurality of pharmaceutically acceptable carriers. Exemplary anti-cancer agents include palbociclib, ribociclib, abemaciclib, osirmetinib, gefitinib, lapatinib, pantitumumab, vandetanib, necitumumab, vemurafenib, sorafenib tosylate, PLX-4720, dabrafenib, paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, herceptin, vemurafenib, erlotininb, cetuximab, letrozole, fulvestrant and epothilone derivatives, although the skilled person is aware of additional anti-cancer agents that can be used to advantage in the methods of the present invention.

In a particularly preferred embodiment, the patient is a breast cancer patient, and the anticancer agent is palbociclib which acts synergistically with said mimetic to inhibit growth of, or kill cancer cells.

In cases where the mimetics are peptide mimetics, nucleic acids encoding the mimetics and vectors comprising the nucleic acids are within the scope of the invention. These nucleic acids can also be cloned within expression vectors suitable for delivery to patients in need thereof. In yet another aspect, host cells expressing the mimetics are provided. In certain embodiments, the peptide mimetics are operably linked to cell penetrating sequence tags to facilitate cellular uptake and delivery of the mimetic to a cell type of interest.

BRIEF DESCRIPTION OF THE DRAWINGS

The patent application filed contains at least one drawing executed in color. Copies of this patent or patent application publication with colored drawings will be provided by the Office upon request and payment of the necessary fee.

(FIG. 1A) p27 sequence highlighting the proline tracts of the three putative SH3 domain recruitment sites (PxxP): K1 (90-96), K2 (114-117) and K3 (188-195) (SEQ ID NO: 1). Phage-ELISA-analysis of SFK SH3 interactions with p27 (FIG. 1B) or p27's PxxP motifs (FIG. 1C). Data shown is the mean of three independent experiments±standard deviation after normalization and subtraction of the background binding to GST. (FIG. 1C) Recombinantly produced GST-K1, -K2, -K3 or GST was immobilized in 96-well plates and analyzed for binding of the phages with the Brk-, Frk-, Yes-, or Abl-SH3 domain.

FIGS. 2A-2I: Brk phosphorylates p27 in vitro. (FIG. 2A) GST-Brk or GST-Src was incubated with recombinant His-p27 or mutants, and isolated using metal agarose chromatography (HIS), followed by immunoblot analysis with p27 and GST antibodies. A direct comparison between GST-Brk and GST-Src association can be made. (FIG. 2B) WT p27 was incubated with equal μgs (with approximately equivalent specific activities) of Abl, Src or Brk in the presence of [γ-$^{32}$P]ATP. Phosphorylated products were run on SDS-Page gels and quantitated by autoradiography (N=5). (FIG. 2C) WT p27 was incubated with equal amounts of Src or Brk in the presence of ATP. Phosphorylated products were run on SDS-Page gels and assayed by immunoblot analysis with p27, pY88, pY74 antibodies. (FIG. 2D) Plot of densitometry from (FIG. 2C). (FIG. 2E) WT p27 and mutants were incubated with Brk and ATP, separated on SDS-Page gels and immunoblots were probed with p27, pY88 or pY74 antibodies. (FIG. 2F) p27-cyclin D-cdk4 ternary complexes were generated by incubation of recombinant proteins and isolated by immunoprecipitation with cdk4 antibodies. Those and monomeric p27 were phosphorylated with Brk in the presence of [γ-$^{32}$P]ATP. Phosphorylated products were run on SDS-Page gels and quantitated by autoradiography (N=5). (FIG. 2G) p27-cyclin D-cdk4 ternary complexes were generated by incubation of recombinant proteins, and then isolated by immunoprecipitation with cdk4anti bodies (lanes 1-4). These ternary complexes (lanes 1-4) and monomeric p27 variants (lanes 7-10) were phosphorylated with Brk in the presence of ATP, followed by immunoblot analysis with pY88 and p27 antibodies. (FIG. 2H) Increasing amounts of Wt or 41(1/K3 p27 were incubated with cyclin D-cdk4 and phosphorylated or mock phosphorylated by Brk, and then used in Rb kinase assays in the presence of [γ-32P]ATP. Phosphorylated Rb (Rb*) was isolated using GST-sepharose and autoradiography. p27 was recovered by metal agarose chromatography, followed by immunoblot analysis with p27 and pY88 antibodies. Lane 10 (−) is Brk without cyclin D-cdk4 or p27. (FIG. 2I) p27 and mutants were incubated in absence (lanes 1-4) or the presence (lanes 6-9) of Brk, and then incubated with cyclin D-cdk4 and used in Rb kinase assays in the presence of [γ-$^{32}$P]ATP. Lanes 5, 10: cyclin D-cdk4 without p27. Note: the low level of cyclin D-cdk4 used in this experiment will not result in detectable Rb phosphorylation. Phosphorylated GST-Rb (Rb*) was isolated using GST-sepharose followed by autoradiography. In parallel, cdk4-associated complexes were isolated by immunoprecipitation and assayed by cyclin D immunoblot analysis.

FIGS. 3A-3D: SH3:PxxP interaction is required for p27 Y88 phosphorylation. (FIG. 3A) p27 and Brk were incubated with ATP and with increasing concentrations of the PxxP competitor, F58-106, followed by immunoblot analysis with pY88, pY74 and p27 antibodies. Lane 5: + equimolar amount of F58-106 and p27, lane 6: ++2.5× F58-106, lane 7: +++5× F58-106, lane 8: ++++10× F58-106. (FIG. 3B) GST-Brk, p27 and F58-106 were incubated, immunoprecipitated with GST antibodies, followed by immunblot analysis with GST or p27 antibodies. (FIG. 3C) Increasing amounts of GST-SH3, GST-SH2 or GST peptides were incubated with p27, followed by immunoblot analysis with pY88, pY74, p27 and GST antibodies. Lanes 3, 5, 7: 2.5× competitor, lanes 4, 6, 10: 5× competitor. (FIG. 3D) GST-SH3, GST-SH2 or GST peptides were incubated with p27 or ΔK1/K3, followed by metal agarose chromatography and immunoblot analysis with GST and p27 antibodies. Loading control: GST peptides added to the reaction which are not representative of association.

FIGS. 4A-4G: Brk phosphorylates p27 in vivo. (FIG. 4A) Breast cancer (MDA MB 468, MDA MB 231, MCF7) and normal mammary epithelial cell lines (MCF10A) were analyzed by immunblot analysis with Brk antibodies. (FIG. 4B) Lysates were immunoprecipitated using the C-terminal Brk antibody and immunoblot analysis was performed using Brk and p27 antibodies (FIG. 4C) Lysates were immunoprecipitated with p27 antibodies and probed for Brk and p27. Immunoprecipitation with IgG served as a negative control. (FIGS. 4D-G) Expression of WT and p27 mutants was induced (+) by adding tetracycline to the media and compared with the un-induced cells (−). (FIG. 4D) Immunoblot analysis was performed using p27 and actin antibodies. (FIG. 4E) Lysates were analysed by PI staining and FACS analysis. (FIG. 4F) Brk was immuno-precipitated from the lysates and immunoblot analysis was performed using Flag and Brk antibodies Immunoprecipitation with IgG served as a negative control. (FIG. 4G) Flag tagged WT or mutant p27 were immunoprecipitated from the lysates using Flag antibodies and immunoblot analysis was performed using p27, pY88 and pY74. Immunoprecipiation with Flag antibodies (IgG) without the lysate served as a negative control.

FIGS. 5A-5D: Modulation of Brk protein levels modulates p27 phosphorylation. MCF7 cells were cultured in the presence of 10 μg/ml Insulin (+), no Insulin (−) or 50 μg/ml Insulin (+++). (FIG. 5A) Immunoblot analysis was performed with Brk, c-Src, Cyclin D1, cdk4 and actin antibodies. (FIG. 5B) Treated cells were counted to monitor proliferation (left panel). Viability was determined using Trypan Blue staining (right panel). (FIG. 5C) p27 was immunoprecipitated and immunoblot analysis was performed with p27, pY88 and pY74 antibodies. (FIG. 5D) Brk protein expression was knocked down by using two different siRNAs. Immunoflorescence was performed on the cells 72 h post infection. Cells were probed for Brk, p27, pY88, pY74 and c-Src.

(FIG. 6E) Cdk4 was immunoprecipitated from the lysates and recombinant Rb was added to perform an in vitro kinase assay in the presence of ATP Immunoblot analysis was performed to probe for Rb, Ser780 pRb and cdk4 Immunoprecipitation with IgG served as a negative control. (FIG. 6F) Cells were treated with different concentrations of PD0332291 or DMSO as a control at Day 2. Total cell numbers were analyzed by counting 24 and 48 hours post treatment to determine IC50 values. (FIG. 6G) Cells were treated with different concentration of PD032291 or DMSO and analyzed by PI staining and FACS analysis. % G1 content is plotted. Representative of N=3 experiments.

(FIG. 7A) Lysates from asynchronous (A) or contact arrested (G0) cells were analyzed for Brk expression using immunoblot analysis (top panel). p27 was immunoprecipitated, followed by immunoblot analysis with p27, pY88 and pY74 antibodies (bottom panel). % G0/G1 as determined by PI staining and FACS analysis (top panel, % G0/G1) Immunoprecipitation with IgG without the lysate served as a negative control. (FIG. 7B) Brk was immunoprecipitated using the C-terminal Brk antibody and recombinant p27 and ATP was added to perform an in vitro kinase assay. Immunoblotting was performed to probe for p27, Brk, pY88 and pY74. Lane 3: no recombinant p27 added, lane 4: IP with IgG negative control, lane 5: no immunoprecipitate added. (FIG. 7C and FIG. 7D) Lysates were subjected to immunoblot analysis with the N-terminal Brk antibody. (FIG. 7E) RNA was extracted from A and G0 cells, and q-RT PCR was performed to probe for Brk and ALT-Brk mRNA expression. The ratio of Alt Brk to Brk is plotted.

(FIG. 8A) Flag tagged WT p27 was incubated with increasing amount of Flag tagged Alt-Brk (lanes 5-7) in presence of equal amount of Brk. Lane 5: + equimolar Brk and Alt, lane 6: ++2.5× Alt, lane 7: +++5× Alt Immunoblot analysis was performed using Flag, pY88 and pY74 antibodies. (FIG. 8B) Alt-Brk expressing cells were plated on day 0. They were induced (+Tet) or uninduced (−Tet) on day 1 and cells were harvested on days 2, 3 and 4 Immunoblot analysis was performed using N-terminal Brk, C-terminal Brk, Rb, Ser780 pRb, Flag or Actin antibodies. (FIG. 8C) p27 was immunoprecipitated from induced (+) or un-induced (−) Alt Brk expressing cells and immunoblot analysis was performed with p27, pY88 and pY74 antibodies. (FIG. 8D) Alt Brk or TRE3G vector alone cells were treated with + or −Tet and cell counts were used to monitor proliferation. (FIG. 8E) Lysates from MCF7 Mock, WT, YF (constitutively active) or KM (catalytically inactive) were used in immunoblot analysis with the N-terminal Brk antibody (Alt Brk), C-terminal Brk (Brk), pY342 Brk (active Brk) and actin antibodies. (FIG. 8F) p27 was immunoprecipitated from MCF7 cells that were either contact arrested (G0), asynchronous (A), or serum starved with 1% and 0% serum for 48 h. Immunoblot analysis was performed to probe for p27, pY88 and pY74. IgG and Mv1Lu lysates served as a negative control. (FIG. 8G) Expression of WT or mutant p27s was induced by adding Tetracycline to the culture media. p27 was immunoprecipitated from cell lysates and probed for p27, pY88 and pY74 Immunoprecipitation with IgG served as a negative control.

(FIG. 9A) Cells were harvested and counted every two days, as a measure of proliferation. Proliferation is plotted as a percentage relative to that seen in the DMSO treated control. Drugs and media were replaced every two days. (FIG. 9B) Viability was measured by trypan blue staining, and plotted relative to viability seen in the DMSO treated control.

FIGS. 12A and 12B: FIG. 12A shows the SH3 domain of Brk (SEQ ID NO: 2) and Src (SEQ ID NO: 3) compared at the level of amino acids. 3D modeling of the SH3 domain structures based on PDB coordinates are included. FIG. 12B provides the Alt-Brk 134 amino acid sequence (SEQ ID NO: 17). The SH3 region is shaded and the alternatively spliced region is shown in blue. Mimetics of this sequence in both the SH3 domain region and the alternatively spliced region, comprising mutations or amino acid truncations are described further herein below.

FIG. 13A: MB231 cells. FIG. 13B: MCF7 cells. FIG. 13C: HCC1954 cells. After six hours, the media was removed and fresh NP free-media was added for 2 days. Proliferation rate and viability were then assessed. Proliferation rate was determined by performing cell counting and standardization against the NO FBS control set to 100%. Viability was performed by trypan blue staining with the NO FBS set to 100%. Empty liposome is the NP formulation without conjugated ALT peptide. NO treatment control is the proliferation rate of cells not treated with the experimental conditions.

MCF7 and MB 231 ALT IC50 values of ~500 ng/ml ALT
HCC1954 cells ALT IC50 value of ~250 ng/ml ALT
MCF7 (ER/PR+, Her2−), Palbociclib: high responder (IC50=200 nM)
MB 231 (TNBC): Palbociclib: moderate-responder (IC50=400 nM
HCC1954 (ER/PR−, Her2+) Palbociclib: non-responder (IC50>1000 nM)

Figure 14:
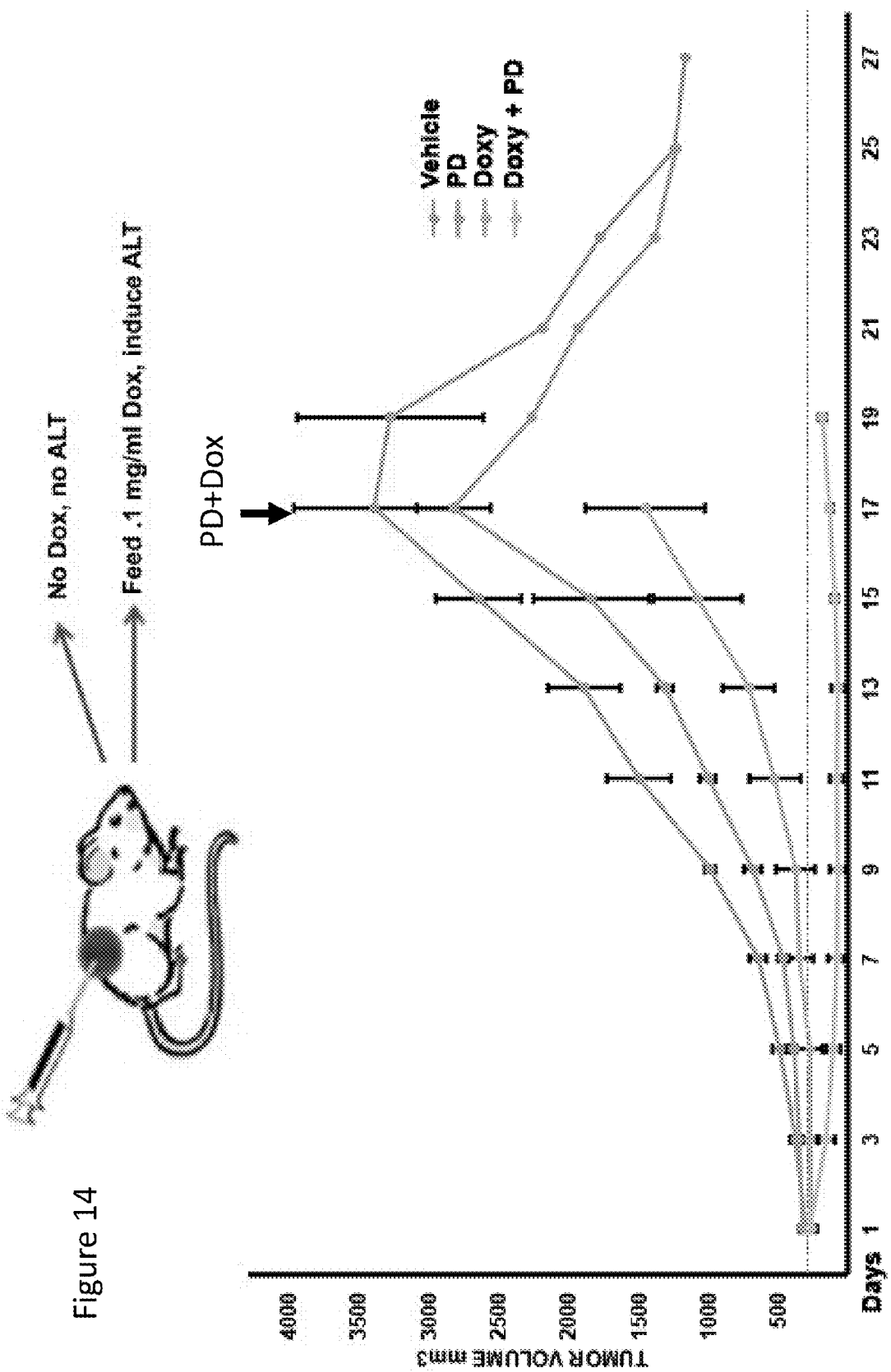

FIG. 14: ALT slows tumor growth in animals, and ALT and PD dual treatment causes tumor regression. MCF-7 inducible ALT cells were injected into the 4$^{th}$ mammary gland of NOD/SCID mice. Tumors were allowed to develop to a volume of 200 mm3, before treatment. Vehicle: daily gavage with PBS. PD: Daily gavage of Palbociclib 100 mg/kg. Doxy: 0.1 mg/ml doxycycline added to the drinking water to allow continuous uptake and induction of ALT in the human cancer cells. Doxy+PD: Daily gavage of Palbociclib 100 mg/kg and 0.1 mg/ml doxycycline added to the drinking water. Vehicle treated animals rapidly progressed and by 17 days, tumor volumes were >3000 mm PD treatment slowed down tumor growth but by day 17, tumors were >2500. Doxy (ALT induction) significantly slowed down tumor growth and by day 17, tumors were ~1500 mm3. However, dual ALT and PD (doxy/PD) treatment, caused tumor regression by >10% (e.g., from 200 mm3 down to 0-40 mm3), by day 5, which was durable up to day 19. At day 17, one vehicle and PD treated animals were treated with the dual Doxy/PD treatment and immediate tumor regression was seen and by day 27, tumors had decreased in volume by half.

FIGS. 15A-15C: ALT and PD treatment increases senescence, a clinical goal. FIG. 15A: MCF7-ALT cells were treated with IC100 concentration of Palbociclib (PD) or doxycycline to induce ALT. Drugs were replenished every two days and proliferation was determined by cell counting as indicated. Proliferation rates were standardized to the rate of proliferation seen in DMSO treated cells (control). PD treated cells were arrested for 10 days, before escape (proliferation) was detected. ALT expressing cells were arrested for 18 days before escape (proliferation) was detected. ALT expressing and PD treated cells were arrested for 30 days, with no escape detected. FIG. 15B: Cells were treated with drug combinations for 6 days, drug was removed and cells were replated in fresh drug free media. Proliferation was assessed by counting. DMSO, PD, and ALT expressing cells started to proliferate. Proliferation of ALT expressing and PD treated cells were delayed due to the growth arrest of those cells. However, the dual ALT expressing, PD treated cells never regained proliferation. Viability was measured by trypan blue staining and the ALT expressing, PD treated cells that weren't growing were viable. FIG. 15C: Cells were stained for the presence of beta-galactosidase, a marker of senescence. Beta-galactosidase was increased in the dual treated cells.

DETAILED DESCRIPTION OF THE INVENTION

Cyclin D and cdk4 are overexpressed in a variety of tumors, but their levels are not accurate indicators of oncogenic activity because an accessory factor, such as p27Kip1, is required to assemble this unstable dimer. Additionally, tyrosine (Y) phosphorylation of p27 (pY88) is required to cause a conformational change in the cyclin D-cdk4-p27 ternary complex, which activates cdk4 kinase activity. Thus, p27 pY acts as a cdk4 ON/OFF "switch." We identified two SH3 recruitment domains within p27 that modulate pY88, thereby modulating cdk4 activity. Via an SH3:PxxP interaction screen, we identified Brk (Breast Tumor Kinase, also called PTK6 or protein tyrosine kinase 6) as a high-affinity p27 kinase. Modulation of Brk in breast cancer cells modulates pY88 and increases resistance to the cdk4 inhibitor, PD0332991 (Palbociclib). An ALTternatively-spliced form of Brk (Alt-Brk SEQ ID NO: 17), which contains its SH3 domain, blocks pY88 and acts as an endogenous cdk4 inhibitor, identifying a targetable regulatory region within p27. Brk is overexpressed in 60% of breast carcinomas, suggesting that this facilitates cell cycle progression by modulating cdk4 through p27 Y phosphorylation. p27 has been considered a tumor suppressor, but our data strengthen the idea that it should also be considered an oncogene, responsible for cyclin D-cdk4 activity. Phosphorylation of Tyr-88/Tyr-89 in the 310 helix of p27 reduces its cyclin-dependent kinase (CDK) inhibitory activity. This modification does not affect the interaction of p27 with cyclin-CDK complexes but does interfere with van der Waals and hydrogen bond contacts between p27 and amino acids in the catalytic cleft of the CDK. This causes a conformational change in the p27-cyclin D-cdk4 complex, permitting p27 to vacate the catalytic cleft to allow ATP access and further phosphorylation of the active site. Thus, it had been suggested that phosphorylation of this site could switch the tumor-suppressive CDK inhibitory activity to an oncogenic activity.

Blocking cdk4 activity has long been a goal in cancer therapy. However, this has proven difficult due to the conservation between the active sites of serine/threonine kinases. Most inhibitors reacted with too many other essential kinases to provide any therapeutic benefit. Palbociclib is a new cdk4 inhibitor, currently in clinical trials for multiple myeloma and breast cancer, that appears to be extremely specific for cdk4 activity. The advantage of targeting p27 tyrosine (Y) phosphorylation as an indirect way to target cdk4 activity is that p27 has few substrates and as such its targeting should be more specific. Additionally, use of Palbociclib has shown that targeting cdk4 is a valid approach. The p27 Y phosphorylation mimetic provides an additional approach for targeting this important kinase, which may have additional benefits.

I. Definitions

A "therapeutically effective amount" of a compound or a pharmaceutical composition refers to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers useful in the methods of the present invention are described in "Remington's Pharmaceutical Sciences" by E. W. Martin.

"Concurrently" means (1) simultaneously in time, or (2) at different times during the course of a common treatment schedule.

"Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

II. Therapy for the Treatment of Cancer

The present invention also provides pharmaceutical compositions comprising at least one agent, wherein the at least one agent is a compound which interferes with the interaction between p27Kip1 and Brk and inhibits the phosphorylation event that turns p27 "on" in a pharmaceutically acceptable carrier. Such a pharmaceutical composition may be administered, in a therapeutically effective amount, to a patient in need of cancer treatment.

p27 Mimetics

Small molecule mimetics of peptide domains are known. For example, venclexta is a mimetic that functions as a BH3 domain of Bcl2 which inhibits Bcl2 action. In a similar fashion, the present invention provides p27 mimetics. In one aspect, the present invention provides a peptide comprising a sequence as disclosed herein, or a derivative, active portion, analogue, variant or mimetic, and uses thereof. Thus, in one embodiment, the present invention provides a mimetic of the K1-containing peptide of p27 or an SH3-containing peptide of Brk shown in FIG. 1. In preferred embodiments, the SH3 containing peptide is used. In some embodiments, the mimetic is a functional mimetic or a structural mimetic. In some embodiments, the mimetic is mimetic of one or both peptides. In some embodiments, the three-dimensional structure of said p27 mimetic is similar to that of the native peptide(s).

The present invention comprises variant peptides in which individual amino acids can be substituted by other amino acids that are closely related as is understood in the art. For example, individual amino acid may be substituted as follows: any hydrophobic aliphatic amino acid may be substituted in place of any other hydrophobic aliphatic amino acid; any hydrophobic aromatic amino acid may be substituted in place of any other hydrophobic aromatic amino acid; any neutral amino acid with a polar side chain may be substituted in place of any other neutral amino acid with a polar side chain; an acidic amino acid may be substituted in place of an acidic amino acid; and a basic amino acid may be substituted in place of a basic amino acid. As used herein, "mimetic", "functional/structural mimetic" relate to peptide variants or organic compounds having the same functional/structural activity as the polypeptide disclosed herein. Examples of such mimetic or analogues include chemical compounds or peptides which are modeled to resemble the three-dimensional structure of the cdk4 modulating regions of p27 peptide regions disclosed herein.

Thus, as used herein, "mimetic of p27" can refer to a peptide variant, a fragment thereof, organic compound or small molecule, which has the same function/structure-activity of the cdk4 modulating domains within p27. When the "mimetic" is peptide variant, the length of its amino acid sequence is generally similar to that of the K1-containing peptide or an SH3-containing peptide in p27. Alternatively, such "mimetic" can be the peptide variants having a shorter length of the amino acid sequence.

Suitable mimetics or analogues can be generated by modeling techniques generally known in the art. This includes the design of "mimetics" which involves the study of the functional interactions and the design of compounds which contain functional groups arranged in such a manner that they could reproduce those interactions.

The design of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound/peptide having a given target property. Firstly, the particular parts of the compound/ peptide that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore". Once the pharmacophore has been found, its structure is modeled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modeling process. In a variant of this approach, the three-dimensional structure of the ligand and its binding partner are modeled. This can be especially useful where the ligand and/or binding partner change conformation on binding, allowing the model to take account of the design of the mimetic A template molecule is then selected onto which chemical groups which mimic the pharmacophore can be grafted. The template molecule and the chemical groups grafted on to it can conveniently be selected so that the mimetic is easy to synthesize, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimization or modification can then be carried out to arrive at one or more final mimetics for in vivo or clinical testing.

Alt-Brk Mimetics

Brk, also known as PTK6, has been identified as a pharmaceutical target in breast cancer cells. An alternative splice variant of Brk, Alt-Brk, which lacks expression of exon 2 and encodes a shorter 15 KD protein, has also been observed in the breast cancer cell lines, MCF7 and T47D, and in several prostate and colon cancer cell lines (37, 38). Alt-Brk shares the N-terminal SH3 domain with Brk, has a unique proline rich carboxy terminus, but lacks the catalytically active SH1 kinase domain. The sequence of Alt-Brk is provided in FIG. 13.

We have identified the SH3 domain of Brk as having high affinity binding to p27, via the K1 site. This information enables the generation of binding models of Brk SH3:p27 by docking p27 and/or the K1 site of p27 (residues 90-100: RPPRPPKGACK; (SEQ ID NO: 5 and/or SEQ ID NO: 14). The sequence encoding the Brk SH3 domain in Alt-Brk or the full length alternatively spliced peptide (FIG. 13; SEQ ID NO: 2 or SEQ ID NO: 17) can be modified, (e.g., truncated by 1, 2, 3, 4, amino acids or mutated by 1, 2, 3, 4, amino acids) thereby enhancing its binding affinity, selectivity and cell permeability. The alternatively spliced region shown in blue of Alt-Brk in FIG. 13B could also be modified to improve anticancer activity. Such modifications include for example, truncation of 1, 2, 3, 5, 10 or more amino acids, replacement of amino acids with non naturally occurring amino acids, and the like.

The availability of the sequence information for Alt-Brk enables production of functional mimetics in which individual amino acids can be substituted by other amino acids that are closely related as is understood in the art. For example, individual amino acid may be substituted as follows: any hydrophobic aliphatic amino acid may be substituted in place of any other hydrophobic aliphatic amino acid; any hydrophobic aromatic amino acid may be substituted in place of any other hydrophobic aromatic amino acid; any neutral amino acid with a polar side chain may be substituted in place of any other neutral amino acid with a polar side chain; an acidic amino acid may be substituted in place of an acidic amino acid; and a basic amino acid may be substituted in place of a basic amino acid. As used herein, "mimetic", "functional/structural mimetic" relate to peptide variants or organic compounds having the same or improved functional/structural activity as the polypeptide disclosed herein.

Scaffolds will be produced to mimic key structural features of this domain. Scaffolds that can reproduce the important interactions between the SH3 domain and K1 sites should have efficacy for the treatment of proliferative disorders, particularly cancer. Scaffolds, include but are not limited to, RAFT-type scaffolds or beta barrel scaffolds (FN3). Non-natural amino acids can also be used to increase covalent interactions. Solid phase peptide synthesis in conjunction with solution phase organic synthesis can be employed to assemble the mimetics. Docking-guided Structure Activity Relationship (SAR) analysis can be used to further optimize scaffold size, points of functionalization and rigidity. Alternatively, the mimetic or the SH3 derivatives of the invention can be packaged in a lipoplex based nanoparticle for in vivo delivery The mimetics of the present invention may be used in a variety of treatment regimens for the treatment of malignant disease. Cancers that may be treated using the present protocol include, but are not limited to: cancers of the breast, brain, thyroid, prostate, colorectum, pancreas, cervix, stomach, endometrium, liver, bladder, ovary, testis, head, neck, skin (including melanoma and basal carcinoma), mesothelial lining, white blood cell (including lymphoma and leukemia), multiple myeloma, esophagus, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

III. Combinatorial Therapies for the Treatment of Cancer

In accordance with the present invention, it has also been discovered that the combination of the agents and mimetics described herein with certain known chemotherapeutically effective agents act synergistically to suppress tumor growth. Accordingly, the present invention provides a pharmaceutical composition for the treatment of cancer in a patient comprising at least one agent that interferes with specific tyrosine (Y) phosphorylation, thereby maintaining p27 in the "off" position and at least one chemotherapeutic agent in a pharmaceutically acceptable carrier. Also provided is a method for treating cancer in a patient by administering an effective amount of at least one phosphorylation inhibiting agent in combination with at least one chemotherapeutic agent. Suitable chemotherapeutic agents include, but are not limited to: palbociclib, ribociclib, abemaciclib, osirmetinib, gefitinib, lapatinib, pantitumumab, vandetanib, necitumumab, vemurafenib, sorafenib tosylate, PLX-4720, dabrafenib, paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, herceptin, vemurafenib, erlotininb, cetuximab, letrozole, fulvestrant and epothilone derivatives. Cancers that may be treated using the present combinatorial protocol include, but are not limited to those cancers set forth hereinabove.

IV. Administration of Pharmaceutical Compositions and Compounds

The pharmaceutical compositions of the present invention can be administered by any suitable route, for example, by injection, by oral, pulmonary, nasal or other methods of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. The mimetics may be operably linked to sequence tags that facilitate entry into cells by increasing cellular permeability. The molecules listed below are useful as carriers and/or as components of complex carriers for transporting the mimetics of the present invention into cells and into subcellular compartments where they can express their anti-cancer functions in a wide variety of cell types. Such peptides not only increase membrane penetration activity but they can also promote endosomolytic activity. These include, without limitation, TAT and TAT variants, MPG peptide, Penetratin, EB1, VP22, Model amphipathic peptide, Pep-1 and Pep-1 Related Peptides, Fusion sequence-based protein (FBP), Transportan and analogues such as TP-7, TP-9 and TP-10, Protamine and Protamine-fragment/SV40 peptides, Polyethylenimine (PEI), Poly-Lysine, Histidine-Lysine Peptides, Poly-Arginine, gp41 fusion sequence. Other suitable sequence tags are described in Gilad et al. Biomedicines 4: 11 (2016), doi: 10.3390, which is incorporated herein by reference. As mentioned, the mimetics may be present within liposomes or complexed with nanoparticles to enhance in vivo delivery. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized). Particular methods of administering pharmaceutical compositions are described hereinabove.

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity of the site of inappropriate immune activation or a tumor. Other controlled release systems are discussed in the review by Langer (Science (1990) 249:1527-1533).

The following materials and methods are provided to facilitate the practice of the present invention.

Antibodies.

Figures 2A, 2B, 2C, 2D, 2E, 2F:
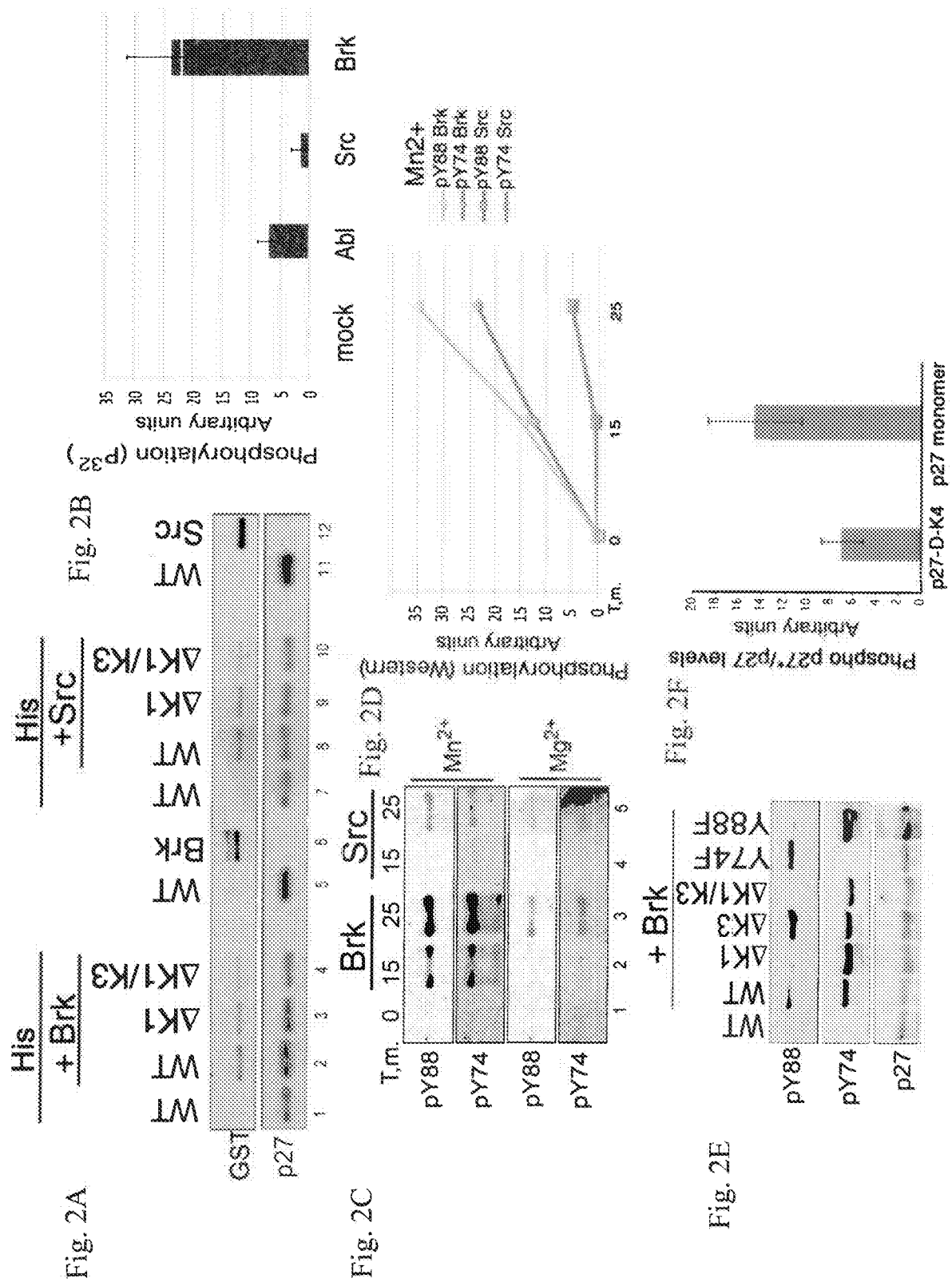

Mouse Anti-p27(Kip1), BD Biosciences 610242. Cdk4 (DCS-35), p27 (N-20), C-terminal Brk (C-18), Brk (D-6), N-terminal Brk (N-20), c-Src (SC-18), Cyclin D1 (H 295), ARHGDIA (A-20), Santa Cruz Biotechnology. Anti-beta galactosidase antibody is from RND systems (af6464). Phosphotyrosine (P-Tyr-100), Cell Signaling Technology. Cdk4 (C-term, Cat. No. AP7520b), Abgent. GST (PRB-112C), Covance. Flag (F3165), Actin (A2066), Sigma Aldrich. Phospho Brk (Tyr342), EMD Millipore. pY74, Y88 and Y89 phospho-specific antibodies were generated by immunization of rabbits with phosphor-specific p27 peptides (Invitrogen). Negative- and positive-affinity chromatography with non-phosphorylated and phosphorylated peptides respectively, were performed to purify the antibodies. The antibodies are specific only for Y88, Y89, Y74 phosphorylation respectively (FIG. 2B, data not shown).

Enzymes.

Gst-PTK6/Brk, GST-Src (SignalChem), His-Abl (New England Biolabs), His-PTK6/Brk, His-Src (Invitrogen) were used according to manufacturer's specifications. Enzymes had approximately equivalent specific activities.

Phage-ELISA.

Phage supernatants were generated and binding of SH3-phages to recombinantly produced His-tagged-p27 or GST-PxxP-peptides was analyzed as described (28).

Construction of Mutants and Peptides.

Oligonucleotides encoding the PxxP-peptides K1, K2 and K3 were annealed and directly ligated into pGEX-KG expression vector for production of N-terminally GST-tagged peptides. GST, GST-Brk SH3, GST-Brk SH2 expressing plasmids were described (57). E. coli BL21 cells transformed with these plasmids were grown in LB-ampicillin until an OD of 0.6 was reached and protein production was induced by addition of 1 mM IPTG. After 2 hours, cells were harvested by centrifugation. Cell lysis and protein purification on GST-sepharose was carried out according to the GST-protein purification manual (GE Healthcare). Protein was eluted with an excess of glutathione and dialysed against PBS for further use Purified, C-terminal histidine-tagged or N-terminal Flag tagged p27's were generated from E. coli as described previously (12). Human p27 cDNA was used as a template in PCR-mutagenesis with oligonucleotides carrying the point mutations: PPPP91,92,94, 95AAAA (ΔK1); PKKP188,189,190,191AAAA (ΔK3); or PPPP91,92,94, 95AAAA and PKKP188,189,190, 191AAAA (ΔK1/K3).

Oligonucleotides Used to Generate 58-106 were:

```
Forward primer
                                        (SEQ ID NO: 6)
5'-GGCCTCGAGCTAGCTCTCCTGCGCCG-3'

Reverse primer
                                        (SEQ ID NO: 7)
5'GGGGTCTAGAGCCACCATGGACTACAAGGACGACGATGACAAGCGCAA

GTGGA ATTTCGATTTTC-3'
```

The PCR fragments were ligated to the T7pGEMEX human His-p27 or T7pGEMEX human Flag-p27 plasmid for expression in E. coli. Mutants Y74F, Y88F, and Y88/89F were previously described (12). Flag-tagged p27 mutants were purified by Flag-immunoprecipitation with Flag antibody (M-2, Sigma F-18C9) and eluted with Flag peptide (Sigma F-4799) according to manufacturer's protocol. His-tagged p27 mutants were purified by FPLC via his-trap affinity chromatography (His-Trap HP, GE Healthcare 71-5247-01). The affinity column was stripped according to manufacturer's protocol, then washed with 5 column volumes of 100 mM $CoCl_2$. The crude material was applied with a loading buffer consisting of 6 M urea, 500 mM NaCl, 50 mM Tris-HCl, pH 7.5 and 20% glycerol. The material was washed with 500 mM NaCl, 50 mMTris-HCl, pH 7.5 and 10% glycerol. The purified material was eluted with 500 mM imidazole, 20 mM Hepes pH 7.4 and 1 M KCl. The protein was then dialyzed overnight in a solution of 25 mM Hepes pH 7.7, 150 mM NaCl, 5 mM MgCl2 and 0.05% NP40. All purified proteins were analyzed by Coomassie and immunoblot analysis. The p27, ΔK1, ΔK3, ΔK1/K3, Y74F, and Y88/89F cassettes were cloned into the pTRE3G tetracycline inducible retroviral expression construct using the In Fusion Gene Cloning kit (Clontech). Alt Brk was generated by PCR using human Alt-Brk in PCDNA3 vector (38) as a template, followed by cloning into the T7pGEMEXhuman Flag-tagged plasmid and pTRE3G using the In-fusion cloning kit.

Recombinant Cyclin D1-Cdk4.

Recombinant His-cyclin D1-cdk4 was harvested from co-infected High5 cells and purified as described previously (12). Recombinant GST-Rb (86 Kdversion) was purified and used in in vitro kinase assays as previously described (12).

In Vitro Phosphorylation of the p27-Cyclin D1-Cdk4 Ternary Complex.

Recombinant His-p27 and mutants were incubated for one hour at room temperature with Cyclin D1-Cdk4 in 25 mM Hepes, pH 7.4. This ternary complex was immunoprecipitated with anti-Cdk4 antibodies (Santa Cruz, DCS 35) and Protein G Dynabeads (Invitrogen, 10004D). The complex was then subjected to SFK phosphorylation and/or used in in vitro Rb kinase assays.

Cell Lines.

MCF10A, MCF7, MDA MB 231, MDA MB 468, T47D, PC3, Mv1Lu, HCC1954, and HEK 293 were purchased from ATCC and maintained according to vendor's instructions. Insulin levels were adjusted to 0 (−), 10 (+) or 50 (+++) µg/ml and cells were grown for 2 weeks before being assayed as described. To arrest by contact, cells were grown to confluence and maintained for 6 days, replenishing the media every other day. Immunoprecipitation, immunofluorescence, PI staining were performed as described in materials and methods section. FACS analysis was performed as described (56). Cells were counted using the automated cell counter (BioRad TC-20). Viability was measured by Trypan Blue staining and counted using the cell counter.

Immunoprecipitation.

Cells were either lysed with Triton lysis buffer (25 mM HEPES pH 7.4, 100 mM NaCl, 1 mM EDTA, 10% Glycerol, 1% Triton X-100) or Tween lysis buffer (50 mM HEPES pH 7.4, 150 mM NaCl, 1 mM EDTA, 2.5 mM EGTA, 10% Glycerol, 0.1% Tween-20). The lysis buffers were supplemented with 1 mM PMSF, 10 mM DTT, 1 mM NaV, 10 ng/ml Leupeptin and 1ng/ml Aprotinin. Lysates (1 mg) were pre-cleared by incubation with Dynabeads A or G (Life Technologies) for 1 h at 4° C. Immunoprecipitations proceeded as described (12).

Immunofluorescence.

Cell lines were split on day 0 into sub-confluent conditions and fixed on day 2 in microwell plates using 4% paraformaldehyde in 1xPBS, pH 7.4, for 15 min at room temperature. They were permeabilized with 0.1% Triton X-100 and blocked with 5% BSA for 1 h at room temperature. They were incubated with the first round of primary antibodies in PBS for 1 hour at room temperature. The cells were washed with PBS and incubated with appropriate secondary antibodies (1:500), diluted in 3% BSA/PBS, for 1 hour at room temperature. They were then washed with PBS and incubated with 0.02% Triton X-100/3% BSA for 30 min at room temperature to prepare them for a second round of incubation with antibodies. Cells were then washed with PBS and incubated with Hoechst stain (1 mg/ml) 1:5000 in PBS for 15 min at room temperature. They were rinsed with water and mounted on a slide with 90% gylcerol. Samples were incubated at 4° C. before they were analyzed by confocal microscopy.

Rb In Vitro Kinase Assay:

Cdk4 associated complexes were immunoprecipitated as described. Recombinant Rb was added to the immunoprecipitates in presence of the kinase buffer (50 mM, HEPES pH7.4, 10 mM $MgCl_2$, 1 mM DTT, 2 mM EGTA, 3 mM β-Glycero-phosphatase, 100 µM ATP), incubated for 30 min before SDS-PAGE electrophoresis. Immunoblot analysis was performed to probe for cdk4, Rb and pRb-Ser780.

Inhibitor Treatment.

Cells were seeded on six well plates in duplicate, $5.0 \times 10^4$ per well. 24 h. post seeding, one well for each plate was treated with trypsin and counted using the Biorad Automated cell counter. 48 hours post seeding, another well was treated with trypsin and counted and the rest of the wells were treated with PD0332991 (SelleckChem) at 50 nM, 100 nM, 200 nM and 400 nM. DMSO was used as a negative control. Cells were counted again 24 and 48 h post treatment. The IC50 values were determined by normalizing the number of viable cells treated with different concentrations of PD to the number of viable cells treated with DMSO for each cell line 48 hours post treatment. The number of viable cells treated with DMSO was considered 100%. The log of the viability values was obtained and the data was fitted to a nonlinear regression curve, which was used to generate the IC50 values using Graphpad Prism software.

Brk Knockdown.

Lentiviral siRNA particles were purchased from Sigma Aldrich: NM_005975.2-1064sc1 and NM_004383.x-2117s1c1. MCF7 cells were plated on day 0, on day 1, the media was aspirated and the cells were infected with the siRNA lentiviral particles. Hexadimethrine bromide was used according to manufacturer's instructions to enhance the infection efficiency. Cells were incubated overnight, media was replenished on day 2 and the cells were incubated for 72 hrs, fixed with 4% Paraformaldehyde and immunofluorescence was performed as described.

Packaging Alt-Brk into Nanoparticles.

To package ALT in NPs, we first generated empty NPs using ethanol injection method. Briefly, the lipids mixture in ethanol that consists of DOTMA (1,2-di-O-octadecenyl-3-trimethyl ammonium propane (chloride salt), cholesterol, and D-α-tocopheryl polyethylene glycol 1000 succinate (TPGS) at DOTMA:Cholesterol:TPGS molar ratio of 49.5:49.5:1 was quickly injected into HEPES buffer (pH=7.4) to achieve 10% ethanol and 90% aqueous in the final mixture, and the empty NP were thus formed. We then mixed empty NP with ALT at lipids to ALT mass ratio of 20:1 or 10:1 to generate NP-ALT. See Wu, Y., et al., Mol Ther Nucleic Acids, 2013. 2: p. e84 and Wu, Y., et al., Surface-mediated nucleic acid delivery by lipoplexes prepared in microwell arrays. Small, 2013. 9(13): p. 2358-67.

NP-ALT was added to cell media in the absence of fetal bovine serum for 6 hours. This media was removed and replaced with FBS+ media, and cells were allowed to recover for 2 days, at which time, cell counts were determined Counts were standardized to the proliferation seen in the NO FBS untreated control.

Expression In Vivo.

Generation of the WT-Brk, KM-Brk, and YF-Brk has been described (32) Amphotropic retroviruses were generated by transfection using Lipofectamine 2000 (Life Technologies 11668-019) of HEK 293 cells with pAmpho envelope and pBabe or pTRE3G tetracycline inducible constructs. Following viral infection of MCF7 cells, stable integrants were isolated by puromycin selection. Colonies were pooled to generate stable, puromycin resistant clones. Stable expression was verified by immunoblot and immunofluorescence analysis. Tetracycline inducible expression was achieved by the addition of TetExpress (Clontech) to the media.

Mouse Xenograft Model.

Female NOD/SCID 8 week old mice were injected with MCF7-ALT cells in the 4th mammary gland. Tumors were allowed to develop to a volume of 200 mm3, before treatment. Tumor volume was monitored every other day using digital calipers. Vehicle: daily gavage with PBS. PD: Daily gavage of Palbociclib 100 mg/kg. Doxy: 0.1 mg/ml doxycycline added to the drinking water to allow continuous uptake and induction of ALT in the human cancer cells. Doxy+PD: Daily gavage of Palbociclib 100 mg/kg and 0.1 mg/ml doxycycline added to the drinking water.

Quantitative RT-PCR.

RNA extraction was performed using TRIzol reagent (Life Technologies) as directed by the manufacturer's instructions. 500 μg of RNA was subjected to reverse transcription using the Verso cDNA kit (Thermo Scientific). 250 ng RNA was mixed with cDNA primers and ABsolute Blue qPCR SYBR Green (Thermo Scientific) to perform qPCR.

Following Primers were Used to Perform q-PCR:

Statistics.

The statistical analysis was performed using the Student's t test, Welch's t test, 2 tailed type 3 test, due to unequal sample sizes with unequal variances.

The following example is provided to illustrate certain embodiments of the invention. It is not intended to limit the invention in any way.

Example I

Figure 1A:
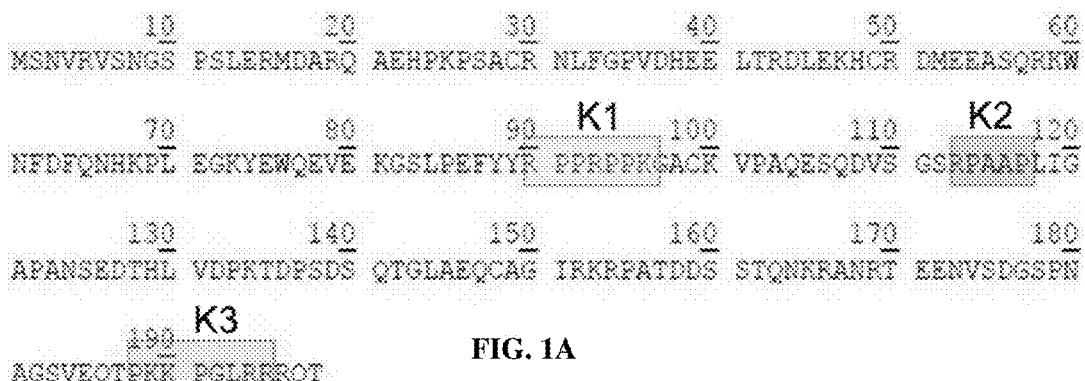
FIGS. 1A-1C: Brk binds to p27 with high affinity in vitro.

Brk Phosphorylates p27 In Vitro p27 contains three putative SH3 recruitment sequences that contain the common PxxP core motif, designated K1, K2 and K3 (FIG. 1A). K1 contains a basic residue after the PxxP, thus qualifying it as a canonical type 2K SH3 target site (27). K2 is only present in the human orthologue of p27 and thus is unlikely to mediate conserved functions in cell cycle control. K3 is at the C-terminus of p27, in a region that has shown to be dispensible for cdk interaction (15). Based on the reported interactions of p27 with non-receptor bound tyrosine kinases (SFKs), such as Src, Yes, and Lyn, we asked whether other members of the family might also interact with p27, and which recruitment sequences (K1, K2, and/or K3) are used. We tested 11 members of the SFK family as well as Abl, which has been reported to phosphorylate p27 in vitro and in vivo, for binding to either full-length p27, or GST-tagged K1, K2 or K3 peptides, using a phage-ELISA procedure (28) (FIG. 1B, C).

Figure 1B:
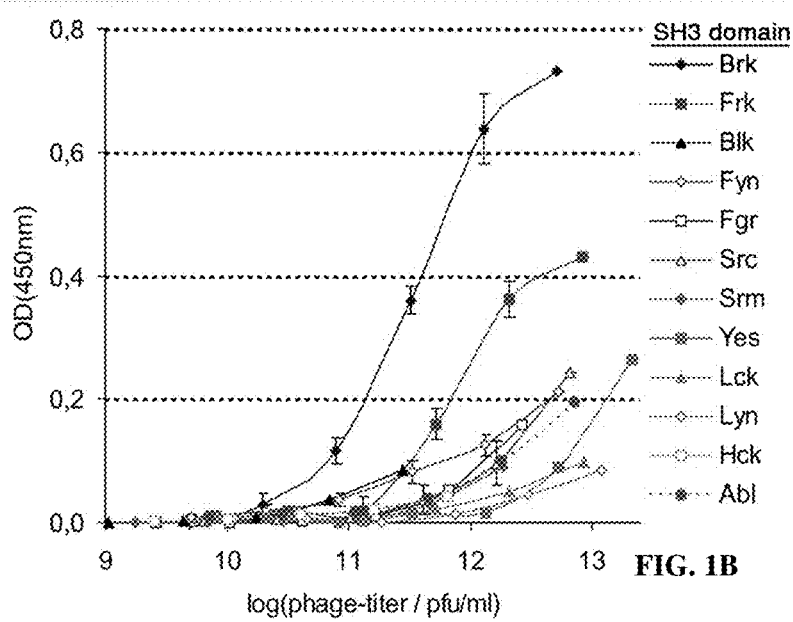
Figure 1C:
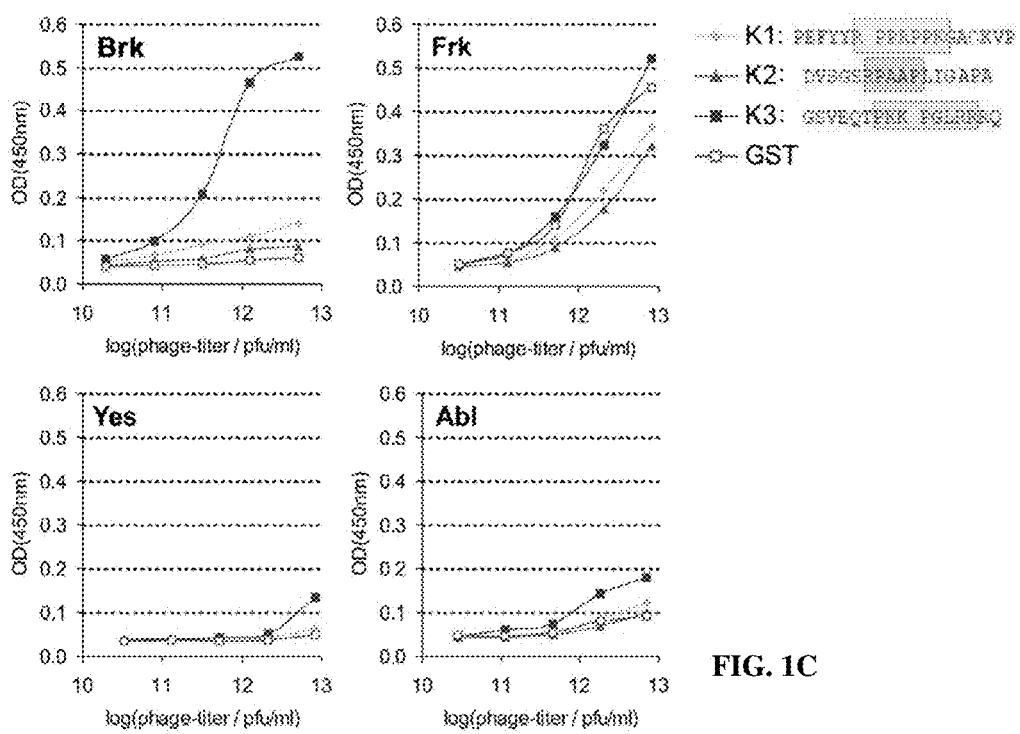

While the SH3 domains of most SFKs could interact with full-length p27, we found that the SH3 domain of Brk interacted strongly with full-length p27 (Kd=250 nM), and associated better than either Src or Abl, two SFKs known to interact with p27 (FIG. 1B). This Kd value is reflective of the interaction between p27 and the phages, which contain many identical reiterated SH3 domains, which would enhance binding. We expressed the individual SH3 recruitment sites within p27 (K1, K2 and K3) as GST-fusion peptides and tested them against the SH3 domain library (FIG. 1C). The GST domain expressed in the absence of any p27 sequence was used as a negative binding control (GST). Most SFK SH3 domains were not able to interact significantly with the individual PxxP-containing peptides (data not shown). Brk, however, interacted strongly with the K3 region, and weakly with the K1 region (FIG. 1C). The related kinase, Frk, was the second best binder to full length p27 (FIG. 1B), but when tested against the individual PxxP domains, significant binding to the GST negative control was detected (FIG. 1C), so we could not conclude whether Frk's SH3 domain bound to the PxxP domain peptides. The SH3 domains of Abl and Yes interacted with the K3 domain of p27, although this interaction was reduced when compared to that of Brk (FIG. 1C). No SH3 domains interacted with the K2 site (FIG. 1C).

To determine whether full length Brk could interact with p27, we incubated GST-Brk or GST-Src with recombinant

| GENE | FORWARD PRIMER | REVERSE PRIMER |
|---|---|---|
| Actin | 5'-AAAATCTGGCACCACACCTTCTAC-3' *(8) | 5'-TAGCACAGCCTGGATAGCAACG-3' (9) |
| Brk | 5'-CCAAGTATGTGGGCCTCTGG-3' (10) | 5'-AAAGAACCACGGTTCCGACT-3' (11) |
| Alt Brk | 5'-GACGGTGGAGTCGGAACCTG-3' (12) | 5'-TAGTTCACAAGCTCGGGCAG-3' (13) |

*numbers in parentheses are SEQ ID NOS:

His-p27. p27-associated complexes were isolated by metal agarose chromatography (HIS) and then assayed for p27-associated Brk or Src by immunoblot analysis using GST antibodies (FIG. 2A). In the context of the full length enzyme, both GST-Brk and GST-Src associated to a similar extent with p27, suggesting that additional contacts present outside the SH3 domain might increase affinity.

To determine whether Brk's interaction with p27 led to phosphorylation, we incubated recombinant p27 with purified Brk in the presence of [γ-$^{32}$P]ATP (FIG. 2B). We included Abl and Src, as they have been shown to phosphorylate p27 in vitro. Consistent with Brk's high-affinity interaction with p27, we found that Brk phosphorylated p27 approximately 4 fold better than Abl, and 8 fold better than Src (FIG. 2B), suggesting an increased specific activity towards this substrate. We additionally verified this using our p27 pY88 phospho-specific antibody (pY88) and our Y74 phospho-specific antibody (pY74) (FIG. 2C, D). These antibodies recognize Y88 or Y74 phosphorylation in vitro and in vivo and do not recognize phosphorylation on mutants Y88F or Y74F respectively (FIG. 2E, lanes 6, 7) (14). We incubated full length p27 with Src or Brk in the presence of ATP and either $MgCl_2$ or $MnCl_2$. In the presence of both cations, Brk phosphorylated p27 on both residues more efficiently (FIG. 2C, D). Brk also phosphorylated the adjacent residue Y89 in vitro (data not shown), but we focused on Y88 phosphorylation in the rest of this study.

The K1 Site is Essential for Brk's Phosphorylation of p27 Y88 and Activation of the Cyclin D-Cdk4 Complex To determine whether Brk's phosphorylation of p27 was mediated through the K1 or K3 sites, we mutated the prolines in these domains to alanines, to generate recombinant His-tagged mutants, ΔK1 and ΔK3. Mutant ΔK1/K3 has lost both sites. All of these mutants contain an intact K2 site, which did not appear to associate with Brk in the interaction screen (FIG. 1). We incubated full length GST-Brk or GST-Src with mutants ΔK1 and ΔK1/K3, and isolated complexes by metal agarose chromatography (HIS), as described above (FIG. 2A). The association of mutants ΔK1 or ΔK1/K3 with Brk was reduced but still detectable (FIG. 2A, lanes 3, 4, 9, 10), again suggesting that additional contacts outside the PxxP region mediated the full p27: Brk interaction. The GST-tagged Brk does not associate with the metal agarose chromatography beads (FIG. 3, lane 6).

We then probed these mutants for phosphorylation using the pY88 and pY74 antibodies (FIG. 2E). We did not observe Y88 phosphorylation in the ΔK1 and ΔK1/K3 mutants (FIG. 2E, lanes 3, 5), suggesting that an intact K1 site was necessary for efficient Y88 phosphorylation. pY88 was detected in the ΔK3 mutant, demonstrating a requirement for the K1 site, rather than the K3 site, in this assay. When the GST-SH3 domain of Brk was used in the Phage-Elisa assay (FIG. 1), the K3 peptide bound preferentially, suggesting that in the context of the full length Brk protein additional contacts increase the K1:Brk affinity. When probed with the pY74 antibody, all of the mutants, with the exception of Y74F, were still phosphorylated (FIG. 2E). The phosphorylation of residues Y88 or Y74 appears to occur independently, as the singly mutated variants (Y88F and Y74F) were still phosphorylated on the intact sites respectively (FIG. 2E, lanes 6, 7). This data suggested that interaction of the K1 site with Brk is required for Y88 phosphorylation, but phosphorylation of Y74 is K1 and K3 independent (FIG. 2E).

In vivo, p27 is not detected as a monomer, but rather appears to be complexed with cyclin-cdk complexes (12). To determine whether Brk could phosphorylate p27 when bound to cyclin D-cdk4, p27-cyclin D-cdk4 ternary complexes were generated by incubation with recombinant components and isolated by immune-precipitation with cdk4 antibodies (FIG. 2F, 2G). Cyclin D-cdk4-p27 ternary complexes and monomeric p27 were then incubated with Brk and (γ-$P^{32}$) ATP, and total Y phosphorylation was monitored by autoradiography (p27*) (FIG. 2F). An approximate 3-fold reduction in phosphorylation was seen when p27 was associated with cdk4. A similar experiment was performed with the p27 mutants, isolating p27-cyclin D-cdk4 ternary complexes by cdk4 immunoprecipitation (FIG. 2G, lane 1-4) and monomeric p27 (FIG. 2F, lanes 7-10), followed by Brk and ATP incubation and immunoblot analysis with pY88 antibodies. When both monomeric and cdk4-associated p27s were assayed, phosphorylation was not detected in mutants ΔK1, ΔK1/K3 and Y88F (FIG. 2F, lanes 1, 3, 4, 7, 9, 10). Mutant Y74F was phosphorylated both as a monomer (FIG. 2F, lane 8) as well as when associated with cdk4 (FIG. 2F, lane 2), and pY88 was reduced approximately 3-fold. Thus, Brk can still phosphorylate p27 when presented in more physiological p27-cyclin D-cdk4 ternary complexes.

We and others have shown that loss of Y88 phosphorylation converts p27 into a cdk4 inhibitor in vitro and in vivo (12, 14), effectively locking the p27-cyclin D-cdk4 ternary complex into a closed conformation, preventing both CAK phosphorylation of cdk4 and ATP access to the catalytic site. Our data predicted that loss of the K1 site, which causes loss of pY88 phosphorylation, should also convert p27 into a cdk4 inhibitor. Therefore, we tested the ability of WT and p27 mutants to inhibit recombinant cyclin D-cdk4 in in vitro kinase assays, using recombinant Rb as a substrate (FIG. 2H, 2I). We found that while Cyclin D-cdk4 phosphorylates Rb, this phosphorylation can be inhibited by increasing concentrations of non-phosphorylated p27 or alternatively, the specific activity of the complex is increased by Y88 phosphorylated p27 (FIG. 2H). WT or p27 mutants were not phosphorylated (FIG. 2I, lane 1-4) or were phosphorylated with Brk (FIG. 2I, lane 6-9) and then were mixed with cyclin D-cdk4. Recombinant Rb was added in the presence of [γ-$^{32}$P]ATP and phosphorylation was monitored by autoradiography (FIG. 2I, Rb*). In this experiment, we used a low concentration of cyclin D-cdk4 that did not give detectable Rb phosphorylation (FIG. 2I, lane 5). In the absence of Brk phosphorylation, the addition of the WT and the p27 mutants still did not permit detectable cyclin D-cdk4 activity (FIG. 2I, lanes 1-4). The addition of the phosphorylated WT to cyclin D-cdk4, however, restored Rb kinase activity (FIG. 2I, lane 6), suggesting that it converted cyclinD-cdk4 into an active conformation and increased the specific activity of this complex. However, all of the other mutants, which were not phosphorylated on all residues, still inhibited cyclin D-cdk4 activity (FIG. 2I, lanes 7-9). As expected, mutants ΔK1 and Y88/89F, which lacked Y88 phosphorylation, inhibited Rb kinase activity (FIG. 2I, lanes 7, 9). Mutant Y74F, which retained Y88 phosphorylation, also inhibited cyclin D-cdk4 activity (FIG. 2I, lane 8), suggesting that phosphorylation of both Y74 and Y88 is required to activate cyclin D-cdk4. To verify that the addition of phosphorylated p27 did not increase the assembly of residual, monomeric cyclin D and cdk4 components in the recombinant preparation, we immunoprecipitated cdk4 from the cyclin D-cdk4 and p27 incubations, and probed for cyclin D levels. We found that the same amount of complex was present in the presence or absence of phosphorylated p27 (FIG. 2I, lower panel). Thus, the K1 site was required for Brk's phosphorylation of Y88, and loss of this phosphorylation converts p27 into a cdk4 inhibitor in vitro.

The Isolated Brk SH3 Domain or an Isolated p27 K1 Peptide are Able to Block Brk's Phosphorylation of p27

It appeared that the SH3:PxxP interaction was required for Y88 phosphorylation. To verify this, we attempted to block this interaction by the addition of a Flagged tagged K1-site containing peptide, F58-106 (FIG. 3A) or the isolated SH3-domain (FIG. 3C) as a competitor in the p27:Brk interaction. Peptide F58-106 encompasses a portion of p27 (residues 58 to 106) that contains the K1 site only along with phosphorylation sites Y74 and Y88. While Brk phosphorylates p27 on both residues Y74 and Y88 (FIG. 3A, lane 3), it was only able to phosphorylate F58-106 on residue Y74 (FIG. 3A, lane 4), even though residue Y88 is intact in this peptide. When p27, Brk, and increasing amounts of the K1 site-containing competitor F58-106 were incubated together, phosphorylation on residue Y88 decreased (FIG. 3A, lanes 5-8). Y74 phosphorylation was only slightly reduced when the highest concentration of F58-106 was used (FIG. 3A, lanes 5-8).

To demonstrate that the K1-containing peptide, F58-106, could interact with Brk, we incubated GST-Brk with p27 and/or F58-106, followed by immunoprecipiation with GST antibodies and immunoblot analysis with GST and p27 antibodies (FIG. 3B). F58-106 interacted with GST-Brk (FIG. 3B, lanes 5,6), demonstrating that this K1-containing peptide was sufficient to associate with full length Brk. We then performed the converse reaction, and increasing amounts of individual recombinant, GST-tagged pieces of Brk (GST-SH2, GST-SH3) or GST peptides were incubated with p27 before the addition of full length Brk and ATP. The reactions were probed by immunoblot analysis with pY88 and pY74 antibodies (FIG. 3C). We found that the prior addition of GST-SH3 was sufficient to reduce Y88 and more slightly Y74 phosphorylation (FIG. 3C, lanes 3,4). The addition of the GST peptide (FIG. 3C, lanes 5,6) or the GST-SH2 peptide (FIG. 3C, lanes 7,8) did not reduce Y88 or Y74 phosphorylation (FIG. 3C, compare lanes 3, 5, 7), with the exception of when adding a 10 molar excess of GST (FIG. 3C, lane 6). p27 and GST immunoblot analysis was also performed, as a measure of the total protein amounts added to the reactions and does not represent their association.

We incubated the GST, GST-SH3, or GST-SH2 peptides with His-tagged versions of p27 and the ΔK1/K3 mutant, isolated complexes by metal agarose chromatography and performed immunoblot analysis with GST antibodies (FIG. 3D). The GST-SH3 peptide interacted with p27 in a K1/K3 dependent fashion: it bound to WT p27 but did not associate with ΔK1/K3 p27 (FIG. 3D, lanes 4, 5). We also found that the SH2 peptide bound to both WT p27 and ΔK1/K3 (FIG. 3D, lanes 2, 3), suggesting that Brk had a second binding site on p27. However, this binding was independent of the PxxP K1 site (FIG. 3D, lane 3). Because this experiment was performed in the absence of ATP, this SH2 domain recognizes p27 in an atypical phosphotyrosine-independent fashion. It is unclear where on p27 the SH2 domain associates and/or the significance of this interaction, but it explains the results from FIG. 2A, where we found that full-length Brk was still able to interact with mutant ΔK1/K3 in vitro (FIG. 2A, lane 4).

This data suggests that the SH3 domain binds to p27 in a K1 site dependent manner. The K1 site and the SH3 domain mediate p27 Y88 phosphorylation in vitro and blocking this interaction is sufficient to prevent Y88 phosphorylation. While the SH2 domain binds to p27 and may contribute to Brk's association with p27, it does not appear responsible or required for Brk's phosphorylation of Y88, which is mediated by the SH3 domain.

Brk Interacts with p27 In Vivo

While we found that Brk was a high-affinity kinase for p27, able to phosphorylate p27 in vitro, we wanted to demonstrate that this interaction was physiological. Brk was detected by immunoblot analysis with a C-terminal Brk antibody in several breast cancer cells (MDA MB 231 and MCF7) and in the normal mammary epithelial cell line, MCF10A (FIG. 4A). As reported by others, it was not detected in the breast cancer line, MDA MB 468 (29). To verify that Brk specifically interacted with p27 in vivo, we immunoprecipitated Brk and examined the immunoprecipitates for p27 association (FIG. 4B) or immunoprecipitated p27 and examined the immunoprecipitates for Brk association (FIG. 4C), demonstrating that this interaction could be seen in vivo under physiological conditions with endogenous proteins. Brk was not detected in p27 immunoprecipitates from MDA MB 468 cells, where endogenous Brk was not expressed (FIG. 4C, lane 4).

To demonstrate that the p27:Brk interaction in vivo was mediated through the PxxP motifs (K1 or K3) of p27, we expressed in MCF7 cells, in a tetracycline-inducible manner, Flag-tagged variants of p27: WT, ΔK1, ΔK3 or ΔK1/K3. In the presence of tetracycline, the mutants were greatly overexpressed, relative to the endogenous p27 levels, which cannot be seen in this panel (FIG. 4D, lanes 2, 4, 6, 8). Expression of p27 and all the mutants caused G1 growth arrest, as measured by PI staining and FACS analysis (FIG. 4E) and by monitoring proliferation by cell counting (data not shown). This was consistent with previous results, where we showed that p27 inhibits the other G1 cdk, cdk2, in a manner independent of its Y88 phosphorylation status and G1 arrest is detected when cdk2 is inhibited (12).

We immunoprecipated lysates with Brk antibodies and probed immunoblots with Flag antibodies to specifically detect the association of p27 mutants with endogenous Brk (FIG. 4F). We found that Brk associated with WT p27 (FIG. 4F, lane 2), but its association was reduced with the ΔK1 or ΔK1/K3 mutants (FIG. 4F, lanes 4, 8). Brk continued to associate with the ΔK3 mutant, suggesting that in vivo, the K1 region was primarily responsible for p27's interaction with Brk (FIG. 4F, lane 6). The association of Brk with the p27 mutants was not completely lost upon deletion of the K1 and K3 sites, consistent with the results seen in the in vitro binding assays (FIGS. 2A, 3D).

To determine whether the K1 or K3 site was responsible for Y88 phosphorylation in vivo, the mutants were isolated by Flag affinity chromatography, and probed by immunoblot analysis with pY88, pY74 and p27 antibodies (FIG. 4G). Consistent with the results seen in vitro with the recombinant proteins, WT and ΔK3 were still phosphorylated on Y88, suggesting that the K1 site was primarily responsible. All of the mutants were still phosphorylated on residue Y74 (FIG. 4G), consistent with in vitro results that suggested that this phosphorylation event was K1 independent. Thus, while the K3 site was originally identified as the better interactor with Brk's SH3 domain, in the context of full length p27 and full length kinases, the K1 site mediates this interaction.

Modulating Brk Levels In Vivo Modulates p27 Y88 Phosphorylation

Our data suggest that Brk phosphorylates p27 on Y88 in vitro, which leads to the model that modulation of Brk would modulate p27 Y88 phosphorylation. Brk activity has been reported to be insulin sensitive (30), so in order to increase or decrease the levels of endogenous Brk, we increased or decreased the level of insulin in the tissue culture media in MCF7 cells (FIG. 5A). When the cells were grown in the standard 10 µg/ml insulin, Brk, Src, cyclin D and Cdk4 expression were detected by immunoblot analysis with the respective antibodies (FIG. 5A, +). However, when insulin was removed from the media, Brk expression specifically decreased, while the expression of Src, cyclin D and cdk4 remained unchanged (FIG. 5A, −). When insulin was increased to 50 µg/ml in the media, Brk expression increased, again without a concomitant change in the expression of Src, cyclin D or cdk4 (FIG. 5A, +++). The modulation of Brk levels resulted in a corresponding decrease or increase in cell proliferation as detected by cell counting (FIG. 5B, left panel), without a change in cell viablity (FIG. 5B, right panel), suggesting cell cycle arrest rather than cell death. Decreasing insulin and Brk expression reduced p27 Y88 phosphorylation, while increasing insulin and Brk expression, increased Y88 phosphorylation, as detected by immunoblot analysis with pY88 antibodies (FIG. 5C). This suggests that Y88 phosphorylation is dependent on Brk levels. Y74 phosphorylation was not changed in the increased or decreased Brk conditions, suggesting that this phosphorylation occurred more constitutively in vivo (FIG. 5C).

Figure 5D:
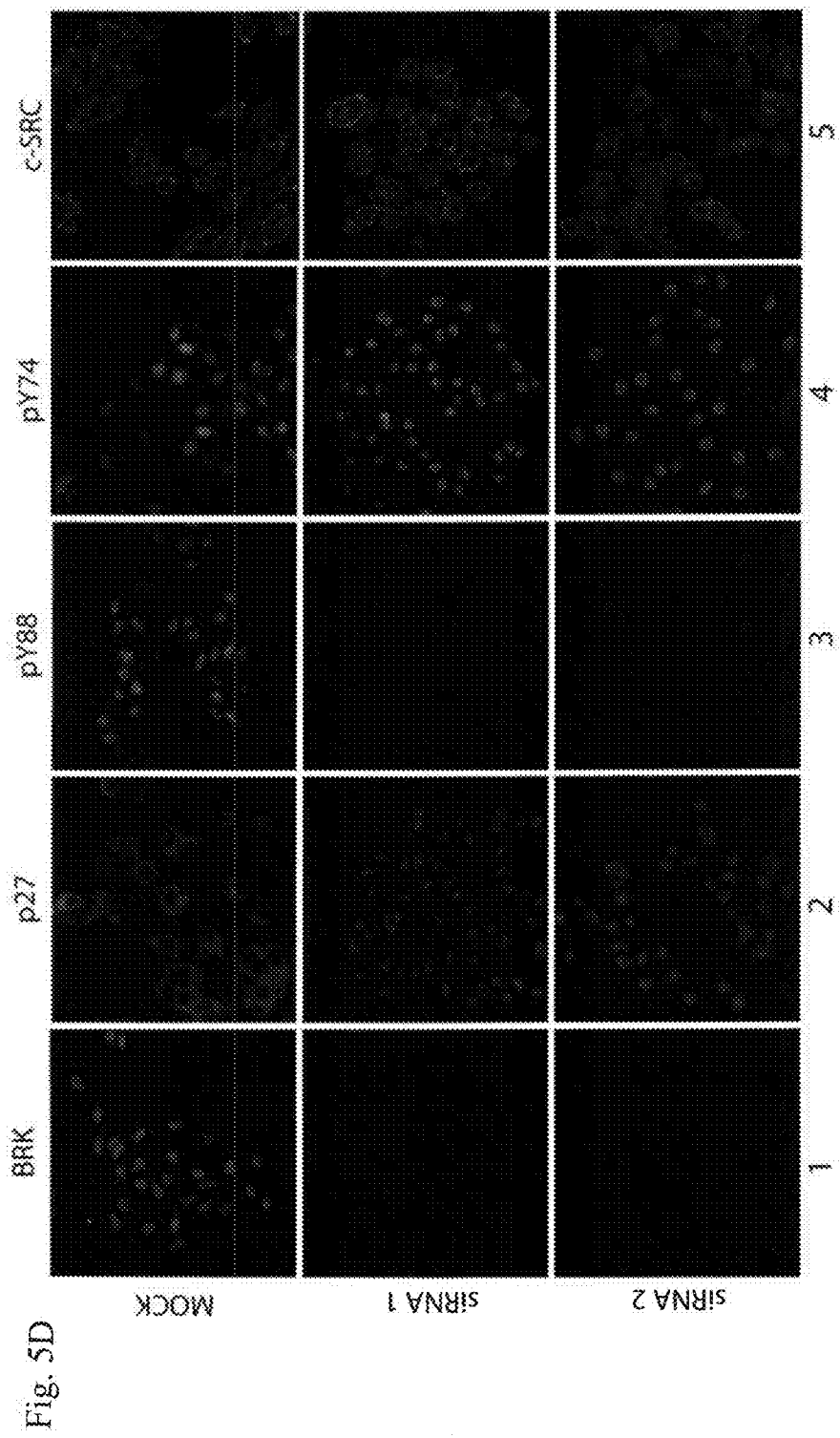

To directly demonstrate that loss of Brk affected p27 Y88 phosphorylation, we knocked down Brk using two different siRNAs that had been shown to be directed against human Brk (31). Lentivirus that expressed these siRNAs were used to infect MCF7 cells. Cells were allowed to recover for 72 h. post infection, and then we performed immunofluorescence analysis with Brk, p27, pY88, pY74, and Src antibodies (FIG. 5D, complete experiments with controls, FIG. 1). While expression was detected with all antibodies in the mock infected cells, both siRNAs effectively reduced Brk expression (FIG. 5D, lane 1), without altering either p27 (FIG. 5D, lane 2) or Src expression (FIG. 5D, lane 5). The localization of p27 became more nuclear in cells treated with both siRNAs (5D, lane 2), presumably due to the growth arrest that would result from the absence of Brk (FIG. 5B). However, loss of Brk specifically reduced Y88 phosphorylation (FIG. 5D, lane 3), while leaving Y74 phosphorylation intact. This suggests that Brk is the physiological kinase responsible for p27 phosphorylation in vivo. While Src may be competent to phosphorylate Y88, it does not appear to compensate for Brk's loss in vivo. Phosphorylation on residue Y74 appears independent of Brk's expression.

Figure 6A:
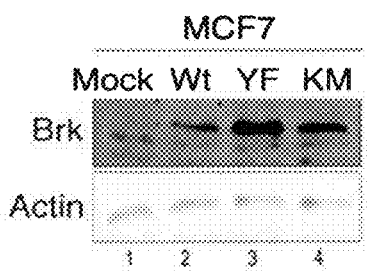
FIGS. 6A-6G: Constitutive expression of Brk makes MCF7 cells more resistant to PD0332991 (also referred to herein as Palbociclib or PD). MCF7 Mock, Brk WT, Brk YF (constitutively active) or Brk KM (catalytically inactive) were analyzed: by immunoblot analysis using Brk and actin antibodies (FIG. 6A), for proliferation rate by cell counting (6 FIG. B), by p27 immunoprecipitation followed by immunoblot analysis with pY88, pY74 and p27 antibodies (FIG. 6C) or by co-immunofluorescence using Brk (green) and pY88 (red) antibodies (FIG. 6D). Immunoprecipitation with IgG served as a negative control (FIG. 6C). DNA with Hoechst stain is in blue and is merged with red and green staining (FIG. 6D).
Figure 6B:
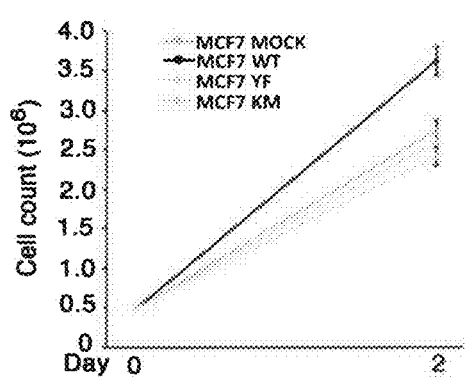
Figure 6C:
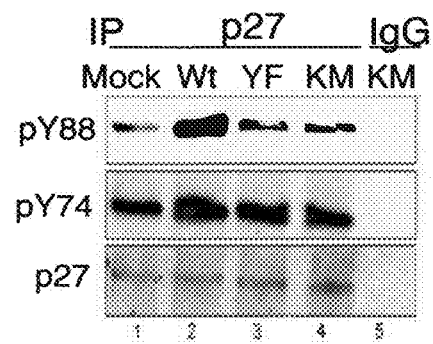
Figure 6D:
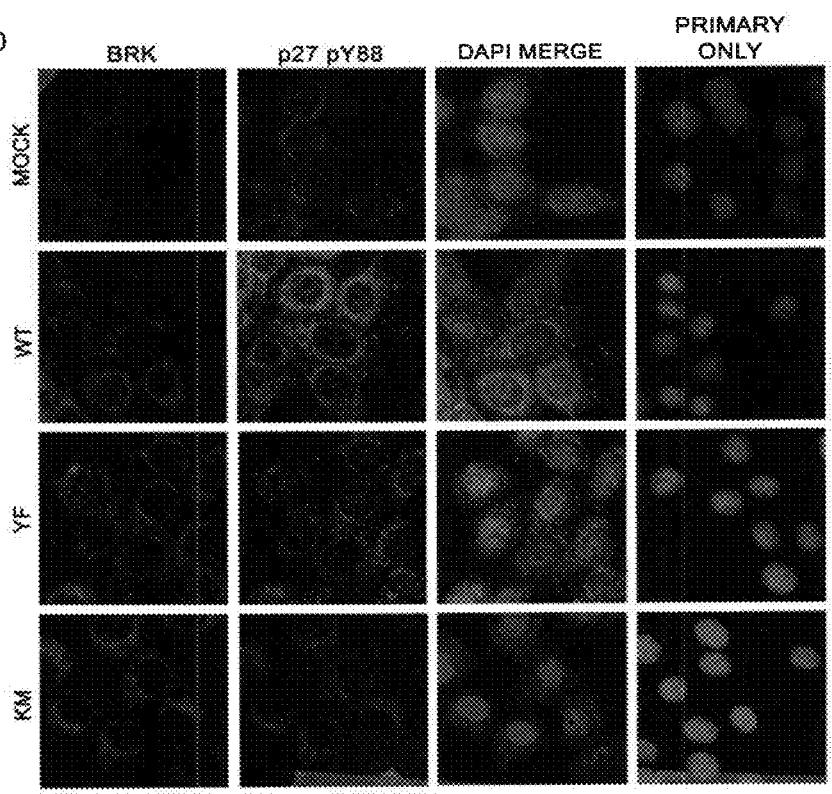
Figure 8A:
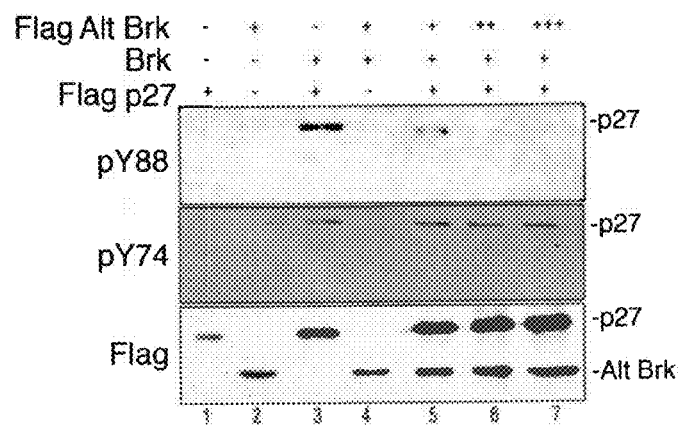
FIGS. 8A-8G: Alt Brk (SEQ ID NO: 17) acts as an endogenous inhibitor of Brk.

To further confirm that modulation of Brk modulates p27 Y88 phosphorylation, we expressed WT Brk, Brk KM (a catalytically inactive variant) and Brk YF (a constitutively active variant) (32) in MCF7 cells (FIG. 6A). Constitutive expression of WT Brk increased proliferation, as measured by cell counting (FIG. 6B), without any change in viability as measured by trypan blue staining (data not shown). Expression of the YF or KM variants did not increase proliferation, and the proliferation of these lines was similar to the mock expressing line (FIG. 6B). We immunoprecipitated p27 from the cell lines, and performed immunoblot analysis, using pY88, pY74 and p27 antibodies (FIG. 6C). The level of Y88 phosphorylation was similar in mock, KM, and YF cells, but was increased in WT-expressing cells. Y74 phosphorylation was similar in all four lines. We also performed immunofluorescence analysis with Brk, p27 and Y88 antibodies (FIG. 6D. S2A). We found that Brk was overexpressed in all three Brk expressing lines (WT, KM and YF), relative to the mock expressing cells. Because these cells were analyzed only 24 h. post plating, Brk is predominantly cytoplasmic (FIG. 6D). Its localization appears to become more nuclear as cells recover post plating (data not shown). Consistent with the immunoprecipitation results, we detected increased Y88 phosphorylation only in the WT cells. This suggests that increased p27 Y88 phosphorylation was dependent on a kinase-active Brk. It was unclear why p27 Y88 phosphorylation was not increased in the YF line, but became apparent in experiments described below (FIG. 8E).

Figure 6E:
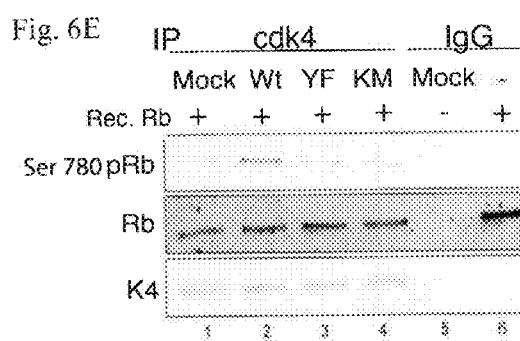

Our data demonstrated that increasing Brk expression increased p27 Y88 phosphorylation, and we hypothesized that this would increase cdk4 kinase activity. To directly examine this, we immunoprecipitated cdk4-associated complexes from Mock, WT Brk, Brk KM, and Brk YF cell lines and performed in vitro Rb kinase assays (FIG. 6E). We added exogenous Rb substrate to these immunoprecipitates and then assayed for Rb phosphorylation by immunoblot analysis using a RB phospho-specific antibody that recognizes residue Ser780 shown to be specifically phosphorylated by cdk4 (33). Cdk4-associated kinase activity was detected in the mock, YF, and KM expressing clones (FIG. 6E, lanes, 1, 3, 4), and represented endogenous cdk4 activity. However, increased cdk4-associated Rb phosphorylation was detected in the WT Brk expressing cells (FIG. 6E, lane 2), consistent with the increase in p27 Y88 phosphorylation detected here.

Figure 6F:
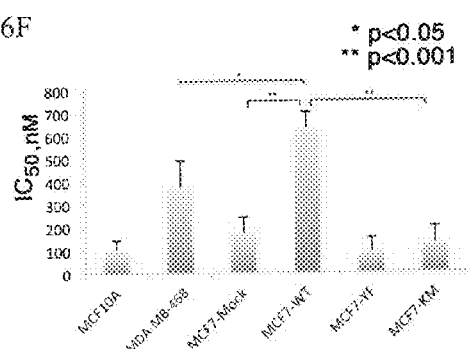

We additionally treated the Brk expressing cell lines with PD0332991, a cdk4 specific inhibitor that causes a potent G1 arrest (FIG. 6F) (34, 35). This small molecule inhibitor is exquisitely specific for cdk4, stoichiometrically blocking catalytic activity and at the concentrations used in this assay, has no activity against other serine/threonine kinases (35). Cells were plated at day 0, treated with four different concentrations of PD0332991 at day 2, and then harvested and counted at days 3 and 4 (24. and 48 h. post treatment). IC50 values were calculated, defined as the concentration of drug needed to inhibit proliferation by 50% (FIG. 6F). As seen by others, the IC50 of MCF10A and the Mock MCF7 cells were 110 and 150 nM respectively, and these lines are considered sensitive to PD0332991 treatment. MDA MB-468 cells were resistant to PD0332991 treatment, consistent with the results of others, with an IC50 value of 350 nM (36).

Figure 6G:
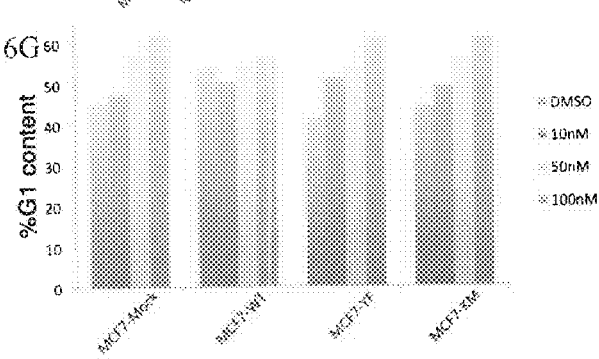

The MCF7 WT expressing cells, with their increased p27 Y88 phosphorylation, were now resistant to PD0332991 treatment, with IC50 values greater than 600 nM (FIG. 6F). The MCF7 KM and YF cells, with near endogenous levels of Y88 phosphorylation, had IC50 values similar to the mock cells. The level of p27 Y88 phosphorylation correlated with cdk4 sensitivity: increased Y88 phosphorylation resulted in increased IC50 values. This data suggest that the WT line had more cdk4 kinase activity that necessitated more drug in order to be inhibited. By immunoblot analysis, we demonstrated that the levels of cyclin D and cdk4 did not increase significantly in the WT Brk expressing cells in the presence or absence of PD0332991 (data not shown), suggesting that the activity of the complex increased instead as a result of the increased Y88 phosphorylation seen in this line. FACS analysis confirmed that the arrest seen in the mock, KM and YF cells treated with PD0332991 up to 100 nM was due to an increase in G1 content (FIG. 6G). The WT expressing cells, however, maintained an approximately 55% G1 content at these concentrations. The viability of these cells was unchanged in all concentrations of the drug, suggesting PD0332991 treatment was cytostatic and not cytotoxic (data not shown). These data suggest that Brk overexpression increases Y88 phosphorylation, and increases cyclin D-cdk4 activity, rendering those cells more resistant to specific cdk4-inhibitor therapy.

Alt Brk Acts as an Endogenous Inhibitor of p27 Phosphorylation

Figure 7A:
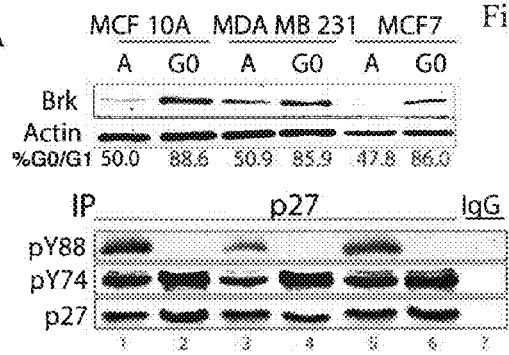
FIGS. 7A-7E: Alt Brk is upregulated in G0 cells.

Our data suggest that the level of Brk dictates the level of p27 Y88 phosphorylation since modulating Brk levels modulates Y88 phosphorylation. We had previously demonstrated that p27 Y88 phosphorylation was lost in contact arrested cells, suggesting that this was one way by which cdk4 activity was inhibited in this condition (12). The MCF10A, MDA MB 231 and MCF7 breast cell lines could all be contact arrested when grown to confluence and maintained for 6 days in the presence of replenished serum, as shown by increased G0/G1 content (FIG. 7A, bottom panel, % G0/G1). We immunoprecipitated endogenous p27 from asynchronously growing (A) and contact arrested (G0) breast cancer cells, followed by immunoblot analysis with pY88, pY74, and p27 antibodies (FIG. 7A, bottom panel). As expected, Y88 phosphorylation was only detected in the proliferating cells and was absent in the G0 arrested cells. Y74 phosphorylation was still detected in the G0 arrested cells, consistent with our observations that this phosphorylation was more differentially regulated relative to Y88 phosphorylation.

Figure 7B:
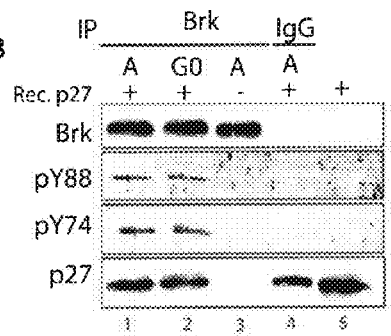

However, when we examined the levels of Brk using a C-terminal Brk antibody, we found that in fact Brk expression did not decrease in the G0 cells, but rather increased (FIG. 7A, top panel). To verify that this Brk was catalytically active, we immunoprecipiated Brk from A and G0 cells, and then incubated the immunoprecipitates with recombinant p27 and ATP in vitro (FIG. 7B). Brk immunoprecipated from both A and G0 cells was able to phosphorylate recombinant p27 (FIG. 7B, lanes 1, 2). We immunoprecipitated this Brk under stringent conditions, so endogenous p27 was not recovered and phosphorylation was only detected in the reactions where recombinant p27 was added (FIG. 7B, compare lanes 1, 2 to lane 3).

Figure 7C:
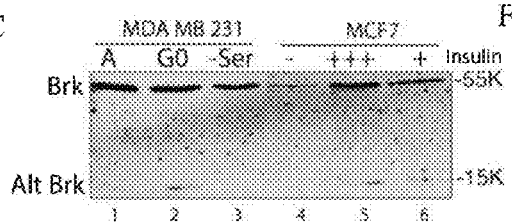
Figure 7D:
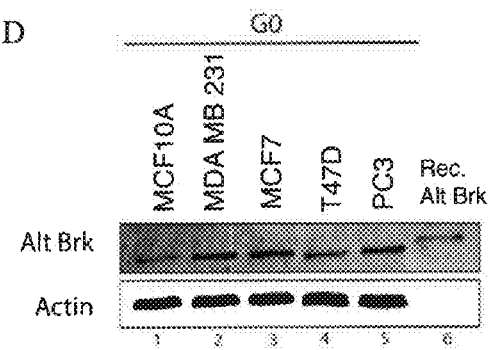
Figure 7E:
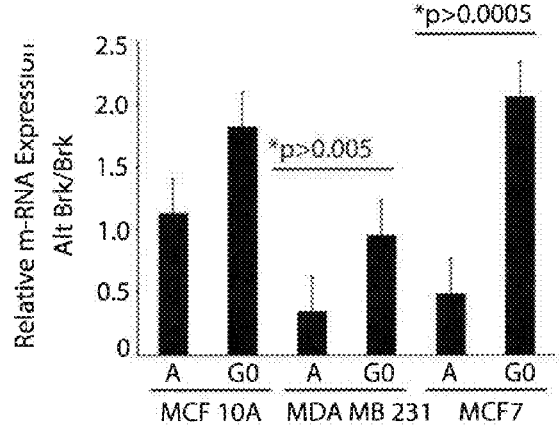

Thus, Brk was present and active in contact arrested (G0) breast cells, but p27 was not phosphorylated on residue Y88 (FIG. 7A, bottom panel). An alternative splice variant of Brk, Alt Brk (SEQ ID NO: 17), which lacks expression of exon 2 and encodes a shorter 15 KD protein, has been reported in the breast cancer cell line, T47D, and in several prostate and colon cancer cell lines (37, 38). This Alt-Brk shares the N-terminal SH3 domain with Brk, has a unique proline rich carboxy terminus, but lacks the catalytically active SH1 kinase domain (38). Given our results where we demonstrated that the addition of exogenous SH3 peptides could block Brk's phosphorylation of recombinant p27 (FIG. 3C), we hypothesized that Alt-Brk might compete with full-length Brk for binding to p27 and function as an endogenous inhibitor of p27 phosphorylation. Using an N-terminal specific antibody of Brk, which would recognize both full length and Alt Brk, we detected Alt in G0 cells (FIG. 7C,D). We performed q-RT-PCR on lysates derived from proliferating (A) or contact arrested (G0) cells, and found that the ratio of Alt Brk:Brk was significantly increased in G0 cells (FIG. 7E).

This data suggested that the presence of increased Alt could lead to its increased association with p27, which might block the interaction of full length Brk or essentially out-compete Brk for p27's association. To directly verify this, we expressed a Flag-tagged Alt-Brk in bacteria and purified this 15 Kd protein (FIG. 8A). When p27 was incubated with Brk, Y88 and Y74 phosphorylation was detected by immunoblot analysis (FIG. 8A, lane 3). When increasing concentrations of Alt-Brk were added to the reaction, Y88 phosphorylation decreased (FIG. 8A, lanes 5-7). Y74 phosphorylation was not affected. This suggested that Alt Brk was able to function as an inhibitor, similar to the small SH3 peptide used in FIG. 3C, blocking Brk's phosphorylation of residue Y88.

Figure 8B:
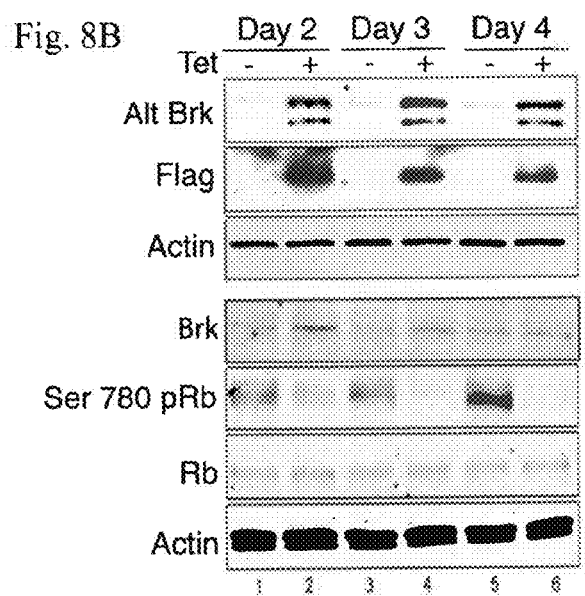
Figure 8C:
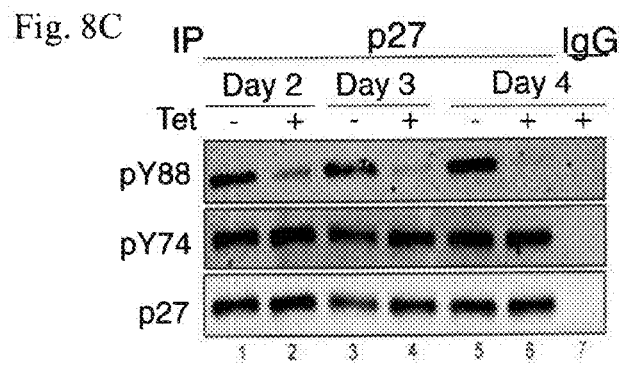
Figure 8D:
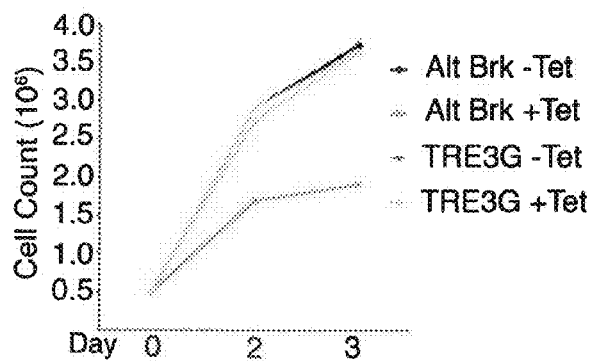
Figure 8E:
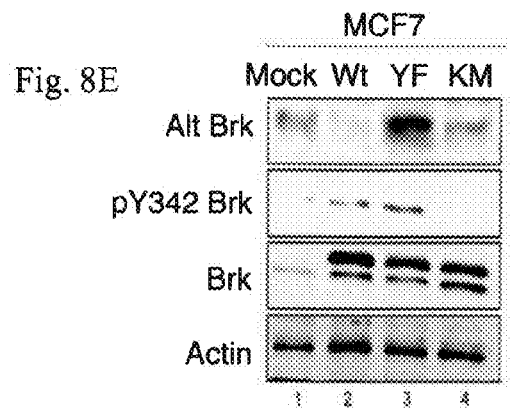

To verify this in vivo, we expressed Flag tagged Alt Brk in a tetracycline inducible manner in MCF7 cells (FIG. 8B-D). When tetracycline was added to the culture media, Alt Brk expression was detected using the N-terminal Brk and Flag antibodies (FIG. 8B), and cells were arrested in G1 phase, as detected by cell counting (FIG. 8D) and FACS analysis (data not shown). When endogenous p27 was immunoprecipitated from the Alt Brk expressing cells, p27 Y88 phosphorylation was reduced, while Y74 phosphorylation was unchanged (FIG. 8C), suggesting that Alt Brk functions in vivo as an endogenous inhibitor of p27 Y88 phosphorylation. We examined Rb phosphorylation on residue Ser780 as a measure of cdk4 kinase activity (FIG. 8B). Rb phosphorylation was reduced consistent with the loss of p27 Y88 phosphorylation, which would translate into a reduction in cdk4 activity and growth arrest.

Figure 8F:
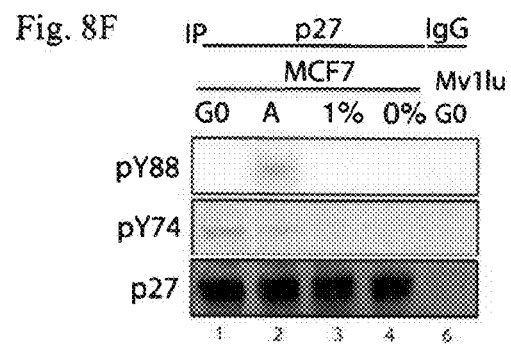
Figure 8G:
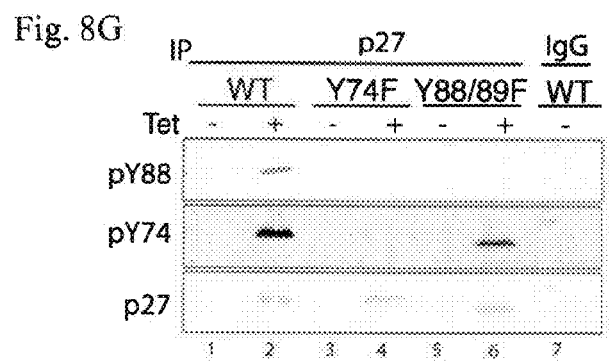

Our model suggested that increasing Brk would increase p27 Y88 phosphorylation, which in turn would increase cdk4 activity and PD0332991 resistance. However, Alt Brk, functioning as an endogenous inhibitor of Brk's phosphorylation of p27, could dampen this cascade. We returned to examine the MCF7 cells that overexpressed Brk YF, the catalytically active variant, as described in FIG. 6. It had been unclear why this mutant did not cause an increase in p27 Y88 phosphorylation, even though exogenous Brk was detected both by immunoblot analysis (FIG. 6A, 8E) and immunofluorescence (FIG. 6D). When we examined the YF expressing cells using an antibody that recognizes active Brk (pY342), we found that the WT and the YF expressing cells had more active Brk than either the mock or KM expressing cells (FIG. 8E). However, using the N-terminal Brk antibody, we now detected an increase in Alt Brk expression specifically in the YF cell line (FIG. 8E, lane 3), suggesting that even though exogenous Brk was expressed, its inhibitor was also expressed. This explained why, in the YF line, we had not detected a change in p27 Y88 phosphorylation (FIG. 6C, D) and had not seen an increase in PD0332991 resistance (FIG. 6E). Our data demonstrated that the ratio of Alt Brk: Brk will dictate the status of p27 Y88 phosphorylation, which in turn regulates cdk4 activity and PD0332991 sensitivity. Thus, Alt Brk, with its SH3 domain, functions as an endogenous cdk4 inhibitor. While Alt Brk was able to block Y88 phosphorylation, it did not affect Y74phosphorylation, consistent with our results that suggest that Y74 phosphorylation is differentially regulated. Y74 phosphorylation was not affected by loss of Brk expression (FIG. 5D, lane 4) or in cells arrested by contact (FIG. 7A, bottom panel) and loss of the K1 site did not prevent Y74 phosphorylation in vitro (FIG. 2E), and in vivo (FIG. 4G, lanes 4,6). We did see loss of Y74 phosphorylation when MCF7 cells were grown in the absence of serum (FIG. 8F, lanes 3, 4), suggesting mitogen dependence. We examined the phosphorylation state of p27 and mutants Y74F and Y88/89F overexpressed in MCF7 cells in a tetracycline-inducible manner. In the presence of Tet, these mutants were detected by immunoblot using p27 antibodies, while endogenous p27 levels were too low to be detected (FIG. 8G, lanes 2, 4, 6). WT p27 was phosphorylated on both residues. Mutant Y88/89F was not phosphorylated on residues 88 or 89 due to mutation, but was still phosphorylated on residue Y74 (FIG. 8G, lane 6). Mutant Y74F was not phosphorylated on residue Y74, as expected, nor on residue Y88 (FIG. 8G, lane 4). Together this data suggests that phosphorylation on Y74 is Brk independent, but may be required for efficient phosphorylation on Y88 by Brk. However, Y88 phosphorylation, which is regulated by Brk in an SH3:PxxP dependent manner, is the switch that modulates cdk4 activity.

Figure 9A:
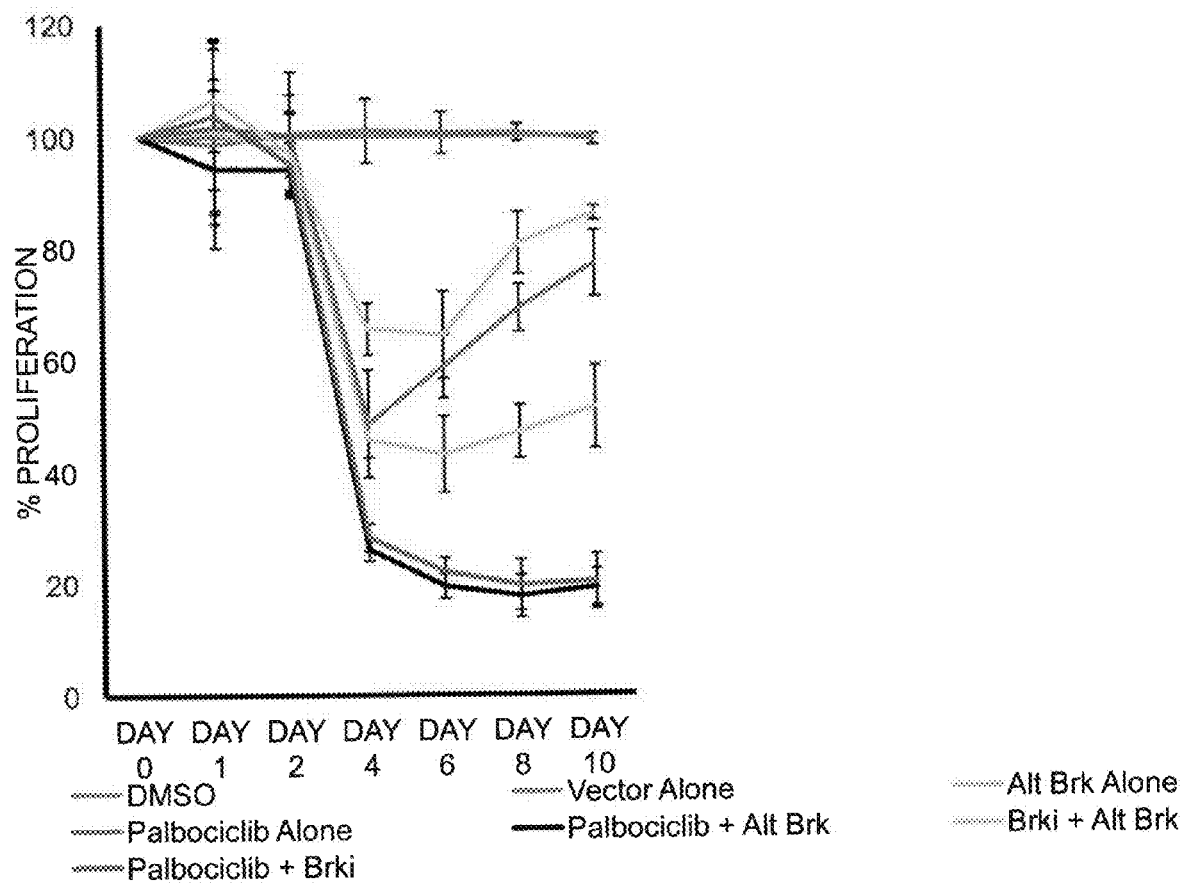
FIGS. 9A-9B: AltBrk Synergizes with Palbociclib. ALT, Palbociclib, or Brk alone or in combination were added to or expressed in MCF7 breast cancer cells on day 2 post plating. Drugs were added at their IC50 concentration, based on previous results. ALT is expressed from an ALT-MCF7 tetracycline inducible cell line generated in the Blain lab. When tetracycline is added to the cell culture media, ALT is expressed in these cells. Vector: no tetracycline was added, so no ALT induction was detected.
Figure 9B:
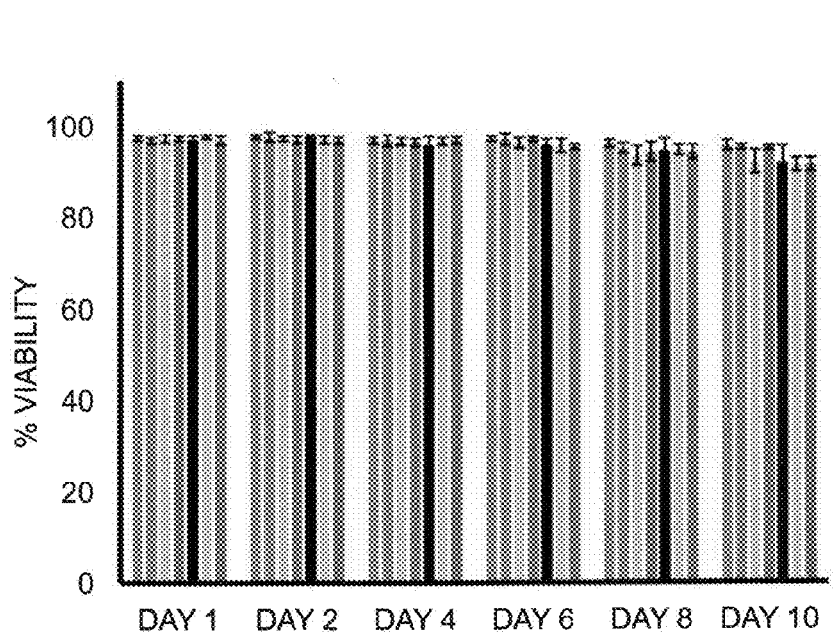
Figure 10:
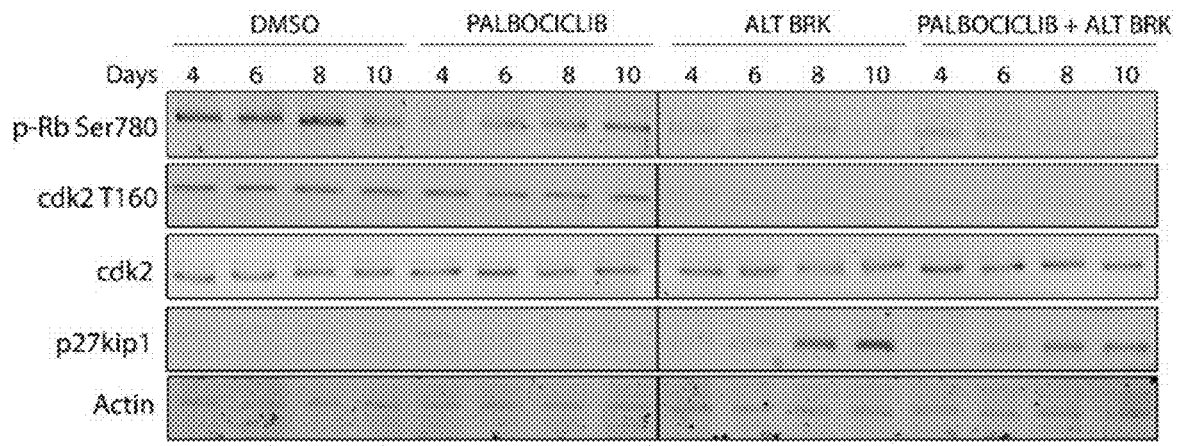
FIG. 10: ALT BRK inhibits both CDK4 and CDK2. ALT, Palbociclib alone or in combination were added to or expressed in MCF7 breast cancer cells on day 2 post plating. Drugs were added at their IC50 concentration, based on previous results. ALT is expressed from an ALT-MCF7 tetracycline inducible cell line generated in the Blain lab. When tetracycline is added to the cell culture media, ALT is expressed in these cells. Vector: no tetracycline was added, so no ALT induction was detected. Drugs and media were replaced every two days. Cells were harvested every two days, lysed and used in immunoblot analysis. Actin: loading control. pRBser780 is a phospho-specific antibody that recognizes sites phosphorylated by cdk4, so is a measure of active cdk4. cdk2T160 recognizes a required phosphorylation event on residue T166 and is a measure of activated cdk2.
Figure 11:
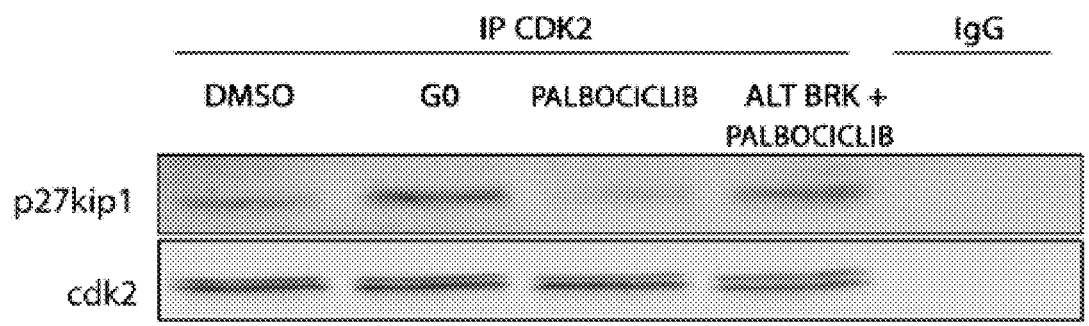
FIG. 11: CDK2 is inhibited by p27KIP1 in ALT/BRK/Palbociclib Treated Cells. ALT, Palbociclib alone or in combination were added to or expressed in MCF7 breast cancer cells on day 2 post plating. Drugs were added at their IC50 concentration, based on previous results. ALT is expressed from an ALT-MCF7 tetracycline inducible cell line generated in the Blain lab. When tetracycline is added to the cell culture media, ALT is expressed in these cells. Vector: no tetracycline was added, so no ALT induction was detected. Drugs and media were replaced every two days. Cells were harvested every two days, lysed and used in immunoprecipitation analysis with cdk2 antibodies, followed by immunoblot analysis with p27 or cdk2 antibodies. IgG is normal rabbit serum as a control.
Figure 12A:
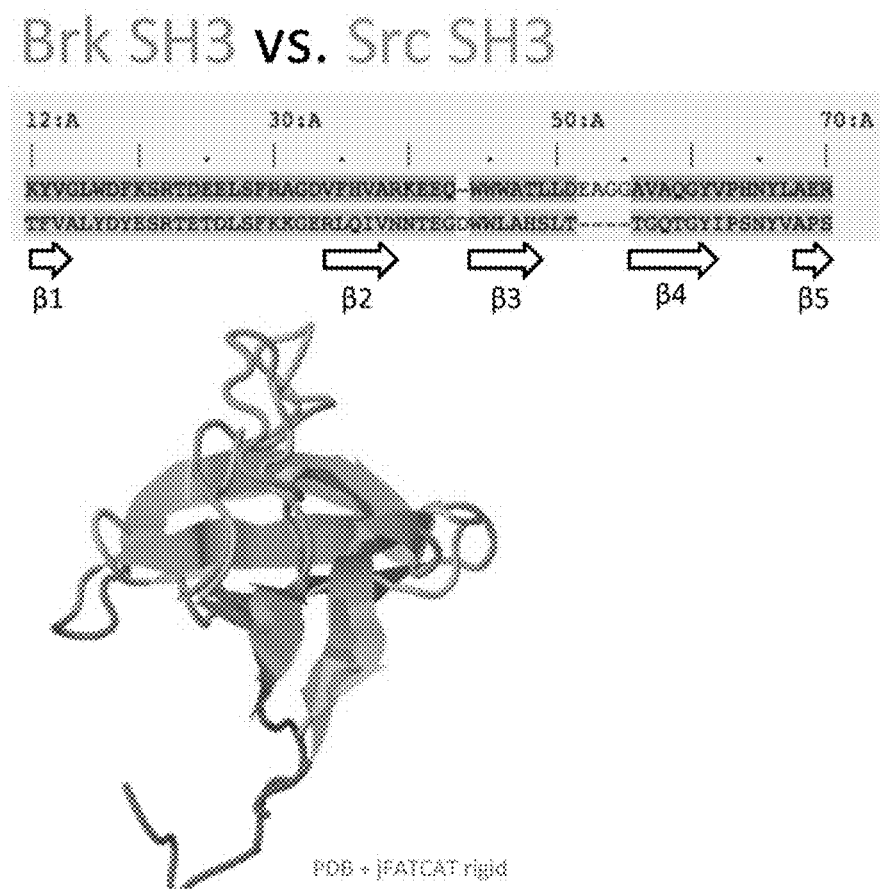

Additional experiments were performed assessing activity of Brk in combination with Palbociclib. The data presented in FIGS. 9A and 9B reveal that Palbociclib and Brk inhibit proliferation for 2 days, and then resistance is observed (proliferation increases). Alt maintained arrest for roughly 10 days (50% inhibition of proliferation is detected). Alt+ Palbociclib arrests cells in an additive fashion at day 4-8, but by day 10, synergy is detected. Alt-Brk/Palbociclib combination leads to a more durable cell cycle arrest. Mono therapy treated cells start to become resistant between day 8-10. Palbociclib+Alt combination treated cells are still arrested at day 22. Note this plot is not percentage, but represents total cell counts. By day 22, the Palbociclib+ALT combination treated cells number $2\times10^6$, which is roughly 1% of the untreated cells at day 22. Moreover, Alt-Brk inhibits both CDK4 and CDK2 activity. See FIG. 10. The data show that Palbociclib inhibits cdk4 (reduction of pRB-ser780), but does not inhibit cdk2 (cdk2T160 still detected). Alt inhibits cdk4 (reduction of pRBser780), and inhibits cdk2 (cdk2T160 not detected). Palbociclib+ALT combination inhibits cdk4 (reduction of pRBser780), and inhibits cdk2 (cdk2T160 not detected). p27 total levels are increased in Alt or Palbociclib+Alt combination treatment, due to reduced phosphorylation dependent degradation. CDK2 is inhibited by p27Kip1 in Alt Brk/Palbocilib treated cells. The presence of cdk2 demonstrates that an equal amount was immunoprecipitated from the different lysates. More p27 was associated with the same amount of cdk2 from the Palbociclib+Alt combination treated cells, as compared to the Palbociclib treated cells. G0 represents contact arrested MCF7 cells, where we and others have shown that p27 is associated with cdk2, inhibiting this kinase. See FIG. 11. The sequence of the Brk SH3 domain is provided in FIG. 12.

Figure 13A:
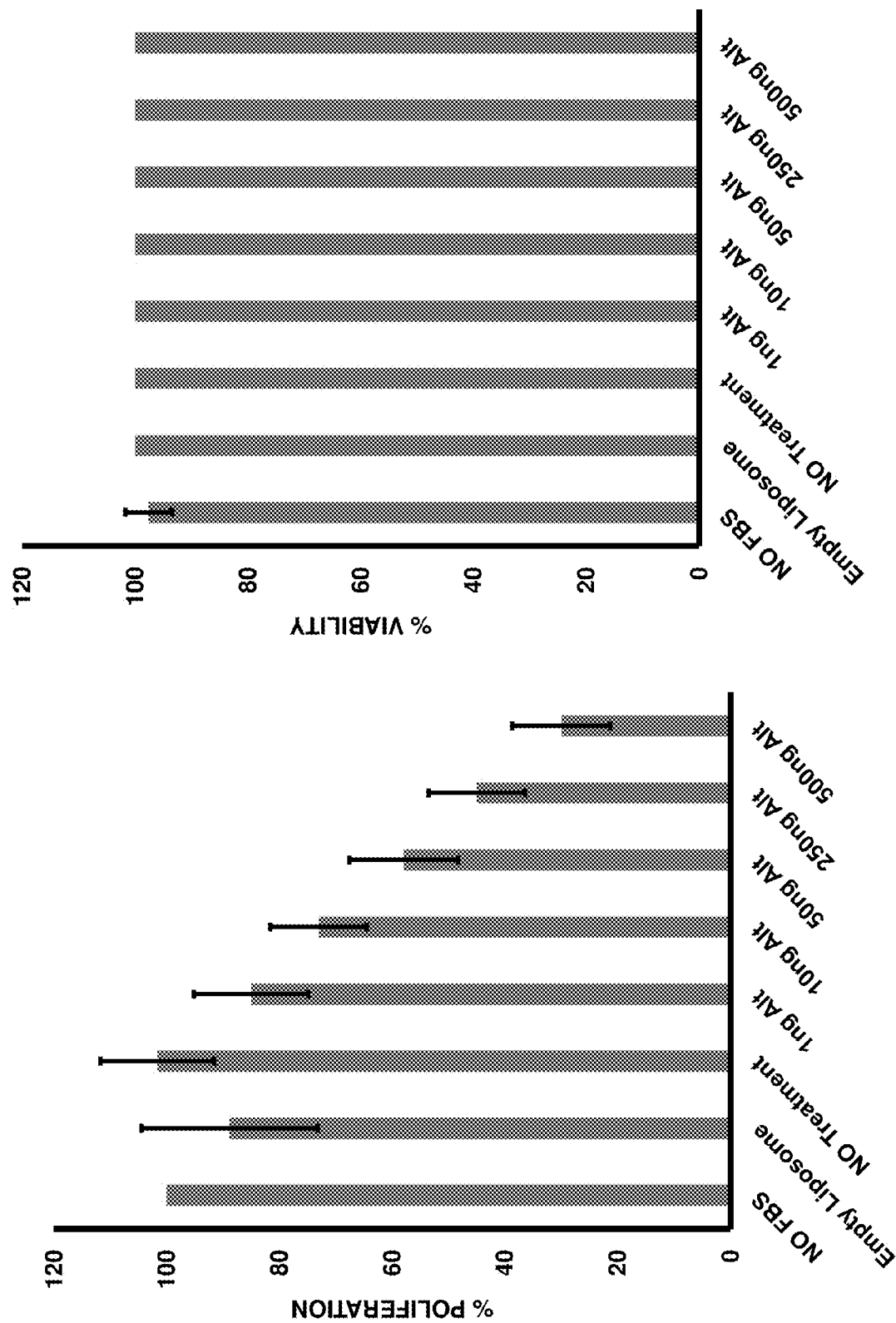
FIGS. 13A-13C: NP-ALT causes growth arrest in three different breast cancer lines. NP-Alt-Brk was added at different concentrations (ng/ml) for 6 h. to three different breast cancer cell lines, which have different sensitives to the cdk4 specific inhibitor, Palbociclib.
Figure 13B:
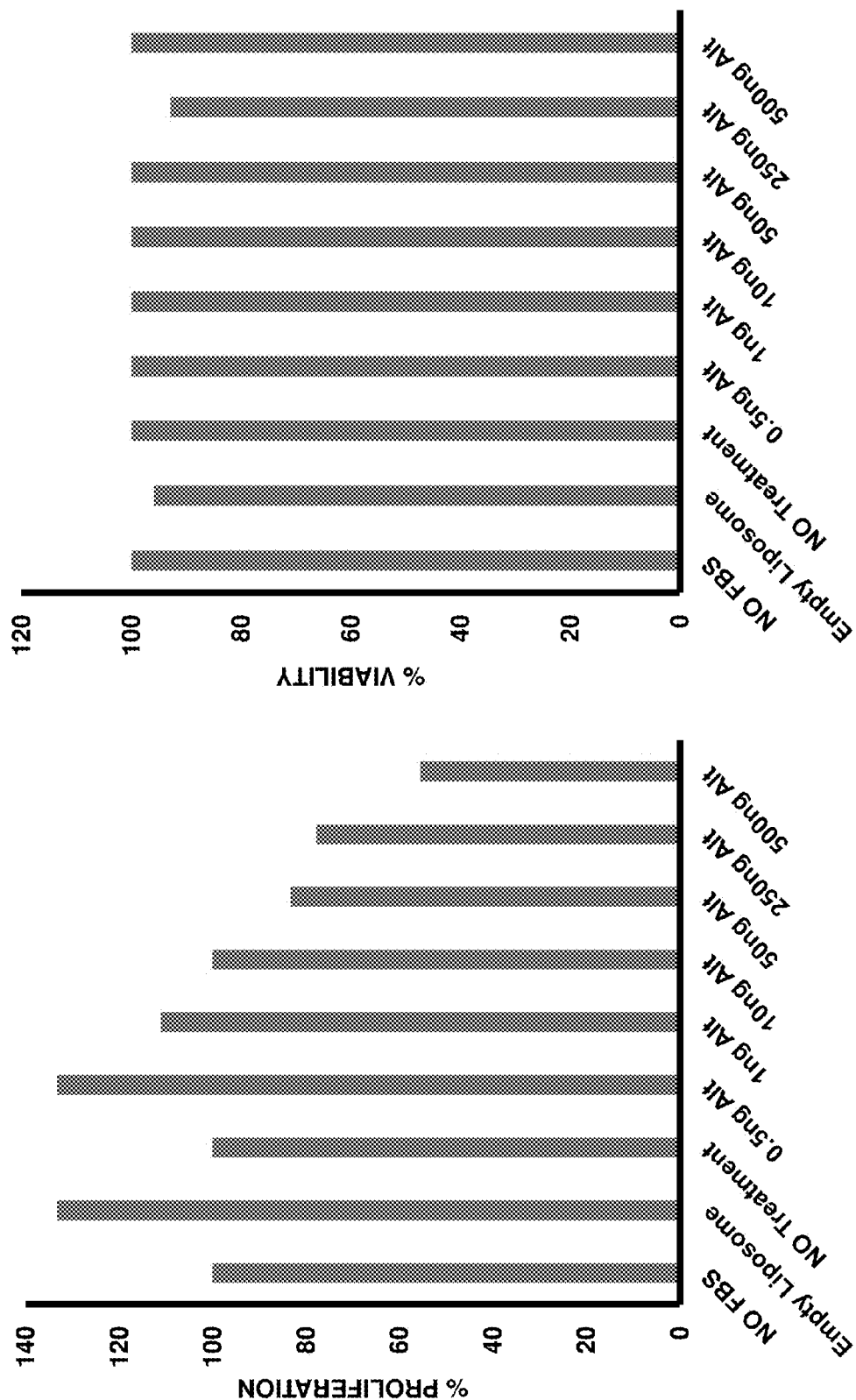
Figure 13C:
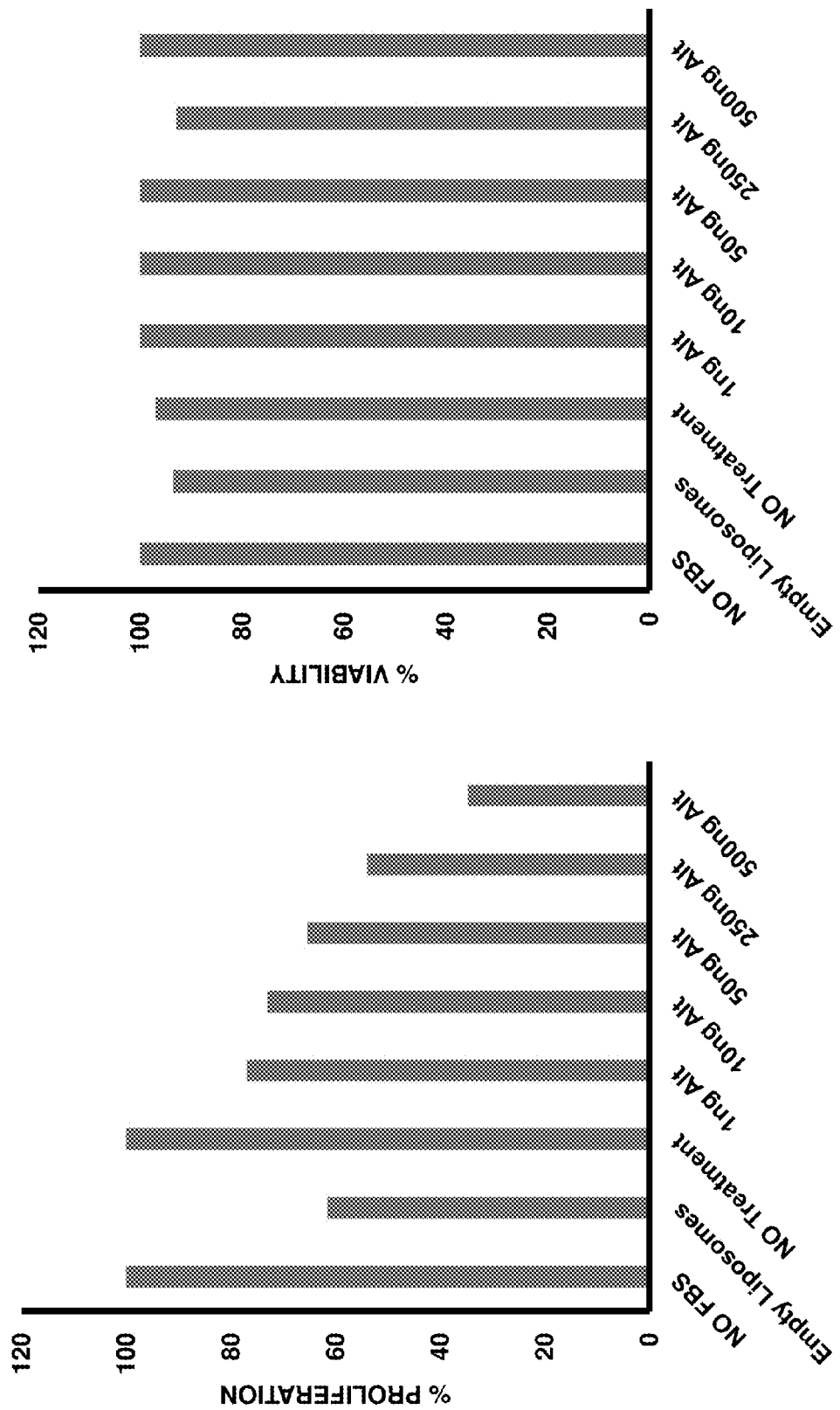

We performed additional experiments using nanoparticle formulations of Alt-Brk (NP-Alt). FIGS. 13A, 13B and 13C demonstrate that NP-ALT causes growth arrests in three different types of breast cancer lines, MB231, MCF7 and HCC1954. NP-Alt was added at different concentrations (ng/ml) for 6 h to three breast cancer cell lines that have different sensitivities to Palbociclib. NP-Alt was removed and fresh NP free-media added for 2 days, followed by proliferation rate and viability assessments. Proliferation rate was determined by performing cell counting and standardization against the NO FBS control set to 100%. Viability was performed by trypan blue staining with the NO FBS set to 100%. Empty liposome is the NP formulation without conjugated ALT peptide. NO treatment control is the proliferation rate of cells not treated with the experimental conditions.

We also provide data showing that ALT-Brk slows tumor growth in animals, and a combination of ALT-Brk expression and PD treatment causes tumor regression. See FIG. 14. MCF-7 inducible ALT cells were injected into the 4$^{th}$ mammary gland of NOD/SCID mice. Tumors were allowed to develop to a volume of 200 mm3, before treatment. Vehicle: daily gavage with PBS. PD: Daily gavage of Palbociclib 100 mg/kg. Doxy: 0.1 mg/ml doxycycline added to the drinking water to allow continuous uptake and induction of ALT in the human cancer cells. Doxy+PD: Daily gavage of Palbociclib 100 mg/kg and 0.1 mg/ml doxycycline added to the drinking water. Vehicle treated animals rapidly progressed and by 17 days, tumor volumes were >3000 mm PD treatment slowed down tumor growth but by day 17, tumors were >2500 mm3. Doxy (ALT induction) significantly slowed down tumor growth and by day 17, tumors were ~1500 mm3. However, dual ALT and PD (doxy/PD) treatment, caused tumor regression by >10%, by day 5, which was durable up to day 19. At day 17, one vehicle and PD treated animals were treated with the dual Doxy/PD treatment and immediate tumor regression was seen and by day 27, tumors had decreased from volumes by half.

In FIGS. 15A, 15B and 15C, we demonstrate that ALT expression and PD treatment combination treatment increases senescence, a highly desirable clinical goal. MCF7-ALT cells were treated with a IC100 concentration of Palbociclib (PD) or doxycycline to induce ALT. Drugs were replenished every two days and proliferation was determined by cell counting as indicated. Proliferation rates were standardized to the rate of proliferation seen in DMSO treated cells (control). PD treated cells were arrested for 10 days, before escape (proliferation) was detected. ALT expressing cells were arrested for 18 days before escape (proliferation) was detected. ALT expressing and PD treated cells were arrested for 30 days, with no escape detected. In FIG. 15B, cells were treated with drug combinations for 6 days, drug was removed and cells were replated in fresh drug free media. Proliferation was assessed by counting. In the presence of DMSO, PD, and ALT expression, cells started to proliferate. Proliferation of ALT expressing and PD treated cells were delayed due to the growth arrest of those cells. However, the dual ALT expressing, PD treated cells never regained proliferation. Viability was measured by trypan blue staining and the ALT expressing, PD treated cells that weren't growing were viable. Cells were stained for the presence of beta-galactosides, a senescence marker. Beta-galactosidase was increased in the dual treated cells.

Discussion

We have identified Brk/PTK6 as an authentic p27 kinase that can activate the p27 ON/OFF switch, and is thus able to modulate cyclin D-cdk4 activity. While many SFKs appear competent to phosphorylate p27, Brk phosphorylates p27 more efficiently, and its SH3 domain associates with a higher affinity. Reducing Brk expression by siRNA in vivo eliminates p27 Y88 phosphorylation, even though Src is expressed, demonstrating that Brk is the physiological kinase in these cells. It is striking that Brk is overexpressed in many of the same cancers that appear dependent on cdk4 kinase activity. Increased expression of Brk in breast cancer cells would increase p27 Y phosphorylation and increase resistance to cdk4 inhibition in a kinase-dependent fashion, suggesting that a limiting factor in this type of therapy is the level of active cdk4. These data lead to the following model: at least in some tumors, Brk expression regulates p27 Y phosphorylation, which in turn regulates cdk4 activity and cell cycle progression and sensitivity to cdk4 specific targeting therapy. In ongoing work, we are actively looking for this direct connection in breast tumors. We have detected both Brk expression and Y88 phosphorylation in primary breast tumors embedded in paraffin (unpublished data). It remains to be determined whether p27 Y phosphorylation or Brk expression will serve as a marker for cdk4 activity and in turn cdk4 inhibitor sensitivity.

Brk protein is detected in both the cytoplasm and nucleus of normal human mammary cells, but it appears to be catalytically inactive. However, Brk is overexpressed in more than 60% of human breast carcinomas (39, 40) and in high-grade human breast tumors, it is both overexpressed and active at the plasma membrane (40, 41), suggesting constitutive signaling in these tumors. Its expression promotes proliferation and tumor growth in human mammary epithelial cells, although the direct substrate(s) required for this tumor-promoting effect had not been identified. Brk lacks the amino-terminal myristoylation/palmitoylation typical of Src family members, and as such has a wider area of localization and binding partners (42-44). Several Brk substrates have been identified (24) including β-catenin, p190RhoGAP, Paxillin, PSF, STAT5, Sam68, SLM1, SLM2, AKT, p130CAS, and FAK (45) but the identification of p27 as a direct phosphorylation target provides new insights about Brk's role in proliferation control and directly links it to cdk regulation. Others have suggested that Brk has additional roles in p27 regulation: In MDA MB 231 cells and Src, Yes, Fyn null MEFs, Brk overexpression transcriptionally downregulates p27 (45, 46).

Brk appears to phosphorylate p27 on residue Y88 in an SH3 dependent manner Loss of the K1 site prevents Y88 phosphorylation in vitro and in vivo, and addition of either a K1-containing peptide or an SH3-containing peptide is able to prevent Y88 phosphorylation. The importance of the PxxP:SH3 interaction is further demonstrated by the effect of Alt Brk expression. Alt Brk contains Brk's SH3 domain, but lacks the kinase domain, and is able to inhibit Brk's phosphorylation of p27 in vitro and in vivo. Alt Brk appears to function as a competitive inhibitor and our data consistently demonstrates that the ratio of Alt Brk:Brk dictated the status of p27 Y88 phosphorylation, which in turn regulates cdk4 activity and PD0332991 sensitivity. Alt was increased in cells arrested by contact, but the regulation of Alt to Brk and its potential role in tumors remains to be determined We found an increase in Alt Brk when constitutively active YF Brk was overexpressed, suggesting that the expression of Alt may be due in part to self regulation by Brk itself. Alt has been found to associate in vivo with additional other Brk substrates, and in its presence, phosphorylation of Brk itself and overall phosphotyrosine levels were reduced (38). Thus, exogenous expression of Alt may affect the activity of other substrates, which might contribute to the associated growth arrest. However, our data clearly demonstrates that Alt Brk functions as an endogenous inhibitor of p27 Y phosphorylation. This suggests that we have identified a novel, potentially targetable domain and blocking the PxxP: SH3 interaction might be viable strategy to inhibit p27 Y phosphorylation and cdk4 activity, which can be explored therapeutically.

p27 is a well-characterized tumor suppressor, whose loss or reduction appears to be required to activate oncogenic cdk2. However, because of its role as an activator of cyclin D-cdk4 complexes, p27 may also function as an oncogene (47, 48). In the ErbB2 breast cancer model, tumorigenesis is accelerated in p27+/− mice compared to p27+/+ animals, while tumorigenesis is blocked in the complete absence of p27 (p27−/−) (49, 51). Thus, in this breast cancer model, while p27 levels must be reduced to release oncogenic cdk2, residual p27 is required to accelerate tumor formation, via assembly and activation of cyclin D-cdk4. In humans, p27 is rarely mutated or silenced, suggesting a similar requirement for residual p27 levels may exist (51). p27 levels are reduced by accelerated proteolysis or cytoplasmic mislocalization, likely related to increased oncogenic signaling. Decreased but residual p27 levels correlate with more aggressive phenotypes, high proliferation indices, increased invasive behavior, and high mortality (51). Thus, while p27 levels are reduced in human tumors, the residual p27 that remains, would be in the ON position to activate cdk4. This would imply that in tumors, a decreased level of p27, with a concomitant increased level of pY88, would be oncogenic. Direct evidence for an oncogenic role of the Cip/Kip proteins has been demonstrated only for p21 in a glioblastoma model, where loss of the homologous Y phosphorylation site in p21, prevented PDGF-dependent tumor formation (52). Formal description of p27's oncogenic role in animal models is still outstanding, but is being actively pursued.

Characterization of p27's oncogenic function is important because cdk4 has been a highly sought after therapeutic target for decades, given that cdk4 and cyclin D are frequently over-expressed in many tumor types. PD0332291, now known as Palbociclib, is currently in clinical trials for multiple myeloma and breast cancer, and has shown promising results (53). This is the first cdk4 inhibitor with the required specificity to provide therapeutic benefit, extending median PFS for metastatic breast cancer patients from 10.2 with letrozole alone to 20.2 months with combination of letrozole and Palbociclib (54). In this study, cyclin D amplification and/or loss of p16 did not correlate with sensitivity. The best biomarker of response to date is RB positivity, but even that is not full proof, suggesting that a marker for cdk4 activity itself, such as p27 Y phosphorylation, will be required. For example, RB+ pancreatic ductal adenocarcinomas (PDAC) were a priori considered targetable tumor types, dependent on cdk4 activity, due to the early loss of the cdk4 inhibitor p16 (INK4A) and activation of RAS seen in approximately 80% of cases. However, most PDAC cells appear resistant to CDK4/6 inhibition. Recently, it was shown that PD0332291 synergizes with IGFR1 receptor inhibitors to repress the growth of PDAC (55). Given Brk's insulin sensitivity, it is interesting to speculate that reducing IGFR1 signaling may reduce Brk activity and decrease p27 Y phosphorylation, which in turn may reduce cdk4 activity to a level that can now be inhibited by PD0332291. Brk specific inhibitors or p27 Y phosphorylation specific inhibitors, such as Alt Brk, appear to synergize with PD0332291, decreasing the amount of active cdk4, increasing the efficacy of this type of therapy. Screening for p27 Y phosphorylation might serve as an indicator of tumors that would be responsive to cdk4-specific inhibition. If the tumors did not contain p27 pY88 they would likely not respond to Palbociclib, but if they contained too much p27 pY88 and too much cdk4 activity, they might be resistant.

Palbociclib treatment of ER/PR+, Her2− cell lines inhibits cdk4 activity, as seen by reduced endogenous RB phosphorylation, but cells rapidly adapt to this, and increase cdk2 activity. See FIG. 10. Cdk2 is able to restore RB phosphorylation, and permit cells to reenter cycle and proliferate. Cdk2 activity increases because p27 levels are reduced due to degradation and can no longer associate with and inhibit cdk2. Thus, the cdk4-specific arrest mediated by drugs like Palbociclib, is not durable. To achieve durable cell cycle arrest, both cdk4 and cdk2 should be inhibited. However, when cells over-express ALT and block p27 pY, both cdk4 and cdk2 are inhibited. p27 levels remain high and its degradation is blocked as it remains associated with cdk2.

These data indicate that ALT treatment should produce longer periods of remission for patients, similar to what was seen in the MCF-7 xenograft model (FIG. 14). While Palbociclib treatment does slow tumor progression, ALT treatment alone is more effective while dual Palbociclib and ALT treatment actually causes tumor regression. This is due to increased senescence, similar to what is seen in dual Palbociclib and ALT treated cells in tissue culture (FIG. 15). Senescence is a clinical goal, not achievable with Palbociclib treatment alone. Senescence typically activates an endogenous immune program, causing macrophages to clear the senescent cells. In the xenograft model described above, both ALT mono therapy and ALT+Palbociclib dual therapy resulted in significantly increased remission periods, which should also translate into significantly increased remission period in human patients. ALT or its derivatives can be packaged in delivery vehicles, including the lipid based nanoparticles used in the present example. These first generation drugs inhibited proliferation of several different types of cell lines, including ones that were Palbociclib non-responsive (HCC1954).

In conclusion, blocking pY provides an innovative approach for the treatment of cancer, particularly breast cancer because 1) the p27 target is unique, so blockage of this target should have fewer off-target effects, resulting in less toxicity for the patient, 2) targrting p27 should prevent acquired drug resistance by hitting both cdk4 and cdk2 simultaneously, resulting in a prolonged response to the drug, translating into increased patient survival and 3) agent which interfere with pY phosphorylation can be used alone or in combination with Palbociclib, thereby improving efficacy of the therapy in pre-clinical tests which reveal that dual therapy causes tumor regression rather than the tumor stasis seen with administration of Palbociclib alone.

The full significance of Y74 phosphorylation is still to be determined, but it appears to occur in an SH3-PxxP independent fashion, and in the absence of Brk, additional Y kinases can compensate in vivo. As a monomer, Brk is able to phosphorylate p27 on both Y88 and Y74 independently (FIG. 2E), but we found that in vivo Y74 may serve as a prerequisite to allow Y88 phosphorylation (mutant Y74F was not phosphorylated on either residue Y88 or Y74). Phosphorylation on both Y88 and Y74 is required to activate cyclin D-cdk4, so even in contact arrested cell, where Y74 phosphorylation is still detected, cdk4 is inactive. This leads to the suggestion that p27 may be phosphorylated by multiple kinases in a mitogen dependent fashion on residue Y74, with the complex remaining inactive until regulated SH3-dependent Y88 phosphorylation occurs to convert the complex to a higher specific activity form. Thus, the model of p27 activation of cdk4 might eventually be refined even further, where p27OFF, p27Low, and p27High represent the unphosphorylated, singly phosphorylated, or fully phosphorylated p27 versions, which in turn would translate into different levels of cdk4 activity, and would be generated in the presence of different levels or types of Y kinase activity. Y88 phosphorylation is the final switch that permits the p27 cyclin D-cdk4 ternary complex to be turned on, allowing both CAK activation and ATP coordination.

In summary, we have identified SH3 domain recruitment sequences within p27 that modulate Y88 phosphorylation and therefore cdk4 activity, and as such have identified a new and targetable regulatory region required for cdk4 activation and cell cycle progression. We have identified Brk/PTK6 as a physiological p27 kinase that can modulate cyclin D-cdk4 activity, and whose overexpression in breast cancer cells renders them resistant to cdk4-specific inhibition. We have also identified an endogenous inhibitor, Alt Brk, which adds to the regulation of cdk4 activity, and supports the importance of this interface as a bona fide therapeutic targeting site. p27 has long been considered a tumor suppressor, but our data further strengthens the idea that it should also be considered an oncogene, responsible for cyclin D-cdk4 activity.

REFERENCES

1. Bockstaele L, Coulonval K, Kooken H, Paternot S, Roger PP. (2006). Regulation of CDK4. Cell Division 1: 25.
2. Ortega, S, Malumbres, M, Barbacid M. (2002). Cyclin D-dependent kinases, INK4 inhibitors and cancer. Biochim Biophys. Acta 1602, 73-87.
3. Malumbres M, Barbacid M. (2006). Is Cyclin D1-CDK4 kinase a bona fide cancer target? Cancer Cell 9: 2-4.
4. Malumbres M, Sotillo R, Santamaria D, Galan J, Cerezo A, Ortega S, Dubus P, Barbacid M. (2004). Mammalian cells cycle without the D-type cyclin-dependent kinases Cdk4 and Cdk6. Cell 118: 493-504.
5. Yu Q, Geng Y, Sicinski P. (2001). Specific protection against breast cancers by cyclin D1 ablation. Nature 411: 1017-21.
6. Yu Q, Sicinska E, Geng Y, Ahnstrom M, Zagozdzon A, Kong Y, Gardner H, Kiyokawa H, Harris N L, Stal O, Sicinski P. (2006). Requirement for CDK4 kinase function in breast cancer. Cancer Cell 9: 23-32.
7. Sherr C J, Roberts J M. (1999). CDK inhibitors: positive and negative regulators of G1-phase progression. Genes Dev. 13: 1501-12.
8. Blain S W. (2008). Switching cyclin D-cdk4 kinase activity on and off. Cell Cycle 7: 892-898.
9. Jakel H, Peschel I, Kunze C, Weinl C, Hengst L. (2012). Regulation of p27 (Kip1) by mitogen-induced tyrosine phosphorylation. Cell Cycle 11: 1910-7.
10. Chu I, Sun J, Arnaout A, Kahn H, Hanna W, Narod S, Sun P, Tan C K, Hengst L, Slingerland J M. (2007). p27 phosphorylation by Src regulates inhibition of cyclin ECdk2. Cell 128: 281-94.
11. Grimmler M, Wang Y, Mund T, Cilensek Z, Keidel E M, Waddell M B, Jakel H, Kullmann M, Kriwacki R W, Hengst L. (2007). Cdk-inhibitory activity and stability of p27Kip1 are directly regulated by oncogenic tyrosine kinases. Cell 128: 269-80.
12. James M K, Ray A, Leznova D, Blain S W. (2008). Differential modification of p27Kip1 controls its cyclin D-cdk4 activity. Mol. Cell. Biol. 1: 498-510.
13. Kardinal C, Dangers M, Kardinal A, Koch A, Brandt D T, Tamura T, Welte K. (2005). Tyrosine phosphorylation modulates binding preference to a cyclin-dependent kinases and subcellular localization of p27 kip1 in the acute promyelocytic leukemia cell line NB4. Blood 107: 1133-1140.
14. Ray A, James M K, Larochelle S, Fisher R P, Blain S W. (2009). p27Kip1 inhibits cyclin D-cyclin-dependent kinase 4 by two independent modes. Mol. Cell Biol. 29: 986-99.
15. Russo A A, Jeffrey P D, Patten A, Massagué J, Pavletich N. (1996). Crystal structure of the p27Kip1 cyclin-dependent kinase inhibitor bound to the cyclin A-cdk2 complex. Nature 382: 325-331.
16. Galea C A, Nourse A, Wang Y, Sivakolundu S G, Heller W T, Kriwacki R W. (2008). Role of intrinsic flexibility in signal transduction mediated by the cell cycle regulator, p27 Kip1. J. Mol. Biol. 376: 827-38.
17. Jakel H, Weinl C, Hengst L. (2011). Phosphorylation of p27Kip1 by JΔK2 directly links cytokine receptor signaling to cell cycle control. Oncogene 30: 3502-12.
18. Manning G, Whyte D B, Martinez R, Hunter T, Sudarsanam S. (2002). The protein kinase complement of the human genome. Science 298: 1912-34.
19. Neet K, Hunter T. (1996). Vertebrate non-receptor protein-tyrosine kinase families Genes Cells 1: 147-69.
20. Serfas M S, Tyner A L. (2003). Brk, Srm, Frk, and Src42A form a distinct family of intracellular Src-like tyrosine kinases. Oncol. Res. 13: 409-19.
21. Harrison S C. (2003). Variation on an Src-like theme. Cell 112: 737-40.

22. Miller T W, Shirley T L, Wolfgang W J, Kang X, Messer A. (2003). DNA vaccination against mutant huntingtin ameliorates the HDR6/2 diabetic phenotype. Mol. Ther. 7: 572-9.
23. Qui H, Miller T W. (2004). Role of the Brk SH3 domain in substrate recognition. Oncogene 23: 2216-2223.
24. Brauer P M, Tyner A L. (2010). Building a better understanding of the intracellular tyrosine kinase PTK6-BRK by BRK. Biochim Biophys. Acta 1806: 66-73.
25. Mitchell P J, Barker K T, Martindale J E, Kamalati T, Lowe P N, Page M J, Gusterson B A, MR C. (1994). Cloning and characterisation of cDNAs encoding a novel non-receptor tyrosine kinase, brk, expressed in human breast tumours. Oncogene 9: 2383-2390.
26. Siyanova E, Serfas M, Mazo I, Tyner A. (1994). Tyrosine kinase gene expression in the mouse small intestine. Oncogene 9: 2053-2057.
27. Cesareni G, Panni S, Nardelli G, Castagnoli L. (2002). Can we infer peptide recognition specificity mediated by SH3 domains? FEBS Lett. 513: 38-44.
28. Asbach B, Ludwig C, Saksela K, Wagner R. (2012). Comprehensive analysis of interactions between the Src-associated protein in mitosis of 68 kDa and the human Src homology 3 proteome. PLoS One 6: e38540.
29. Ai M, Qiu S, Lu Y, Fan Z. (2013). HER2 regulates Brk/PTK6 stability via upregulating calpastatin, an inhibitor of calpain. Cell Signal. 25: 1754-61.
30. Qiu H, Zappacosta F, Su W, Annan R S, Miller W T. (2005). Interaction between Brk kinase and insulin receptor substrate-4. Oncogene 24: 5656-64.
31. Gierut J J, Mathur P S, Bie W, Han J, Tyner A L. (2012). Targeting protein tyrosine kinase 6 enhances apoptosis of colon cancer cells following DNA damage. J. Mol. Cancer Ther. 11: 2311-20.
32. Palka-Hamblin H L, Gierut J J, Bie W, Brauer P M, Zheng Y, Asara J M, Tyner A L. (2010). Identification of beta-catenin as a target of the intracellular tyrosine kinase PTK6. J. Cell Sc. 123: 236-45.
33. Schmidt M, Fernandez de Matto S, Van der Horst A, Klompmaker R, Kops G J, Lam E W, Burgering B M, Medema R H. (2002). Cell cycle inhibition by FoxO forkhead transcription factors involves downregulation of cyclin D. J. Mol. Cell. Biol. 22: 7842-52.
34. Baughn L B, Di Liberto M, Niesvizky R, Cho H J, Jayabalan D, Lane J, Liu F, Chen-Kiang S. (2009). CDK2 phosphorylation of Smad2 disrupts TGF-beta transcriptional regulation in resistant primary bone marrow myeloma cells. J. Immunol. 182: 1810-7.
35. Fry D W, Harvey P J, Keller P R, Elliott W L, Meade M, Trachet E, Albassam M, Zheng X, Leopold W R, Pryer N K, Toogood P L. (2004). Specific inhibition of cyclin-dependent kinase 4/6 by PD 0332991 and associated antitumor activity in human tumor xenografts. Mol. Cancer Ther. 3: 1427-38.
36. Finn R S, Dering J, Conklin D, Kalous O, Cohen D J, Desai A J, Ginther C, Atefi M, Chen I, Fowst C, Los G, Slamon D J. (2009). PD 0332991, a selective cyclin D kinase 4/6 inhibitor, preferentially inhibits proliferation of luminal estrogen receptor-positive human breast cancer cell lines. Breast Cancer Res. 5: R77.
37. Mitchell P J, Barker K T, Shipley J, Crompton M R. (1997). Characterisation and chromosome mapping of the human non receptor tyrsoine kinase gene, brk. Oncogene 15: 1497-502.
38. Brauer P M, Zheng Y, Evans M D, Dominguez-Brauer C, Peehl D M, Tyner A L. (2011). The alternative splice variant of protein tyrosine kinase 6 negatively regulates growth and enhances PTK6-mediated inhibition of β-catenin PLoS One 6: e14789.
39. Barker K T, Jackson L E, Crompton M R. (1997). BRK tyrosine kinase expression in a high proportion of human breast carcinomas. Oncogene 15: 799-805.
40. Ostrander J H, Daniel A R, Lofgren K, Kleer C G, Lange C A. (2007). Breast tumor kinase (protein tyrosine kinase 6) regulates heregulin-induced activation of ERK5 and p38 MAP kinases in breast cancer cells. Cancer Res. 67: 4199-209.
41. Peng M, Emmadi R, Wang Z, Wiley E L, Gann P H, Khan S, Banerji N, McDonald W, Asztalos S, Pham T N, Tonetti D A, Tyner A L. (2014). PTK6/BRK is expressed in the normal mammary gland and activated at the plasma membrane in breast tumors. Oncotarget 5: 6038-48.
42. Derry J J, Richard S, Valderrama Carvajal H, Ye X, Vasioukhin V, Cochrane A W, Chen T, Tyner A L. (2000). Sik (BRK) phosphorylates Sam68 in the nucleus and negatively regulates its RNA binding ability. Mol. Cell. Biol. 20: 6114-26.
43. Derry J J, Prins G S, Ray V, Tyner A L. (2003). Altered localization and activity of the intracellular tyrosine kinase BRK/Sik in prostate tumor cells Oncogene 22: 4212-20.
44. Zheng Y, Gierut J, Wang Z, Miao J, Asara J M, Tyner A L. (2012). Protein tyrosine kinase 6 protects cells from anoikis by directly phosphorylating focal adhesion kinase and activating AKT. Oncogene 32: 4304-12.
45. Zheng Y, Asara J M, Tyner A L. (2012). Protein-tyrosine kinase 6 promotes peripheral adhesion complex formation and cell migration by phosphorylating p130 CRK-associated substrate. J. Biol. Chem. 287: 148-58.
46. Chan E, Nimnual A S. (2010). Deregulation of the cell cycle by breast tumor kinase (Brk). Intl. J. Cancer 127: 2723-31.
47. Blain S W, Scher H I, Cordon-Cardo C, Koff A. (2003). p27 as a target for cancer therapeutics. Cancer Cell 3: 111-115.
48. Borriello A, Bencivenga D, Criscuolo M, Caldarelli I, Cucciolla V, Tramontano A, Borgia A, Spina A, Oliva A, Naviglio S, Della Ragione F. (2011). Targeting p27Kip1 protein: its relevance in the therapy of human cancer. Expert Opin. Ther. Targets 15: 677-93.
49. Hulit J, Lee R J, Russell R G, Pestell R G. (2002). ErbB-2-induced mammary tumor growth: the role of cyclin D1 and p27Kip1. Biochem. Pharm. 64: 827-36.
50. Muraoka R S, Lenferink A E G, Law B, Hamilton E, Brantley D M, Roebuck L R, Arteaga C L. (2002). Erb2/Neu-induced cyclin D1-dependent transformation is accelerated in p27-haploinsufficient mammary epithelial cells but impaired in p27-null cells. Mol. Cell. Biol. 22: 2204-2219.
51. Wander S A, Zhao D, Slingerland J M. (2011). p27: a barometer of signaling deregulation and potential predictor of response to targeted therapies. Clin. Cancer Res. 17: 12-8.
52. Hukkelhoven E, Liu Y, Yeh N, Ciznadija D, Blain S W, Koff A. (2012). Tyrosine phosphorylation of the p21 cyclin-dependent kinase inhibitor facilitates the development of proneural glioma. J. Biol. Chem. 46: 38523-30.
53. Dickson M A. (2014). Molecular pathways: CDK4 inhibitors for cancer therapy. Clin. Cancer Res. 20: 3379-83.
54. Cadoo K A, Gucalp A, Traina T A. (2014). Palbociclib: an evidence-based review of its potential in the treatment of breast cancer. J. Breast Cancer 6:123-33.

55. Heilmann A M, Perera R M, Ecker V, Nicolay B N, Bardeesy N, Benes C H, Dyson N J. (2014). CDK4/6 and IGF1 receptor inhibitors synergize to suppress the growth of p16INK4A-deficient pancreatic cancers. Cancer Res. 74: 3947-58.
56. Nguyen K D, Blain S W, Gress F, Treem W R. (2010). Inflammatory mediators of esophagitis alter p27 kip1 expression in esophageal epithelial cells. J. Pediatr. Gastroeneterol. Nun. 5, 556-62.
57. Vasioukhin V, Tyner A L. (1997). A role for the epithelial-cell-specific tyrosine kinase Sik during keratinocyte differentiation. Proc. Natl. Acad. Sci. 94: 14477-82.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A pharmaceutical composition comprising an isolated Alt-Brk peptide of SEQ ID NO: 17 or an SH3 domain containing fragment thereof and a carrier which enhances cellular uptake and optionally a cell penetrating peptide sequence, wherein said carrier is a lipoplexed nanoparticle, wherein said lipoplexed nanoparticle comprises 1,2-di-O-octdecenyl-3-trimethyl ammonium propane (DOTMA), cholesterol at a molar ratio of 49.5:49.5 and a pharmaceutically acceptable carrier, and a lipid to peptide mass ratio of 20:1 or 10:1.

2. The pharmaceutical composition of claim 1, said isolated Alt-Brk peptide of SEQ ID NO: 17 or an SH3 domain containing fragment thereof is packaged in a nanoparticle for in vivo delivery and inhibiting both CDK2 and CDK4 thereby causing cellular cancer cell senescence.

3. The pharmaceutical composition of claim 2, wherein said SH3 domain containing fragment is SEQ ID NO: 2 or SEQ ID NO: 17 and is truncated by 1, 2, 3 or 4 amino acids.

4. The pharmaceutical composition of claim 2, wherein said SH3 domain containing fragment is SEQ ID NO: 2 and comprises 1, 2, 3 or 4 mutated amino acids or SEQ ID NO: 17 comprises 1, 2, 3 or 4 mutated amino acids.

5. The pharmaceutical composition of claim 1, further comprising at least one anti-cancer agent, wherein said anticancer agent is selected from palbociclib, ribociclib, abemaciclib, osirmetinib, gefitinib, lapatinib, pantitumumab, vandetanib, necitumumab, vemurafenib, sorafenib tosylate, PLX-4720, dabrafenib, paclitaxel, cisplatin, docetaxol, carboplatin, vincristine, vinblastine, methotrexate, cyclophosphamide, CPT-11, 5-fluorouracil (5-FU), gemcitabine, estramustine, carmustine, doxorubicin, etoposide, arsenic trioxide, irinotecan, herceptin, vemurafenib, erlotininb, cetuximab, letrozole, fulvestrant and epothilone derivatives.

6. A pharmaceutical composition comprising an isolated Alt-Brk peptide of SEQ ID NO: 17 comprising 0, 1, 2, 3, or 4 mutated amino acids and truncated by 0, 1, 2, 3, or 4 amino acids, or of SEQ ID NO: 2 comprising 0, 1, 2, 3, or 4 mutated amino acids and truncated by 0, 1, 2, 3, or 4 amino acids, and a carrier which enhances cellular uptake and optionally a cell penetrating peptide sequence, wherein said carrier is a lipoplexed nanoparticle,
wherein said lipoplexed nanoparticle comprises 1,2-di-O-octdecenyl-3-trimethyl ammonium propane (DOTMA), cholesterol at a molar ratio of 49.5:49.5 and a pharmaceutically acceptable carrier, and a lipid to peptide mass ratio of 20:1 or 10:1.

7. The pharmaceutical composition of claim 6, further comprising at least one anti-cancer agent, wherein said anticancer agent is selected from palbociclib, ribociclib, abemaciclib, osirmetinib, gefitinib, lapatinib, pantitumumab, vandetanib, necitumumab, vemurafenib, sorafenib tosylate, PLX-4720, dabrafenib, paclitaxel, cisplatin, docetaxol, carboplatin, vincristine, vinblastine, methotrexate, cyclophosphamide, CPT-11, 5-fluorouracil (5-FU), gemcitabine, estramustine, carmustine, doxorubicin, etoposide, arsenic trioxide, irinotecan, herceptin, vemurafenib, erlotininb, cetuximab, letrozole, fulvestrant and epothilone derivatives.

8. The pharmaceutical composition of claim 1, wherein the cell penetrating peptide is selected from the group consisting of TAT and TAT variants, MPG peptide, Penetratin, EB1, VP22, Model amphipathic peptide, Pep-1, Transportan, TP-7, TP-9, TP-10, Protamine, Protamine-fragment, Poly-Lysine, Histidine-Lysine Peptides, Poly-Arginine, and gp41 fusion sequence.

9. The pharmaceutical composition of claim 1, further comprising D-α-tocopheryl polyethylene glycol 1000 succinate (TPGS).

10. The pharmaceutical composition of claim 6, wherein the cell penetrating peptide is selected from the group consisting of TAT and TAT variants, MPG peptide, Penetratin, EB1, VP22, Model amphipathic peptide, Pep-1, Transportan, TP-7, TP-9, TP-10, Protamine, Protamine-fragment, Poly-Lysine, Histidine-Lysine Peptides, Poly-Arginine, and gp41 fusion sequence.

11. The pharmaceutical composition of claim 6, further comprising D-α-tocopheryl polyethylene glycol 1000 succinate (TPGS).

* * * * *